US007534894B2

(12) United States Patent
Commons et al.

(10) Patent No.: US 7,534,894 B2
(45) Date of Patent: May 19, 2009

(54) BIPHENYLOXY-ACIDS

(75) Inventors: Thomas Joseph Commons, Wayne, PA (US); Susan Christman Croce, Lambertville, NJ (US); Eugene John Trybulski, Huntingdon Valley, PA (US); Hassan Mahmoud Elokdah, Yardley, PA (US); David LeRoy Crandall, Doylestown, PA (US)

(73) Assignee: Wyeth, Madison, NJ (US)

( * ) Notice: Subject to any disclaimer, the term of this patent is extended or adjusted under 35 U.S.C. 154(b) by 584 days.

(21) Appl. No.: 10/947,710

(22) Filed: Sep. 23, 2004

(65) Prior Publication Data

US 2006/0020003 A1    Jan. 26, 2006

Related U.S. Application Data

(60) Provisional application No. 60/505,989, filed on Sep. 25, 2003.

(51) Int. Cl.
*C07D 257/06* (2006.01)
*C07D 333/02* (2006.01)
*C07D 333/50* (2006.01)
*C07D 307/02* (2006.01)
*C07D 307/77* (2006.01)

(52) U.S. Cl. ............................ 548/253; 549/29; 549/429
(58) Field of Classification Search .................. 548/253
See application file for complete search history.

(56) References Cited

U.S. PATENT DOCUMENTS

| 3,026,325 | A | 3/1962 | Heinzelman et al. | 548/496 |
|---|---|---|---|---|
| 3,476,770 | A | 11/1969 | Scherrer | 548/494 |
| 3,557,142 | A | 1/1971 | Bell | 548/516 |
| 3,843,683 | A | 10/1974 | Bell | 548/493 |
| 4,042,711 | A | 8/1977 | Griss et al. | 514/563 |
| 4,478,819 | A | 10/1984 | Hercelin et al. | 424/457 |
| 4,736,043 | A | 4/1988 | Michel et al. | 548/492 |
| 4,851,406 | A | 7/1989 | Martens et al. | 514/217.04 |
| 5,141,948 | A | 8/1992 | Miyamoto et al. | 514/365 |
| 5,164,372 | A | 11/1992 | Matsuo et al. | 514/19 |
| 5,420,289 | A | 5/1995 | Musser et al. | 548/159 |
| 5,482,960 | A | 1/1996 | Berryman | 514/414 |
| 5,502,187 | A | 3/1996 | Ayer et al. | 544/117 |
| 5,541,343 | A | 7/1996 | Himmelsbach et al. | 514/424 |
| 5,612,360 | A | 3/1997 | Boyd et al. | 514/381 |
| 5,859,044 | A | 1/1999 | Dow et al. | 514/419 |
| 5,922,763 | A | 7/1999 | Himmelsbach et al. | 514/534 |
| 6,048,875 | A | 4/2000 | De Nanteuil et al. | 514/314 |
| 6,110,963 | A | 8/2000 | Malamas | 514/443 |
| 6,166,069 | A | 12/2000 | Malamas et al. | 514/469 |
| 6,211,214 | B1 | 4/2001 | Kramer et al. | 514/374 |
| 6,232,322 | B1 | 5/2001 | Malamas et al. | 514/303 |
| 6,251,936 | B1 | 6/2001 | Wrobel et al. | 514/443 |
| 6,302,837 | B1 | 10/2001 | De Nanteuil et al. | 514/337 |
| 6,380,430 | B1 | 4/2002 | Dorsch et al. | 564/243 |
| 6,479,524 | B1 | 11/2002 | Priepke et al. | 514/352 |
| 6,599,929 | B2 | 7/2003 | Cho et al. | 514/415 |
| 6,787,556 | B1 | 9/2004 | Hargreaves et al. | 514/311 |
| 6,800,645 | B1 | 10/2004 | Cox et al. | 514/314 |
| 6,800,654 | B2 | 10/2004 | Mayer et al. | 514/381 |
| 6,844,358 | B2 | 1/2005 | Malamas et al. | 514/336 |
| 2002/0123520 | A1 | 9/2002 | Marfat et al. | 514/365 |
| 2002/0193612 | A1* | 12/2002 | Chambers et al. | 549/200 |
| 2003/0013732 | A1 | 1/2003 | Elokdah | 514/301 |
| 2003/0018067 | A1 | 1/2003 | Elokdah et al. | 514/469 |
| 2003/0060497 | A1 | 3/2003 | Gerlach et al. | 514/414 |
| 2003/0125371 | A1 | 7/2003 | Elokdah et al. | 514/419 |
| 2004/0116488 | A1 | 6/2004 | Jennings et al. | 514/374 |
| 2004/0116504 | A1 | 6/2004 | Elokdah et al. | 514/419 |
| 2004/0122070 | A1 | 6/2004 | Jennings | 514/374 |
| 2004/0138283 | A1 | 7/2004 | Jennings et al. | 514/414 |
| 2004/0204417 | A1 | 10/2004 | Perez et al. | 514/249 |
| 2005/0070584 | A1 | 3/2005 | Havran et al. | 514/357 |
| 2005/0070585 | A1 | 3/2005 | Elokdah et al. | 514/364 |
| 2005/0070587 | A1 | 3/2005 | Elokdah et al. | 514/381 |
| 2005/0070592 | A1 | 3/2005 | Gundersen | 514/415 |
| 2005/0096377 | A1 | 5/2005 | Hu | 514/419 |
| 2005/0113428 | A1 | 5/2005 | Gopalsamy et al. | 514/364 |
| 2005/0113436 | A1 | 5/2005 | Elokdah et al. | 514/411 |
| 2005/0113438 | A1 | 5/2005 | Hu et al. | 514/414 |
| 2005/0113439 | A1 | 5/2005 | Hu | 514/414 |
| 2005/0119296 | A1 | 6/2005 | Elokdah et al. | 514/300 |
| 2005/0119326 | A1 | 6/2005 | Havran et al. | 514/414 |
| 2005/0119327 | A1 | 6/2005 | Hu | 514/414 |
| 2005/0215626 | A1 | 9/2005 | Havran et al. | 514/469 |
| 2006/0052348 | A1 | 3/2006 | Commons et al. | 514/92 |
| 2006/0052349 | A1 | 3/2006 | Commons et al. | 514/95 |
| 2006/0052420 | A1 | 3/2006 | Commons | 514/340 |

FOREIGN PATENT DOCUMENTS

CA    2387529    3/2001

(Continued)

OTHER PUBLICATIONS

Cancer and Metastasis Reviews (1998), 17 (1), 91-106.*
Science (1999), vol. 286, 531-537.*
Cancer [online], [retrieved on Jul. 6, 2007]. Retrieved from the Internet, URL; http://www.nlm.nih.gov/medlineplus/cancer.html>.*
Cancer [online],[retrieved on Jul. 6, 2007]. Retrieved from the Internet, URL; http://en.wikipedia.org/wiki/Cancer>.*
Cecil Textbook of Medicine, 20th edition (1996), vol. 2, pp. 2050-2057.*
Cecil Textbook of Medicine, 20th edition (1996), vol. 2, pp. 1992-1996.*

(Continued)

*Primary Examiner*—Rei-Tsang Shiao
*Assistant Examiner*—Shawquia Young
(74) *Attorney, Agent, or Firm*—Mabel Ng; Scott Larsen; David Kurlandsky

(57) ABSTRACT

The present invention relates generally to substituted biphenyloxy acids (such as 4'-aryl-amido-biphenyl-4(3)-yloxy-acids and 4'-aryl-amidomethyl-biphenyl-4(3)-yloxy-acids) and methods of using them, for example, as PAI-1 inhibitors.

23 Claims, No Drawings

FOREIGN PATENT DOCUMENTS

| | | |
|---|---|---|
| DE | 3147276 A1 | 6/1983 |
| DE | 43 38 770 A1 | 5/1995 |
| DE | 19543639 A1 | 5/1997 |
| DE | 19638047 A1 | 5/1997 |
| DE | 19753522 | 6/1999 |
| DE | 19819548 A1 | 11/1999 |
| DE | 19945302 A1 | 3/2001 |
| EP | 0 416 609 A2 | 3/1991 |
| EP | 483 667 A3 | 5/1992 |
| EP | 483 677 A2 | 5/1992 |
| EP | 0 496 378 A1 | 7/1992 |
| EP | 0 508 723 A1 | 10/1992 |
| EP | 0 512 570 A1 | 11/1992 |
| EP | 0 540 956 A1 | 5/1993 |
| EP | 0 574 808 A1 | 12/1993 |
| EP | 0 655 439 A2 | 5/1995 |
| EP | 0 696 584 A1 | 2/1996 |
| EP | 0 759 434 A1 | 2/1997 |
| EP | 0 819 686 A1 | 1/1998 |
| EP | 0 822 185 A1 | 2/1998 |
| EP | 0 937 464 A2 | 8/1999 |
| EP | 0 937 464 A3 | 8/1999 |
| EP | 0 955 299 A1 | 11/1999 |
| EP | 1 092 716 | 4/2001 |
| EP | 1 156 045 A1 | 11/2001 |
| FR | 2 777 886 | 10/1999 |
| FR | 2 777 886 A1 | 10/1999 |
| FR | 2 799 756 | 4/2001 |
| GB | 1 321 433 | 6/1973 |
| JP | 07228559 | 8/1995 |
| WO | WO 92/01675 A2 | 2/1992 |
| WO | WO 93/17682 A1 | 9/1993 |
| WO | WO 93/18035 A1 | 9/1993 |
| WO | WO 93/23040 A1 | 11/1993 |
| WO | 94/13637 A1 | 6/1994 |
| WO | 94/14434 A1 | 7/1994 |
| WO | 94/26738 A1 | 11/1994 |
| WO | WO 95/06482 A1 | 3/1995 |
| WO | 95/10513 A1 | 4/1995 |
| WO | 96/06840 A1 | 3/1996 |
| WO | 96/21656 A1 | 7/1996 |
| WO | 96/26207 A1 | 8/1996 |
| WO | WO 96/26207 | 8/1996 |
| WO | 96/32379 A1 | 10/1996 |
| WO | WO 96/32379 | 10/1996 |
| WO | WO 97/00854 A1 | 1/1997 |
| WO | 97/09308 A1 | 3/1997 |
| WO | 97/43260 A1 | 11/1997 |
| WO | 97/48697 A1 | 12/1997 |
| WO | 99/28297 A1 | 6/1999 |
| WO | WO 99/28297 | 6/1999 |
| WO | 99/43651 A2 | 9/1999 |
| WO | 99/43654 A2 | 9/1999 |
| WO | 99/43672 A1 | 9/1999 |
| WO | 99/46260 A1 | 9/1999 |
| WO | 99/50268 A1 | 10/1999 |
| WO | 99/58519 A1 | 11/1999 |
| WO | 99/61435 A1 | 12/1999 |
| WO | WO 00/16798 A1 | 3/2000 |
| WO | 00/32180 A2 | 6/2000 |
| WO | 00/35916 A1 | 6/2000 |
| WO | 00/46195 A1 | 8/2000 |
| WO | 00/46197 A1 | 8/2000 |
| WO | WO 00/64876 A1 | 11/2000 |
| WO | WO 00/64888 A1 | 11/2000 |
| WO | WO 01/05780 A1 | 1/2001 |
| WO | 01/12187 A2 | 2/2001 |
| WO | WO 01/21582 A1 | 3/2001 |
| WO | 02/30895 A1 | 4/2002 |
| WO | WO 02/44128 A2 | 6/2002 |
| WO | WO 02/44128 A3 | 6/2002 |
| WO | WO 02/060875 A1 | 8/2002 |
| WO | WO 02/060898 A1 | 8/2002 |
| WO | 02/072549 A1 | 9/2002 |
| WO | 03/000253 A1 | 1/2003 |
| WO | 03/000649 A1 | 1/2003 |
| WO | 03/031409 A1 | 4/2003 |
| WO | 03/068742 A1 | 8/2003 |
| WO | 03/087087 A2 | 10/2003 |
| WO | 2004/052854 A2 | 6/2004 |

OTHER PUBLICATIONS

FDA mulls drug to slow late-stage Alzheimer's [online], [retrieved on Sep. 23, 2003]. Retrieved from the Internet, URL; http://www.cnn.com/2003/HEALTH/conditions/09/24/alzheimers.drug.ap/indexhtml>.*

Diabetes Mellitus {DM} [online], [retrieved on Apr. 17, 2007]. Retrieved from the Internet, URL; http://www.merck.com/mmpe/print/sec12/ch158/ch158b.html>.*

Polycystic ovary disease [online], [retrieved on Feb. 25, 2008]. Retrieved from the Internet, URL; http://www.nlm.nih.gov/medlineplus/ency/article/000369>.*

Aggarwal et al., "A catalytic antibody programmed for torsional activation of amide bond hydrolysis," Chem. Eur. J., Jan. 25, 2003, 9(13), 3132-3142.

Ballantine, J. A., "The Chemistry of Bacteria," Journal of the Chemical Society Abstracts, 1957, 2222-2227.

Charlton, Peter, "The status of plasminogen activator inhibitor-1 as a therapeutic target," Expert Opinion On Investigational Drugs, May 1997, 6(5), 539-554.

Crandall, D. L. et al., "Characterization and comparative evaluation of a structurally unique PAI-1 inhibitor exhibiting oral in-vivo efficacy," Journal of Thrombosis and Haemostasis, Mar. 17, 2004, 2, 1422-1428.

Da Settmio, A. et al., "Reaction of indole derivatives with bromine, substitution, oxidation, and dimerization," J Org Chem, 1970, 35(8):2546-2551.

Delgado et al., Journal of Organic Chemistry (1993), 58(10), pp. 2862-2866.

Dillard R. D. et al., "Indole Inhibitors of Human Nonpancreatic Secretory Phospholipase $A_2$ 1. Indole-3-Acetamides", Journal of Medicinal Chemistry, American Chemical Society, 39(26), 5119-5136.

Guzzo, P.R. et al., "Synthesis of a conformationally constrained threonin-valine dipepetide mimetic: design of a potential inhibitor of plasminogen activator inhibitor-1," Tetrahedron Letters, 2002 43(1), 41-43.

Hipskind, P. A. et al., "Potent and selective 1,2,3-trisubstituted indole NPY Y-1 antagonists," J Med Chem, 1997, 40(23), 3712-3714.

Julia et al., CA 57:49169, 1962.

Malamas, M. S. et al., "Antihyperglycemic activity of new 1,2,4-oxadiazolidine-3,5-diones," Eur. J. Med. Chem., 2001, 36, 31-42.

Malamas, M.S. et al. "Novel benzofuran and benzothiophene biphenyls as inhibitors of protein tyrosine phosphatase 1B with antihyperglycemic properties," Journal of Medicinal Chemistry, Apr. 6, 2000, 43(7), 1293-1310.

Moody et al., CA 120:298300, 1994.

Shengeliya, M. S. et al., "N-Glycosides of 5-amino-2-(ethoxycarbonyl)indole," Zhurnal Organicheskoi Khimii, 1986, 22(9), 1868-1873.

U.S. Appl. No. 10/947,711, filed Sep. 23, 2004, Gopalsamy et al.

Krishnamurti, C. et al., "Plasminogen Activator Inhibitor: A Regulator of Ancrod-Induced Firbin Deposition in Rabbits," Blood, 69(3): 798-803 (Mar. 1987).

Reilly, C. et al., "Both Circulating and Clot-Bound Plasminogen Activator-1 Inhibit Endogenous Fibrinolysis in the Rat," Arteriosclerosis and Thrombosis, 11(5): 1276-1286 (Sep./Oct. 1991).

Carmeliet, P. et al., "Plasminogen Activator Inhibitor -1 Gene-deficient Mice," Journal of Clinical Investigation, 92: 2756-2760 (Dec. 1993).

Rocha, E. et al., "The Relationship Between Impaired Fibrinolysis and Coronary Heart Disease," Fibrinolysis, 8: 294-303 (1994).

Aznar, J. et al., "Role of Plasminogen Activator Inhibitor Type 1 in the Pathogenesis of Coronary Artery Diseases," *Haemostasis* 24: 243-251 (1994).

Biemond, B. J. et al., "Thrombolysis and Reocclusion in Experimental Jugular Vein and Coronary Artery Thrombosis," *Circulation*, 91: 1175-1181 (1995).

Levi, M. et al., "Inhibition of Plasminogen Activator Inhibitor-1 Activity Results in Promotion of Endogenous Thrombolysis and Inhibition of Thrombus Experimental Thrombosis," *Circulation* 85:305-312 (1992).

Nordt, T. K. et al., "Differential Regulation by Troglitazone of Plasminogen Activator Inhibitor Type 1 in Human Hepatic and Vascular Cells," *Journal of Clinical Endocrinology and Metabolism*, 85(4):1563-1568 (2000).

Daci, E. et al., "Mice Lacking the Plasminogen Activator Inhibitor 1 are Protected from Trabecular Bone Loss Induced by Estrogen Deficiency," *Journal of Bone and Mineral Research*, 15(8):1510-1516 (Nov. 8, 2000).

Schneiderman J. et. al., "Increased type 1 plasminogen activator inhibitor gene expression in atherosclerotic human arteries," *Proc Natl Acad Sci* 89: 6998-7002 (Aug. 1992).

Juhan-Vague, I. et. al., "Deficient t-PA Release and Elevated PA Inhibitor Levels in Patients with Spontaneous or Recurrent Deep Venous Thrombosis," *Thromb Haemost* 57: 67-72 (1987).

Juhan-Vague, I. et. al., "PAI-1, Obesity, Insulin Resistance and Risk of Cardiovascular Events," *Thromb Haemost* 78: 565-660 (1997).

Hamsten, A. et. al., "Plasminogen Activator Inhibitor in Plasma: Risk Factor For Recurrent Myocardial Infarction," *Lancet* 2: 3-9 (Jul. 4, 1987).

Siemens, H. J. et. al., "Course of Molecular Hemostatic Markers During and After Different Surgical Procedures," *J Clin Anesthesia* 11: 622-629 (Dec. 1999).

Koh, K. et. al., "Effects of Hormone-Replacement Therapy on Fibrinolysis in Postmenopausal Women," *N Engl J Med* 336(10): 683-690 (Mar. 6, 1997).

* cited by examiner

BIPHENYLOXY-ACIDS

CROSS-REFERENCE TO RELATED APPLICATIONS

This application claims the benefit of U.S. Provisional Application No. 60/505,989 filed Sep. 25, 2003, the entire disclosure of which is incorporated herein by reference.

BACKGROUND

The present invention relates generally to substituted biphenyloxy-acids including aryl-amido-biphenyloxy-acids and aryl-amidomethyl-biphenyloxy-acidic acids (such as 4'-aryl-amido-biphenyl-4(3)-yloxy-acids and 4'-aryl-amidomethyl-biphenyl-4(3)-yloxy-acids) and methods of using them.

The serine protease inhibitor PAI-1 is one of the primary inhibitors of the fibrinolytic system. The fibrinolytic system includes the proenzyme plasminogen, which is converted to the active enzyme, plasmin, by one of two tissue type plasminogen activators, t-PA or u-PA. PAI-1 is the principal physiological inhibitor of t-PA and u-PA. One of plasmin's main responsibilities in the fibrinolytic system is to digest fibrin at the site of vascular injury. The fibrinolytic system, however, is not only responsible for the removal of fibrin from circulation but is also involved in several other biological processes including ovulation, embryogenesis, intima proliferation, angiogenesis, tumorigenesis, and atherosclerosis.

Elevated levels of PAI-1 have been associated with a variety of diseases and conditions including those associated with impairment of the fibrinolytic system. For example, elevated levels of PAI-1 have been implicated in thrombotic diseases, e.g., diseases characterized by formation of a thrombus that obstructs vascular blood flow locally or detaches and embolizes to occlude blood flow downstream. (Krishnamurti, *Blood,* 69, 798 (1987); Reilly, Arteriosclerosis and Thrombosis, 11, 1276 (1991); Carmeliet, *Journal of Clinical Investigation,* 92, 2756 (1993), Rocha, *Fibrinolysis,* 8, 294, 1994; Aznar, *Haemostasis* 24, 243 (1994)). Antibody neutralization of PAI-1 activity resulted in promotion of endogenous thrombolysis and reperfusion (Biemond, *Circulation,* 91, 1175 (1995); Levi, *Circulation* 85, 305, (1992)). Elevated levels of PAI-1 have also been implicated in diseases such as polycystic ovary syndrome (Nordt, *Journal of clinical Endocrinology and Metabolism,* 85, 4, 1563 (2000)), bone loss induced by estrogen deficiency (Daci, *Journal of Bone and Mineral Research,* 15, 8, 1510 (2000)), cystic fibrosis, diabetes, chronic periodontitis, lymphomas, diseases associated with extracellular matrix accumulation, malignancies and diseases associated with neoangiogenesis, inflammatory diseases, vascular damage associated with infections, and diseases associated with increased uPA levels such as breast and ovarian cancer.

In view of the foregoing, there exists a need for the identification of inhibitors of PAI-1 activity and for methods of using the identified inhibitors to modulate PAI-1 expression or activity in a subject in order to treat disorders associated with elevated PAI-1 levels.

SUMMARY

The present invention provides substituted biphenyloxy acids and methods of using them. In certain embodiments, 4'-aryl-amido-biphenyl-4(3)-yloxy-acids and 4'-aryl-amidomethyl-biphenyl-4(3)-yloxy-acids are provided, including those of the following formula:

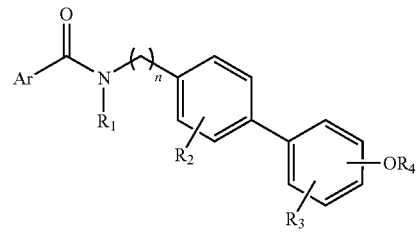

Formula 1 wherein:

Ar is phenyl, naphthyl, furanyl, thiophenyl, benzofuranyl, benzothiophenyl, indolyl, pyrazolyl, oxazolyl, fluorenyl, phenylcycloalkyl, or dihydroindenyl;

$R_1$ is hydrogen, $C_1$-$C_6$ alkyl or —$(CH_2)_r$-phenyl;

$R_2$ and $R_3$ are, independently, hydrogen, $C_1$-$C_6$ alkyl, —$(CH_2)_p$-phenyl, halogen or $C_1$-$C_3$ perfluoroalkyl;

$R_4$ is —$CHR_5CO_2H$, —$CH_2$-tetrazole or an acid mimic;

$R_5$ is hydrogen or benzyl;

n is 0 or 1;

r is from 0 to 6;

p is from 0 to 3.

Such compounds include:

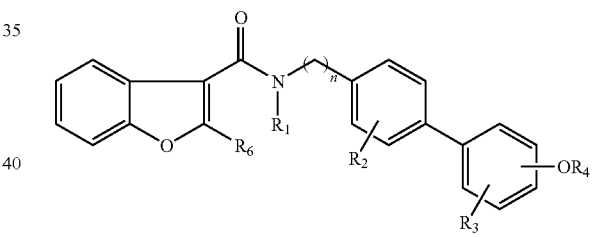

Formula 2

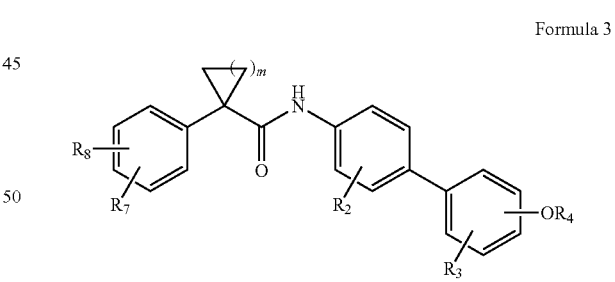

Formula 3

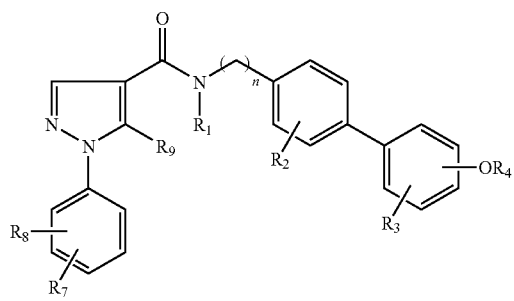

Formula 4

-continued

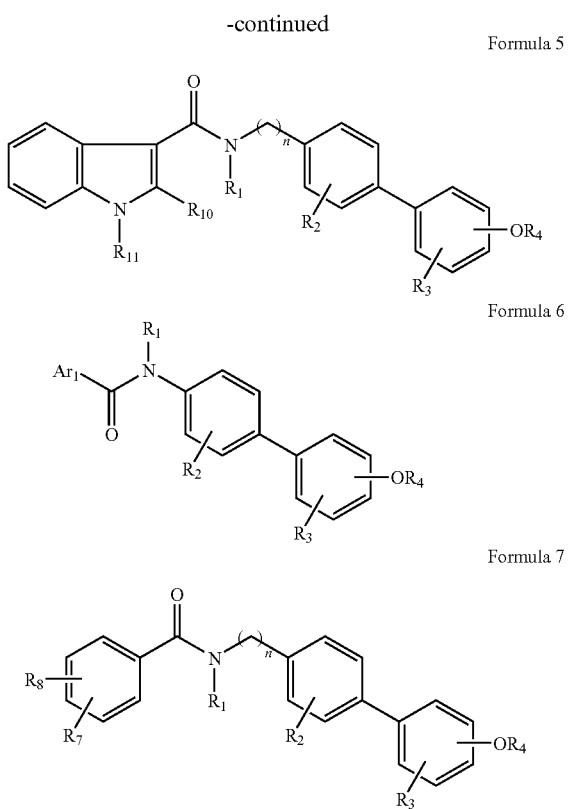

Formula 5

Formula 6

Formula 7 wherein

Ar, $R_1$, $R_2$, $R_3$, $R_4$, $R_5$, n, r, and p are as defined above;

$R_6$, $R_7$, $R_8$, $R_9$, $R_{10}$, and $R_{12}$ are, independently, hydrogen, $C_1$-$C_6$ alkyl, $C_1$-$C_6$ alkoxy, hydroxy, —$(CH_2)_q$-phenyl, —$O(CH_2)_q$-phenyl, $C_3$-$C_6$ cycloalkyl, halogen, $C_1$-$C_3$ perfluoroalkyl or $C_1$-$C_3$ perfluoroalkoxy;

m is from 1 to 4;

q is from 0 to 6;

$R_{11}$ is hydrogen, $C_1$-$C_6$ alkyl, —$(CH_2)_q$-phenyl, or —$(CH_2)_q$—$C_3$-$C_6$ cycloalkyl and q is from 0 to 6.; and $Ar_1$ is formula A or formula B

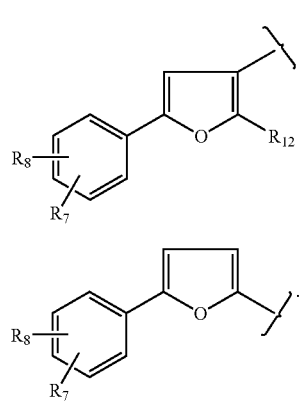

Formula A

Formula B

The present invention also provides, inter alia, pharmaceutically acceptable salt or ester forms of compounds of formulas 1-7.

The present invention further provides, inter alia, methods of using substituted biphenyloxy acids. In one aspect of the present invention, a therapeutically effective amount of one or more compounds of the present invention is administered to a subject in order to treat a PAI-1 related disorder, e.g., by inhibiting PAI-1 activity in the subject. PAI-1 activity is associated with a number of diseases and conditions. For example, in one embodiment of the present invention, PAI-1 activity is associated with impairment of the fibrinolytic system. In other embodiments, PAI-1 activity is associated with thrombosis, e.g., venous thrombosis, arterial thrombosis, cerebral thrombosis, and deep vein thrombosis, atrial fibrillation, pulmonary fibrosis, thromboembolic complications of surgery, cardiovascular disease, e.g., myocardial ischemia, atherosclerotic plaque formation, chronic obstructive pulmonary disease, renal fibrosis, polycystic ovary syndrome, Alzheimer's disease, or cancer.

DETAILED DESCRIPTION

A. General Overview

The present invention provides compounds that inhibit PAI-1 activity, processes for preparing such compounds, pharmaceutical compositions containing such compounds, and methods for using such compounds in medical therapies. The compounds have properties that are useful for the treatment, including the prevention and inhibition, of a wide variety of diseases and disorders involving the production and/or action of PAI-1. These include disorders resulting from impairment of the fibrinolytic system including, but not limited to, thrombosis, coronary heart disease, renal fibrosis, atherosclerotic plaque formation, pulmonary disease, myocardial ischemia, atrial fibrillation, coagulation syndromes, thromboembolic complications of surgery, peripheral arterial occlusion and pulmonary fibrosis. Other disorders include, but are not limited to, polycystic ovary syndrome, Alzheimer's disease, and cancer.

The terms "alkyl" and "alkylene," as used herein, whether used alone or as part of another group, refer to substituted or unsubstituted aliphatic hydrocarbon chains, the difference being that alkyl groups are monovalent (i.e., terminal) in nature whereas alkylene groups are divalent and typically serve as linkers. Both include, but are not limited to, straight and branched chains containing from 1 to about 12 carbon atoms, preferably 1 to about 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted. Representative optional substituents include, but are not limited to, hydroxy, oxo (=O), acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Preferred substituents include halogens, —CN, —OH, oxo (=O), and amino groups.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to about 10 carbon atoms (unless explicitly specified otherwise) and containing at least one double bond. Preferably, the alkenyl moiety has 1 or 2 double bonds. Such alkenyl moieties can exist in the E or Z conformations and the compounds of this invention include both conformations. Specifically included within the definition of "alkenyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Heteroatoms, such as O or S attached to an alkenyl should not be attached to a carbon atom that is bonded to a double bond. Preferred substituents include halogens, —CN, —OH, and amino groups The term "alkynyl", as used herein, whether used alone or as part of another group, refers to a substituted or unsubstituted aliphatic hydrocarbon chain and includes, but is not limited to, straight and branched chains having 2 to about 10 carbon atoms (unless explicitly specified otherwise) and containing at least one triple bond. Preferably, the alkynyl moiety has about 2 to about 7 carbon atoms. In certain embodiments, the alkynyl can contain more than one triple bond and, in such cases, the alkynyl group must contain at least three carbon atoms. Specifically included within the definition of "alkynyl" are those aliphatic hydrocarbon chains that are optionally substituted. Representative optional substituents include, but are not limited to, hydroxy, acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl. Preferred substituents include halogens, —CN, —OH, and amino groups Heteroatoms, such as O or S attached to an alkynyl should not be attached to the carbon that is bonded to a triple bond.

The term "cycloalkyl" as used herein, whether alone or as part of another group, refers to a substituted or unsubstituted alicyclic hydrocarbon group having 3 to about 20 carbon atoms (unless explicitly specified otherwise), preferably 3 to about 6 carbon atoms. Specifically included within the definition of "cycloalkyl" are those alicyclic hydrocarbon groups that are optionally substituted. Representative optional substituents include, but are not limited to, hydroxy, oxo (=O), acyloxy, alkoxy, amino, amino substituted by one or two alkyl groups of from 1 to 6 carbon atoms, aminoacyl, acylamino, thioalkoxy of from 1 to 6 carbon atoms, substituted thioalkoxy of from 1 to 6 carbon atoms, and trihalomethyl.

The term "aryl", as used herein, whether used alone or as part of another group, is defined as a substituted or unsubstituted aromatic hydrocarbon ring group having 5 to about 50 carbon atoms (unless explicitly specified otherwise) with from about 6 to about 14 atoms being preferred. The "aryl" group can have a single ring or multiple condensed rings. The term "aryl" includes, but is not limited to phenyl, α-naphthyl, β-naphthyl, biphenyl, anthryl, tetrahydronaphthyl, fluorenyl, indanyl, biphenylenyl, and acenaphthenyl. Specifically included within the definition of "aryl" are those aromatic groups that are optionally substituted. In representative embodiments of the present invention, the, "aryl" groups are optionally substituted with from 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. For example, the "aryl" groups can be optionally substituted with from 1 to 3 groups selected from $C_1$-$C_6$ alkyl, $C_1$-$C_6$ alkoxy, hydroxy, $C_3$-$C_6$ cycloalkyl, —($CH_2$)—$C_3$-$C_6$ cycloalkyl, halogen, $C_1$-$C_3$ perfluoroalkyl, $C_1$-$C_3$ perfluoroalkoxy, —($CH_2$)$_q$-phenyl, and —O($CH_2$)$_q$-phenyl. In these embodiments, the phenyl group of —($CH_2$)$_q$-phenyl and —O($CH_2$)$_q$-phenyl can be optionally substituted with from 1 to 3 groups selected from $C_1$-$C_6$ alkyl, $C_1$-$C_6$ alkoxy, phenyl, halogen, trifluoromethyl or trifluoromethoxy. In other embodiments, phenyl groups of the present invention are optionally substituted with from 1 to 3 groups selected from $C_1$-$C_6$ alkyl, $C_1$-$C_6$ alkoxy, —($CH_2$)$_p$-phenyl, halogen, trifluoromethyl or trifluoromethoxy. Preferred aryl groups include phenyl and naphthyl. Preferred substituents on the aryl groups herein include alkyl, alkoxy, halo, cyano, nitro, trihalomethyl, and thioalkoxy.

As used herein, the term "heteroaryl", whether used alone or as part of another group, is defined as a substituted or unsubstituted aromatic heterocyclic ring system (monocyclic or bicyclic). Heteroaryl groups can have, for example, from about 3 to about 50 carbon atoms (unless explicitly specified otherwise), with from about 4 about 10 being preferred. In some embodiments, heteroaryl groups are aromatic heterocyclic ring systems having about 4 to about 14 ring atoms and containing carbon atoms and 1, 2, or 3 oxygen, nitrogen or sulfur heteroatoms. Representative heteroaryl groups are furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Specifically included within the definition of "heteroaryl" are those aromatic heterocyclic rings that are substituted with 1 to 5 substituents selected from the group consisting of acyloxy, hydroxy, acyl, alkyl of 1 to 6 carbon atoms, alkoxy of 1 to 6 carbon atoms, alkenyl of 2 to 6 carbon atoms, alkynyl of 2 to 6 carbon atoms, substituted alkyl, substituted alkoxy, substituted alkenyl, substituted alkynyl, amino, amino substituted by one or two alkyl groups of from 1 to 6 carbon atoms, aminoacyl, acylamino, azido, cyano, halo, nitro, thioalkoxy of from 1 to 6 carbon atoms, substituted thioalkoxy of from 1 to 6 carbon atoms, and trihalomethyl. In some embodiments of the present invention, the "heteroaryl" groups can be optionally substituted with from 1 to 3 groups selected from $C_1$-$C_6$ alkyl, $C_1$-$C_6$ alkoxy, hydroxy, $C_3$-$C_6$ cycloalkyl, —($CH_2$)—$C_3$-$C_6$ cycloalkyl, halogen, $C_1$-$C_3$ perfluoroalkyl, $C_1$-$C_3$ perfluoroalkoxy, —($CH_2$)$_q$-phenyl, and —O($CH_2$)$_q$-phenyl. In these embodiments, the phenyl group of —($CH_2$)$_q$-phenyl and —O($CH_2$)$_q$-phenyl can be optionally substituted with from 1 to 3 groups selected from $C_1$-$C_6$ alkyl, $C_1$-$C_6$ alkoxy, phenyl, halogen, trifluoromethyl or trifluoromethoxy. Preferred heterocycles of the present invention include substituted and unsubstituted furanyl, thiophenyl, benzofuranyl, benzothiophenyl, indolyl, pyrazolyl, oxazolyl, and fluorenyl.

As used herein, the term "phenylcycloalkyl", whether used alone or as part of another group, refers to the group $R_a$—$R_b$— wherein $R_b$ is an optionally substituted cyclized alkyl group having from about 3 to about 10 carbon atoms with from about 3 to about 6 being preferred and $R_a$ is an optionally substituted phenyl group as described above. Preferred cycloalkyl groups are cyclopropyl, cyclobutyl, cyclopentyl or cyclohexyl. Examples of phenylcycloalkyl also include groups of formula:

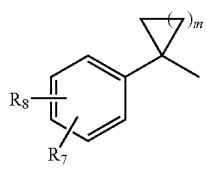

wherein $R_7$ and $R_8$ are, independently, hydrogen, $C_1$-$C_6$ alkyl, $C_1$-$C_6$ alkoxy, hydroxy, —$(CH_2)_q$-phenyl, —$O(CH_2)_q$-phenyl, $C_3$-$C_6$ cycloalkyl, halogen, $C_1$-$C_3$ perfluoroalkyl or $C_1$-$C_3$ perfluoroalkoxy; m is from 1 to 4, and q=0-6.

The term "alkoxy" as used herein, refers to the group $R_a$—O— wherein $R_a$ is an alkyl group as defined above. Specifically included within the definition of "alkoxy" are those alkoxy groups that are optionally substituted. Preferred substituents on alkoxy and thioalkoxy groups include halogens, —CN, —OH, and amino groups The term "arylalkyl" or "aralkyl" refers to the group —$R_a$—$R_b$, where $R_a$ is an alkyl group as defined above, substituted by $R_b$, an aryl group, as defined above. Aralkyl groups of the present invention are optionally substituted. Examples of arylalkyl moieties include, but are not limited to, benzyl, 1-phenylethyl, 2-phenylethyl, 3-phenylpropyl, 2-phenylpropyl and the like.

The term "perfluoroalkyl", as used herein, whether used alone or as part of another group, refers to a saturated aliphatic hydrocarbon having 1 to 6 carbon atoms and two or more fluorine atoms and includes, but is not limited to, straight or branched chains, such as —$CF_3$, —$CH_2CF_3$, —$CF_2CF_3$ and —$CH(CF_3)_2$.

The term "halogen" or "halo" refers to chlorine, bromine, fluorine, and iodine.

The term "treating" or "treatment" refers to any indicia of success in amelioration of an injury, pathology, or condition, including any objective or subjective parameter such as abatement; remission; diminishing of symptoms or making the injury, pathology, or condition more tolerable to the patient; slowing in the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" or "treatment of a PAI-1 related disorder" includes preventing the onset of symptoms in a subject that may be predisposed to a PAI-1 related disorder but does not yet experience or exhibit symptoms of the disorder (prophylactic treatment), inhibiting the symptoms of the disorder (slowing or arresting its development), providing relief from the symptoms or side-effects of the disorder (including palliative treatment), and/or relieving the symptoms of the disorder (causing regression). Accordingly, the term "treating" includes the administration of the compounds or agents of the present invention to a subject to prevent or delay, to alleviate, or to arrest or inhibit development of the symptoms or conditions associated with PAI-1 related disorders, e.g., tumor growth associated with cancer. A skilled medical practitioner will know how to use standard methods to determine whether a patient is suffering from a disease associated with enhanced levels and/or activity of PAI-1, e.g., by examining the patient and determining whether the patient is suffering from a disease known to be associated with elevated PAI-1 levels or activity or by assaying for PAI-1 levels in blood plasma or tissue of the individual suspected of suffering from a PAI-1 related disease and comparing PAI-1 levels in the blood plasma or tissue of the individual suspected of suffering from a PAI-1 related disease to PAI-1 levels in the blood plasma or tissue of a healthy individual. Increased PAI-1 levels are indicative of disease. Accordingly, the present invention provides, inter alia, methods of administering a compound of the present invention to a subject and determining levels of PAI-1 in the subject. The level of PAI-1 in the subject can be determined before and/or after administration of the compound.

In healthy individuals, PAI-1 is found at low levels in the plasma (from about 5-26 ng/mL), but it is elevated in many PAI-1 related disorders, including, for example, atherosclerosis (Schneiderman J. et. al, *Proc Natl Acad Sci* 89: 6998-7002, 1992) deep vein thrombosis (Juhan-Vague I, et. al, *Thromb Haemost* 57: 67-72, 1987), and non-insulin dependent diabetes mellitus (Juhan-Vague I, et. al, *Thromb Haemost* 78: 565-660, 1997). PAI-1 stabilizes both arterial and venous thrombi, contributing respectively to coronary arterial occlusion in post-myocardial infarction (Hamsten A, et. al. *Lancet* 2:3-9, 1987), and venous thrombosis following postoperative recovery from orthopedic surgery. (Siemens H J, et. al, *J Clin Anesthesia* 11: 622-629, 1999). Plasma PAI-1 is also elevated, for example, in postmenopausal women, and has been proposed to contribute to the increased incidence of cardiovascular disease in this population (Koh K et. al, *N Engl J Med* 336: 683-690, 1997).

The term "PAI-1 related disorder or disease" refers to any disease or condition that is associated with increased or enhanced expression or activity of PAI-1 or increased or enhanced expression or activity of a gene encoding PAI-1. Examples of such increased activity or expression can include one or more of the following: activity of the protein or expression of the gene encoding the protein is increased above the level of that in normal subjects; activity of the protein or expression of the gene encoding the protein is in an organ, tissue or cell where it is not normally detected in normal subjects (i.e. spatial distribution of the protein or expression of the gene encoding the protein is altered); activity of the protein or expression of the gene encoding the protein is increased when activity of the protein or expression of the gene encoding the protein is present in an organ, tissue or cell for a longer period than in a normal subjects (i.e., duration of activity of the protein or expression of the gene encoding the protein is increased). A normal or healthy subject is a subject not suffering from a PAI-1 related disorder or disease.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" refers to salts and esters that are pharmaceutically acceptable and have the desired pharmacological properties. Such salts include, for example, salts that can be formed where acidic protons present in the compounds are capable of reacting with inorganic or organic bases. Suitable inorganic salts include, for example, those formed with the alkali metals or alkaline earth metals, e.g. sodium and potassium, magnesium, calcium, and aluminum. Suitable organic salts include, for example, those formed with organic bases such as the amine bases, e.g. ethanolamine, diethanolamine, triethanolamine, trimethamine, N methylglucamine, and the like. Pharmaceutically acceptable salts can also include acid addition salts formed from the reaction of basic moieties, such as amines, in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g. $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention can be present in more than one stereoisomeric form, and the naming of such compounds is intended to include all single stereoisomers and all mixtures (whether racemic or otherwise) of such stereoisomers.

"Inhibitors," "activators," and "modulators" of expression or of activity are used to refer to inhibitory, activating, or modulating molecules, respectively, identified using in vitro and in vivo assays for expression or activity. Inhibitors of the present invention are compositions that, inhibit expression of PAI-1 or bind to, partially or totally block stimulation, decrease, prevent, delay activation, inactivate, desensitize, or down regulate the activity of PAI-1. Samples or assays comprising PAI-1 can be treated with a composition of the present invention and compared to control samples without a composition of the present invention. Control samples (untreated with compositions of the present invention) can be assigned a relative activity value of 100%. In certain embodiments, inhibition of PAI-1 is achieved when the activity value relative to the control is about 80% or less, optionally 50% or 25, 10%, 5% or 1%.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the compound.

A "therapeutically effective amount" or "pharmaceutically effective amount" means the amount that, when administered to a subject, produces effects for which it is administered. For example, a "therapeutically effective amount," when administered to a subject to inhibit PAI-1 activity, is sufficient to inhibit PAI-1 activity. A "therapeutically effective amount," when administered to a subject for treating a disease, is sufficient to effect treatment for that disease.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and formulations of the present invention.

When any variable occurs more than one time in any constituent or in any formula, its definition in each occurrence is independent of its definition at every other occurrence. Combinations of substituents and/or variables are permissible only if such combinations result in stable compounds.

B. Substituted Biphenyloxy Acids

The present invention provides substituted biphenyloxy acids. Such compounds are preferably administered to inhibit PAI-1 expression or activity in a subject and, ultimately, to treat diseases or conditions associated with increased PAI-1 activity in a subject, e.g., a PAI-1 related disorder.

The compounds of the present invention include those of the following formula:

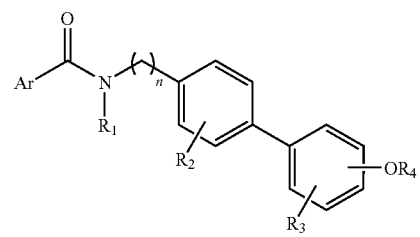

Formula 1 wherein:

Ar is phenyl, naphthyl, furanyl, thiophenyl, benzofuranyl, benzothiophenyl, indolyl, pyrazolyl, oxazolyl, fluorenyl, phenylcycloalkyl, or dihydroindenyl;

$R_1$ is hydrogen, $C_1$-$C_6$ alkyl or —$(CH_2)_r$-phenyl;

$R_2$ and $R_3$ are independently hydrogen, $C_1$-$C_6$ alkyl, —$(CH_2)_p$-phenyl, halogen, or $C_1$-$C_3$ perfluoroalkyl;

$R_4$ is —$CHR_5CO_2H$, —$CH_2$-tetrazole or an acid mimic;

$R_5$ is hydrogen or benzyl;

n is 0 or 1;

r is from 0 to 6;

p is from 0 to 3.

Ar may be unsubstituted or optionally substituted with for example from 1 to 3 groups the same or different selected from the group consisting of $C_1$-$C_6$ alkyl, $C_1$-$C_6$ alkoxy, hydroxy, $C_3$-$C_6$cycloalkyl, —$(CH_2)$—$C_3$-$C_6$cycloalkyl, halogen, $C_1$-$C_3$ perfluoroalkyl, $C_1$-$C_3$ perfluoroalkoxy, —$(CH_2)_q$-phenyl, and —$O(CH_2)_q$-phenyl and wherein the phenyl group of —$(CH_2)_q$-phenyl and —$O(CH_2)_q$-phenyl is optionally substituted with from 1 to 3 groups selected from the group consisting of $C_1$-$C_6$ alkyl, $C_1$-$C_6$ alkoxy, phenyl, halogen, trifluoromethyl or trifluoromethoxy; and q is from 0 to 6.

Such compounds of formula I include:

Formula 2

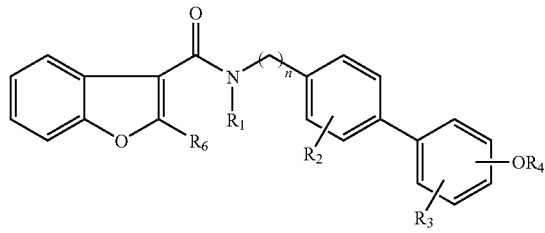

Formula 3

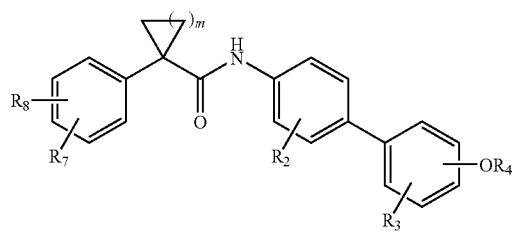

Formula 4

![Formula 4 structure]

Formula 5

![Formula 5 structure]

Formula 6

![Formula 6 structure]

Formula 7

![Formula 7 structure]

wherein:
Ar, $R_1$, $R_2$, $R_3$, $R_4$, $R_5$, n, r, and p are as defined above;
$R_6$, $R_7$, $R_8$, $R_9$, $R_{10}$, and $R_{12}$ are, independently, hydrogen, $C_1$-$C_6$ alkyl, $C_1$-$C_6$ alkoxy, hydroxy, —$(CH_2)_q$-phenyl, —$O(CH_2)_q$-phenyl, $C_3$-$C_6$ cycloalkyl, halogen, $C_1$-$C_3$ perfluoroalkyl or $C_1$-$C_3$ perfluoroalkoxy;
m is from 1 to 4;
q is from 0 to 6;
$R_{11}$ is hydrogen, $C_1$-$C_6$ alkyl, —$(CH_2)_q$-phenyl, or —$(CH_2)_q$-$C_3$-$C_6$ cycloalkyl and q is from 0 to 6; and
$Ar_1$ is formula A or formula B Formula A ![Formula A structure]

Formula B

![Formula B structure]

Compounds of the present invention also include prodrugs, stereoisomers, or pharmaceutically acceptable salt or ester forms of formulas 1 to 7.

For use in the present invention, $R_1$ can be hydrogen, $C_1$-$C_6$ alkyl or —$(CH_2)_r$-phenyl wherein the phenyl ring is optionally substituted with alkyl, alkoxy, halogen, trifluoromethyl, or trifluoromethoxy. In certain embodiments of the present invention, $R_1$ is alkyl, aralkyl, or hydrogen. For example, in some embodiments, $R_1$ is methyl, benzyl, or hydrogen. In such embodiments, Ar, $R_2$, $R_3$, $R_4$, $R_5$, $R_6$, $R_7$, $R_8$, $R_9$, $R_{10}$, $R_{11}$, $R_{12}$, n, m, q, r, p, and $Ar_1$ are as described herein.

$R_2$ and $R_3$ can be, independently, hydrogen, $C_1$-$C_6$ alkyl, halogen, $C_1$-$C_3$ perfluoroalkyl, or —$(CH_2)_p$-phenyl wherein the phenyl ring is optionally substituted with alkyl, alkoxy, halogen, trifluoromethyl, or trifluoromethoxy. In certain embodiments of the present invention, $R_2$ is hydrogen and $R_3$ is hydrogen, alkyl, or halogen. For example $R_3$ is hydrogen, methyl or bromine. In such embodiments, Ar, $R_1$, $R_4$, $R_5$, $R_6$, $R_7$, $R_8$, $R_9$, $R_{10}$, $R_{11}$, $R_{12}$, n, m, q, r, p, and $Ar_1$ are as described herein.

$R_4$ can be —$CHR_5CO_2H$, —$CH_2$-tetrazole, or an acid mimic. In certain embodiments, $R_4$ is unsubstituted $CH_2COOH$, substituted $CH_2COOH$ or —$CH_2$-tetrazole. In some embodiments, for example $R_4$ is unsubstituted $CH_2COOH$, $CH_2COOH$ wherein the methylene group is substituted with benzyl, or —$CH_2$-tetrazole. In such embodiments, Ar, $R_1$, $R_2$, $R_3$, $R_5$, $R_6$, $R_7$, $R_8$, $R_9$, $R_{10}$, $R_{11}$, $R_{12}$, n, m, q, r, p, and $Ar_1$ are as described herein.

For use in the present invention, $R_5$ can be hydrogen or benzyl, n can be 0 or 1, r can be from 0 to 6 and p can be from 0-3. In such embodiments, Ar, $R_1$, $R_2$, $R_3$, $R_4$, $R_6$, $R_7$, $R_8$, $R_9$, $R_{10}$, $R_{11}$, $R_{12}$, n, m, q, r, p, and $Ar_1$ are as described herein.

$R_6$, $R_7$, $R_8$, $R_9$, $R_{10}$ and $R_{12}$ can be, independently, hydrogen, $C_1$-$C_6$ alkyl, $C_1$-$C_6$ alkoxy, hydroxy, $C_3$-$C_6$ cycloalkyl, halogen, $C_1$-$C_3$ perfluoroalkyl, $C_1$-$C_3$ perfluoroalkoxy, —$(CH_2)_q$-phenyl wherein the phenyl ring is optionally substituted with alkyl, alkoxy, halogen, trifluoromethyl, trifluoromethoxy, or —(CH$_2$)$_q$-phenyl, or —O(CH$_2$)$_q$-phenyl wherein the phenyl ring is optionally substituted with alkyl, alkoxy, halogen, trifluoromethyl, trifluoromethoxy, or —(CH$_2$)$_q$-phenyl and R$_{11}$ can be hydrogen, C$_1$-C$_6$ alkyl, C$_3$-C$_6$ cycloalkyl, —(CH$_2$)$_q$—C$_3$-C$_6$ cycloalkyl, or —(CH$_2$)$_q$-phenyl wherein the phenyl ring is optionally substituted with alkyl, alkoxy, halogen, trifluoromethyl, trifluoromethoxy, or phenyl.

In certain embodiments, R$_6$ is hydrogen or alkyl. For example, in some embodiments, R$_6$ is butyl. In such embodiments, R$_1$, R$_2$, R$_3$, R$_4$, R$_5$, n, r, p, and q are as described herein.

In certain embodiments, R$_7$ is hydrogen and R$_8$ is hydrogen or halogen. For example, R$_7$ is hydrogen and R$_8$ is hydrogen, chlorine, or fluorine. In other embodiments, R$_7$ is hydrogen and R$_8$ is unsubstituted aryl or aryl substituted with alkyl. For example, R$_7$ is hydrogen and R$_8$ is phenyl or phenyl substituted with propyl. In even other embodiments, R$_7$ is hydrogen and R$_8$ is halogen, unsubstituted phenyl, or phenyl substituted with halogen or CF$_3$. In such embodiments, R$_1$, R$_2$, R$_3$, R$_4$, R$_5$, R$_9$, R$_{12}$, n, r, p, m, and q are as described herein.

In certain embodiments, R$_9$ is hydrogen, perfluoroalkyl, or alkyl. For example, in some embodiments, R$_9$ is CF$_3$ or propyl. In such embodiments, R$_1$, R$_2$, R$_3$, R$_4$, R$_5$, R$_7$, R$_8$, n, r, p, and q are as described herein.

In certain embodiments, R$_{10}$ is hydrogen, and R$_{11}$ is alkyl or aralkyl. For example, in some embodiments, R$_{10}$ is hydrogen, and R$_{11}$ is methyl or unsubstituted benzyl. In such embodiments, R$_1$, R$_2$, R$_3$, R$_4$, R$_5$, R$_{11}$, n, r, p, and q are as described herein.

In certain embodiments, R$_{12}$ is hydrogen, alkyl, or perfluoroalkyl. For example, in some embodiments, R$_{12}$ is hydrogen, butyl, or CF$_3$. In such embodiments, R$_1$, R$_2$, R$_3$, R$_4$, R$_5$, n, r, p, and q are as described herein.

For use in the present invention, Ar can be substituted or unsubstituted phenyl, naphthyl, furanyl, thiophenyl, benzofuranyl, benzothiophenyl, indolyl, pyrazolyl, oxazolyl, fluorenyl, phenylcycloalkyl, or dihydroindenyl. In certain embodiments, Ar is a biphenyl ring, fluorenyl, or thiophene, optionally substituted with substituted phenyl, furanyl optionally substituted with substituted pyrazole, naphthyl optionally substituted with —O-alkyl, furanyl optionally substituted by phenyl, pyrazole substituted by phenyl, or benzothiophene optionally substituted with halogen. In such embodiments, R$_1$, R$_2$, R$_3$, R$_4$, R$_5$, n, r, and p are as described herein.

In other embodiments, Ar is naphthyl, furanyl, thiophenyl, benzofuranyl, benzothiophenyl, indolyl, pyrazolyl, oxazolyl, fluorenyl, phenylcycloalkyl, or dihydroindenyl. In such embodiments, R$_1$, R$_2$, R$_3$, R$_4$, R$_5$, n, r, and p are as described herein.

In yet other embodiments, Ar is substituted phenyl, naphthyl, furanyl, thiophenyl, benzofuranyl, benzothiophenyl, indolyl, pyrazolyl, oxazolyl, fluorenyl, phenylcycloalkyl, or dihydroindenyl. In such embodiments, R$_1$, R$_2$, R$_3$, R$_4$, R$_5$, n, r, and p are as described herein.

Exemplary 4'-aryl-amido-biphenyl-4(3)-yloxy-acids and 4'-aryl-amidomethyl-biphenyl-4(3)-yloxy-c of the present invention include, but are not limited to, ({4'-[({[1-phenyl-5-(trifluoromethyl)-1H-pyrazol-4-yl]carbonyl}amino)methyl][1,1'-biphenyl]-4-yl}oxy)acetic acid or a pharmaceutically acceptable salt thereof; ({4'-[({[1-phenyl-5-propyl-1H-pyrazol-4-yl]carbonyl}amino)methyl][1,1'-biphenyl]-4-yl}oxy)acetic acid or a pharmaceutically acceptable salt thereof; {[3-bromo-4'-({[(1-phenyl-5-propyl-1H-pyrazol-4-yl]carbonyl}amino}methyl)[1,1'-biphenyl]-4-yl]oxy}acetic acid or a pharmaceutically acceptable salt thereof; {[3-bromo-4'-({[(2-butyl-1-benzofuran-3-yl)carbonyl]amino}methyl)[1, 1'-biphenyl]-4-yl]oxy}acetic acid or a pharmaceutically acceptable salt thereof; N-{[3'-bromo-4'-(1H-tetraazol-5-ylmethoxy)[1,1'-biphenyl]-4-yl]methyl}-1-phenyl-5-propyl-1H-pyrazole-4-carboxamide or a pharmaceutically acceptable salt thereof; N-{[3'-bromo-4'-(H-tetraazol-5-ylmethoxy)-1,1'-biphenyl-4-yl]methyl}-2-butyl-N-methyl-1-benzofuran-3-carboxamide or a pharmaceutically acceptable salt thereof; [(3-bromo-4'-{[[(2-butyl-1-benzofuran-3-yl)carbonyl](methyl)amino]methyl}-1,1'-biphenyl-4-yl)oxy]acetic acid or a pharmaceutically acceptable salt thereof; 2-[(3-bromo-4'-{[[(2-butyl-1-benzofuran-3-yl)carbonyl](methyl)amino]methyl}-1,1'-biphenyl-4-yl)oxy]-3-phenylpropanoic or a pharmaceutically acceptable salt thereof; N-{[3'-bromo-4'-(1H-tetraazol-5-ylmethoxy)-1,1'-biphenyl-4-yl]methyl}-N,1-dimethyl-1H-indole-3-carboxamide or a pharmaceutically acceptable salt thereof; 1-Benzyl-N-{[3'-bromo-4'-(1H-tetraazol-5-ylmethoxy)-1,1'-biphenyl-4-yl]methyl}-N-methyl-1H-indole-3-carboxamide or a pharmaceutically acceptable salt thereof; N-benzyl-N-{[3'-bromo-4'-(1H-tetraazol-5-ylmethoxy)-1,1'-biphenyl-4-yl]methyl}-2-butyl-1-benzofuran-3-carboxamide or a pharmaceutically acceptable salt thereof; N-benzyl-N-{[3'-bromo-4'-(1H-tetraazol-5-ylmethoxy)-1,1'-biphenyl-4-yl]methyl}-1-methyl-1H-indole-3-carboxamide or a pharmaceutically acceptable salt thereof; [(4'-{[(2-butyl-1-benzofuran-3-yl)carbonyl]amino}[1,1'-biphenyl]-4-yl)oxy]acetic acid or a pharmaceutically acceptable salt thereof; 2-butyl-N-[4'-(1H-tetraazol-5-ylmethoxy)[1,1'-biphenyl]-4-yl]-1-benzofuran-3-carboxamide or a pharmaceutically acceptable salt thereof; 3-phenyl-2-[(4'-{[(4'-propyl-1,1'-biphenyl-4-yl)carbonyl]amino}-1,1'-biphenyl-4-yl)oxy]propanoic acid or a pharmaceutically acceptable salt thereof; 2-[(4'-{[5-(4-chlorophenyl)-2-furoyl]amino}-1,1'-biphenyl-4-yl)oxy]-3-phenylpropanoic acid or a pharmaceutically acceptable salt thereof; {[4'-({[1-(4-chlorophenyl)cyclopentyl]carbonyl}amino)-1,1'-biphenyl-4-yl]oxy}acetic acid or a pharmaceutically acceptable salt thereof; {[4'-({[1-(3-fluorophenyl)cyclopentyl]carbonyl}amino)-1,1'-biphenyl-4-yl]oxy}acetic acid or a pharmaceutically acceptable salt thereof; 2-({4'-[(9H-fluoren-4-ylcarbonyl)amino]-1,1'-biphenyl-3-yl}oxy)-3-phenylpropanoic acid or a pharmaceutically acceptable salt thereof; 3-phenyl-2-[(4'-{[(1-phenylcyclopentyl)carbonyl]amino}-1,1'-biphenyl-3-yl)oxy]propanoic acid or a pharmaceutically acceptable salt thereof; 2-{[4'-({[1-(4-chlorophenyl)cyclopentyl]carbonyl}amino)-1,1'-biphenyl-3-yl]oxy}-3-phenylpropanoic acid or a pharmaceutically acceptable salt thereof; 2-{[4'-({[1-(4-chlorophenyl)-5-propyl-1H-pyrazol-4-yl]carbonyl}amino)-1,1'-biphenyl-3-yl]oxy}-3-phenylpropanoic acid or a pharmaceutically acceptable salt thereof; 2-{[4'-({[5-(benzyloxy)-1H-indol-2-yl]carbonyl}amino)-1,1'-biphenyl-3-yl]oxy}-3-phenylpropanoic acid or a pharmaceutically acceptable salt thereof; 2-{[4'-({[1-(4-chlorophenyl)cyclopropyl]carbonyl}amino)-1,1'-biphenyl-3-yl]oxy}-3-phenylpropanoic acid or a pharmaceutically acceptable salt thereof; 2-{[4'-({[1-(3-fluorophenyl)cyclopentyl]carbonyl}amino)-1,1'-biphenyl-3-yl]oxy}-3-phenylpropanoic acid or a pharmaceutically acceptable salt thereof; 3-phenyl-2-[(4'-{[(1-phenylcyclopentyl)carbonyl]amino}-1,1'-biphenyl-4-yl)oxy]propanoic acid or a pharmaceutically acceptable salt thereof; 3-phenyl-2-[(4'-{[(1-phenylcyclopropyl)carbonyl]amino}-1,1'-biphenyl-4-yl)oxy]propanoic acid or a pharmaceutically acceptable salt thereof; 2-{[4'-({[1-(4-chlorophenyl)cyclopropyl]carbonyl}amino)-1,1'-biphenyl-4-yl]oxy}-3-phenylpropanoic acid or a pharmaceutically acceptable salt thereof; 2-{[4'-({[1-(3-fluorophenyl)cyclopentyl]carbonyl}amino)-1,1'-biphenyl-4-yl]oxy}-3-phenylpropanoic acid or a pharmaceutically acceptable salt thereof; {[4'-({[1-(4-chlorophenyl)cyclobutyl]carbonyl}amino)-1,1'-biphenyl-4-yl]oxy}acetic acid or a pharmaceutically acceptable salt thereof; [(4'-{[5-(1,1-biphenyl-4-yl)-2-(trifluoromethyl)-3-furoyl]amino}-1,1'-biphenyl-4-yl)oxy]acetic acid or a pharmaceutically acceptable salt thereof; 2-({4'-[(4-phenoxybenzoyl)amino]-1,1'-biphenyl-3-yl}oxy)-3-phenylpropanoic acid or a pharmaceutically acceptable salt thereof; 2-{[4'-({[5-(4-chlorophenyl)thien-2-yl]carbonyl}amino)-1,1'-biphenyl-3-yl]oxy}-3-phenylpropanoic acid or a pharmaceutically acceptable salt thereof; 2-{[4'-({[1-(4-chlorophenyl)cyclobutyl]carbonyl}amino)-1,1'-biphenyl-3-yl]oxy}-3-phenylpropanoic acid or a pharmaceutically acceptable salt thereof; 2-[(4'-{[5-(2-chlorophenyl)-2-(trifluoromethyl)-3-furoyl]amino}-1,1'-biphenyl-3-yl)oxy]-3-phenylpropanoic acid or a pharmaceutically acceptable salt thereof; 2-[(4'-{[(2-butyl-1-benzofuran-3-yl)carbonyl]amino}-1,1'-biphenyl-3-yl)oxy]-3-phenylpropanoic acid or a pharmaceutically acceptable salt thereof; 2-[(4'-{[5-(1,1'-biphenyl-4-yl)-2-(trifluoromethyl)-3-furoyl]amino}-1,1'-biphenyl-3-yl)oxy]-3-phenylpropanoic acid or a pharmaceutically acceptable salt thereof; 3-phenyl-2-{[4'-(2-(trifluoromethyl)-5-[4-(trifluoromethyl)phenyl]-3-furoyl}amino)-1,1'-biphenyl-3-yl]oxy}propanoic acid or a pharmaceutically acceptable salt thereof; 2-{[4'-({5-[(4-bromo-3,5-dimethyl-1H-pyrazol-1-yl)methyl]-2-furoyl}amino)-1,1'-biphenyl-3-yl]oxy}-3-phenylpropanoic acid or a pharmaceutically acceptable salt thereof; 2-({4'-[(4-phenoxybenzoyl)amino]-1,1'-biphenyl-4-yl}oxy)-3-phenylpropanoic acid or a pharmaceutically acceptable salt thereof; 2-{[4'-({[5-(4-chlorophenyl)thien-2-yl]carbonyl}amino)-1,1'-biphenyl-4-yl]oxy}-3-phenylpropanoic acid or a pharmaceutically acceptable salt thereof; 2-{[4'-({[1-(4-chlorophenyl)cyclobutyl]carbonyl}amino)-1,1'-biphenyl-4-yl]oxy}-3-phenylpropanoic acid or a pharmaceutically acceptable salt thereof; 2-[(4'-{[5-(2-chlorophenyl)-2-(trifluoromethyl)-3-furoyl]amino}-1,1'-biphenyl-4-yl)oxy]-3-phenylpropanoic acid or a pharmaceutically acceptable salt thereof; 2-[(4'-{[(2-butyl-1-benzofuran-3-yl)carbonyl]amino}-1,1'-biphenyl-4-yl)oxy]-3-phenylpropanoic acid or a pharmaceutically acceptable salt thereof; 3-phenyl-2-{[4'-({2-(trifluoromethyl)-5-[4-(trifluoromethyl)phenyl]-3-furoyl}amino)-1,1'-biphenyl-4-yl]oxy}propanoic acid or a pharmaceutically acceptable salt thereof; 2-{[4'-({[1-(4-chlorophenyl)cyclohexyl]carbonyl}amino)-1,1'-biphenyl-3-yl]oxy}-3-phenylpropanoic acid or a pharmaceutically acceptable salt thereof; 2-{[4'-({[1-(4-chlorophenyl)cyclopentyl]carbonyl}amino)-1,1'-biphenyl-4-yl]oxy}-3-phenylpropanoic acid or a pharmaceutically acceptable salt thereof; 3-phenyl-2-[(4'-{[(1-phenylcyclopropyl)carbonyl]amino}-1,1'-biphenyl-3-yl)oxy]propanoic acid or a pharmaceutically acceptable salt thereof; 3-phenyl-2-[(4'-{[(2,2,5,7-tetramethyl-1-oxo-2,3-dihydro-1H-inden-4-yl)carbonyl]amino}-1,1'-biphenyl-3-yl)oxy]propanoic acid or a pharmaceutically acceptable salt thereof; 2-{[4'-(2-naphthoylamino)-1,1'-biphenyl-4-yl]oxy}-3-phenylpropanoic acid or a pharmaceutically acceptable salt thereof; 2-({4'-[(6-butoxy-2-naphthoyl)amino]-1,1'-biphenyl-4-yl}oxy)-3-phenylpropanoic acid or a pharmaceutically acceptable salt thereof; 2-[(4'-{[(3-chloro-1-benzothien-2-yl)carbonyl]amino}-1,1'-biphenyl-4-yl)oxy]-3-phenylpropanoic acid or a pharmaceutically acceptable salt thereof.

The present invention also provides compositions comprising the substituted biphenyloxy acids of the present invention, including those compounds of formulas 1-7 or a stereoisomer or pharmaceutically acceptable salt thereof, and one or more pharmaceutically acceptable carriers, excipients, or diluents.

Such compositions include pharmaceutical compositions for treating or controlling disease states or conditions associated with increased PAI-1 activity. In certain embodiments, the compositions comprise mixtures of one or more substituted biphenyloxy acids.

Certain of the compounds of formulas 1-7 contain stereogenic carbon atoms or other chiral elements and thus give rise to stereoisomers, including enantiomers and diastereomers. The present invention includes all of the stereoisomers of formulas 1-7, as well as mixtures of the stereoisomers. Throughout this application, the name of the product, where the absolute configuration of an asymmetric center is not indicated, is intended to embrace the individual stereoisomers as well as mixtures of stereoisomers.

Where an enantiomer is preferred, it can, in some embodiments, be provided substantially free of the corresponding enantiomer. Thus, an enantiomer substantially free of the corresponding enantiomer refers to a compound that is isolated or separated via separation techniques or prepared free of the corresponding enantiomer. "Substantially free," as used herein, means that the compound is made up of a significantly greater proportion of one enantiomer. In preferred embodiments, the compound is made up of at least about 90% by weight of a preferred enantiomer. In other embodiments of the invention, the compound is made up of at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein. Methods for the preparation of preferred enantiomers are described, for example, in Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); and Wilen, S. H. Tables of Resolving Agents and Optical Resolutions p. 268 (E. L. Eliel, Ed., Univ. of Notre Dame Press, Notre Dame, Ind. 1972).

Exemplary salt forms of the compounds herein include, but are not limited to, sodium salts and potassium salts. Other exemplary salt forms of these compounds include, but are not limited to, those formed with pharmaceutically acceptable inorganic and organic bases or acids known in the art. The acids include, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable aids when a compound of this invention contains a basic moiety. Salt forms prepared using inorganic bases include hydroxides, carbonates or bicarbonates of the therapeutically acceptable alkali metals or alkaline earth metals, such as sodium potassium, magnesium, calcium and the like. Acceptable organic bases include amines, such as benzylamine, mono-, di- and trialkylamines, preferably those having alkyl groups of from 1 to 6 carbon atoms, more preferably 1 to 3 carbon atoms, such as methylamine, dimethylamine, trimethylamine, ethylamine, diethylamine, triethylamine, mono-, di-, and triethanolamine. Exemplary salts also include alkylene diamines containing up to 6 carbon atoms, such as hexamethylenediamine; cyclic saturated or unsaturated bases containing up to 6 carbon atoms, including pyrrolidine, piperidine, morpholine, piperazine and their N-alkyl and N-hydroxyalkyl derivatives, such as N-methyl-morpholine and N-(2-hyroxyethyl)-piperidine, or pyridine. Quaternary salts can also be formed, such as tetralkyl forms, such as tetramethyl forms, alkyl-alkanol forms, such as methyl-triethanol or trimethyl-monoethanol forms, and cyclic ammonium salt forms, such as N-methylpyridinium, N-methyl-N-(2-hydroxyethyl)-morpholinium, N,N-dimethylmorpholinium, N-methyl-N-(2-hydroxyethyl)-morpholinium, or N,N-dimethyl-piperidinium salt forms. These salt forms can be prepared using the acidic compound(s) of Formulas 1-7 and procedures known in the art.

Exemplary ester forms of the compounds of this invention include, but are not limited to, straight chain alkyl esters having from 1 to 6 carbon atoms or branched chain alkyl groups containing 1 to 6 carbon atoms, including methyl, ethyl, propyl, butyl, 2-methylpropyl and 1,1-dimethylethyl esters, cycloalkyl esters, alkylaryl esters, benzyl esters, and the like. Other exemplary esters include, but are not limited to, those of the formula —$COOR_{13}$ wherein $R_{13}$ is selected from the formula:

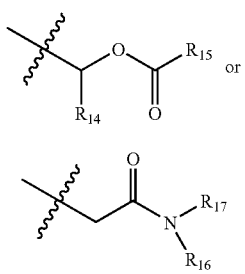

wherein $R_{14}$, $R_{15}$, $R_{16}$, and $R_{17}$ are independently selected from hydrogen, alkyl of from 1 to 10 carbon atoms, aryl of 6 to 12 carbon atoms, arylalkyl of from 6 to 12 carbon atoms; heteroaryl or alkylheteroaryl wherein the heteroaryl ring is bound by an alkyl chain of from 1 to 6 carbon atoms.

Acids and acid mimics, according to the invention, are defined as proton or hydrogen donating groups. Exemplary acid mimics or mimetics of the present invention include pharmaceutically useful carboxylic acids and acid mimics or mimetics known in the art, such as those described in R. Silverman, The Organic Chemistry of Drug Design and Drug Action, Academic Press (1992) and others. Exemplary acid mimics or mimetics include, but are not limited to the following examples, tetrazole, tetronic acid or groups having the formula:

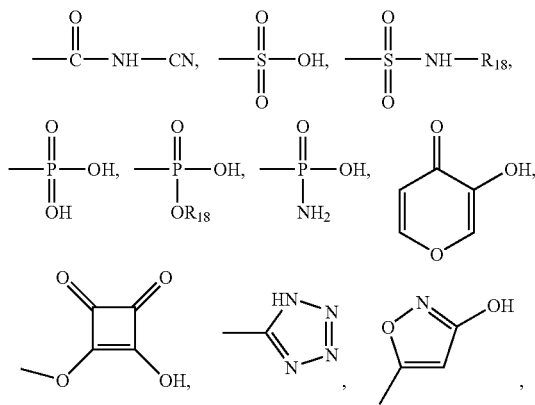

wherein $R_{18}$ is $C_1$-$C_6$ alkyl, $C_2$-$C_6$ alkenyl, $C_3$-$C_6$ cycloalkyl, —$CH_2$—($C_3$-$C_6$ cycloalkyl), $C_3$-$C_6$ cycloalkenyl, —$CH_2$—($C_3$-$C_6$ cycloalkenyl), optionally substituted aryl or heteroaryl groups or optionally substituted —$C_1$-$C_6$ alkyl-aryl or —$C_1$-$C_6$ alkyl-heteroaryl, with the aryl and heteroaryl groups as defined herein. In some embodiments $R_{18}$ is aralkyl or heteroarylalkyl.

Preferred compounds of the present invention inhibit PAI-1 activity. Accordingly, the compounds can be used for the treatment, including prevention, inhibition, and/or amelioration of PAI-1 related disorders in a subject, including, for example, in the treatment of noninsulin dependent diabetes mellitus, in the treatment of cardiovascular disease, and in the treatment of thrombotic events associated with coronary artery and cerebrovascular disease. Using the methods of the present invention, a skilled medical practitioner will know how to administer the compounds of the present invention, including those represented by formulas 1-7, to a subject suffering from any of the diseases associated with increased PAI-1 activity or expression, e.g., diabetes or cardiovascular disease, in order to effect treatment for that disease.

In one exemplary embodiment, the compounds of the present invention are administered to a subject in order to treat disease processes involving thrombotic and prothrombotic states which include, but are not limited to, formation of atherosclerotic plaques, venous and arterial thrombosis, myocardial ischemia, atrial fibrillation, deep vein thrombosis, coagulation syndromes, pulmonary thrombosis, cerebral thrombosis, thromboembolic complications of surgery (such as joint or hip replacement), and peripheral arterial occlusion.

Any disease or condition that is associated with increased PAI-1 activity or expression in a subject can be treated using the compounds of the present invention. Exemplary diseases and conditions include stroke, e.g., stroke associated with or resulting from atrial fibrillation; diseases associated with extracellular matrix accumulation including, but not limited to, renal fibrosis, chronic obstructive pulmonary disease, polycystic ovary syndrome, restenosis, renovascular disease, and organ transplant rejection; diseases associated with neoangiogenesis, including, but not limited to, diabetic retinopathy; Alzheimer's disease, e.g., by increasing or normalizing levels of plasmin concentration in a subject; myelofibrosis with myeloid metaplasia, e.g., by regulating stromal cell hyperplasia and increases in extracellular matrix proteins; diabetic nephropathy and renal dialysis associated with nephropathy; malignancies or cancers, including, but not limited to, leukemia, breast cancer and ovarian cancer; tumors, including, but not limited to, liposarcomas and epithelial tumors; septicemia; obesity; insulin resistance; proliferative diseases, including, but not limited to, psoriasis; conditions associated with abnormal coagulation homeostasis; low grade vascular inflammation; cerebrovascular diseases; hypertension; dementia; osteoporosis; arthritis; respiratory diseases, such as asthma; heart failure; arrhythmia; angina, including, but not limited to, angina pectoris; atherosclerosis and sequelae; kidney failure; multiple sclerosis; osteoporosis; osteopenia; dementia; peripheral vascular disease; peripheral arterial disease; acute vascular syndromes; microvascular diseases including, but not limited to, nephropathy, neuropathy, retinopathy and nephrotic syndrome; hypertension; Type I and II diabetes and related diseases; hyperglycemia; hyperinsulinemia; malignant lesions; premalignant lesions; gastrointestinal malignancies; coronary heart disease, including, but not limited to, primary and secondary prevention of myocardial infarction, stable and unstable angina, primary prevention of coronary events, and secondary prevention of cardiovascular events; and inflammatory diseases, including, but not limited to, septic shock and the vascular damage associated with infections.

The compounds of the present invention can also be administered to a subject in combination with a second therapeutic agent, including, but not limited to, prothrombolytic, fibrinolytic, and anticoagulant agents, or in conjunction with other therapies, for example, protease inhibitor-containing highly active antiretroviral therapy (HAART) for the treatment of diseases which originate from fibrinolytic impairment and hyper-coagulability of HIV-1 infected patients. In certain embodiments, the compounds of the present invention can be administered in conjunction with and/or following processes or procedures involving maintaining blood vessel patency, including, but not limited to, vascular surgery, vascular graft and stent patency, organ, tissue and cell implantation and transplantation. The compounds of the present invention can also be used for the treatment of blood and blood products used in dialysis, blood storage in the fluid phase, especially ex vivo platelet aggregation. The compounds of the present invention can also be administered to a subject as a hormone replacement agent or to reduce inflammatory markers or C-reactive protein. The compounds can be administered to improve coagulation homeostasis, to improve endothelial function, or as a topical application for wound healing, e.g., the prevention of scarring. The compounds of the present invention can be administered to a subject in order to reduce the risk of undergoing a myocardial revascularization procedure. The present compounds can also be added to human plasma during the analysis of blood chemistry in hospital settings to determine the fibrinolytic capacity thereof. In certain embodiments, the compounds of the present invention can be used as imaging agents for the identification of metastatic cancers.

C. Synthesis of Substituted Biphenyloxy Acids

Compounds of the present invention can be prepared by those skilled in the art of organic synthesis employing conventional methods that utilize readily available reagents and starting materials. Representative compounds of the present invention can be prepared using the following synthetic schemes. The skilled practitioner will know how to make use of variants of these process steps, which in themselves are well known in the art. In the following reaction schemes, the substituents are selected from the groups defined above.

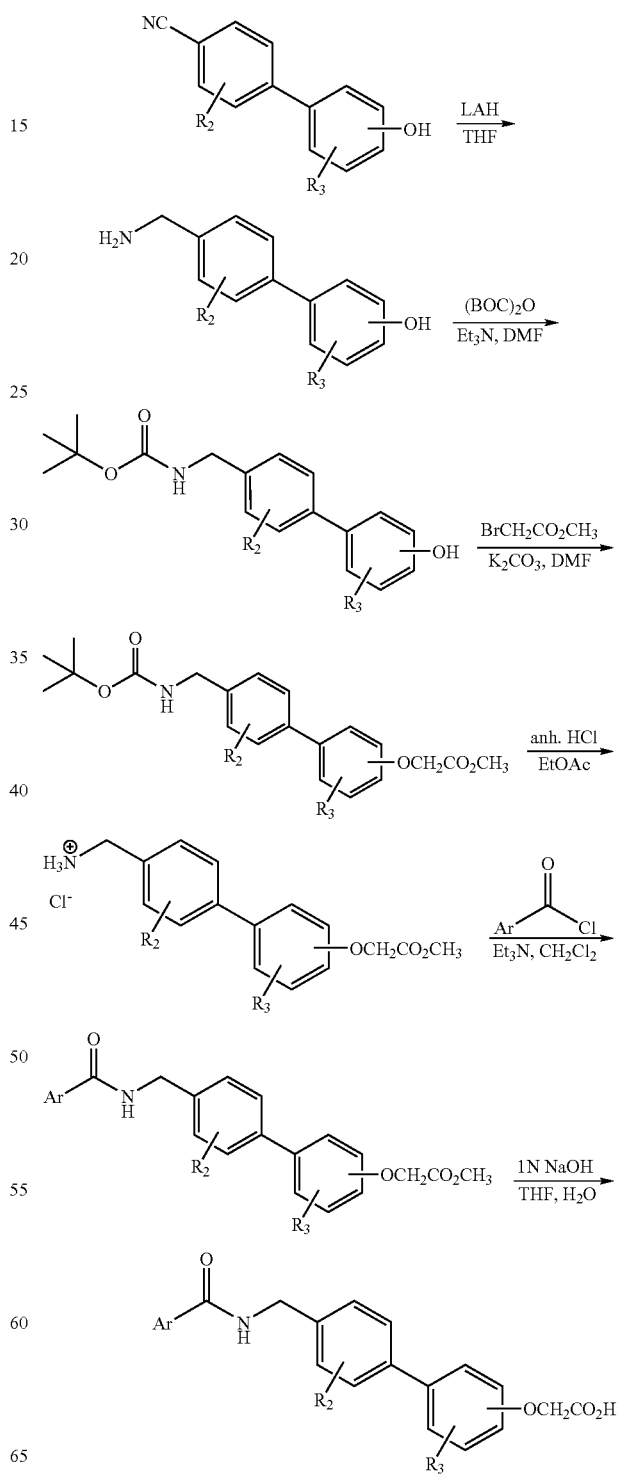

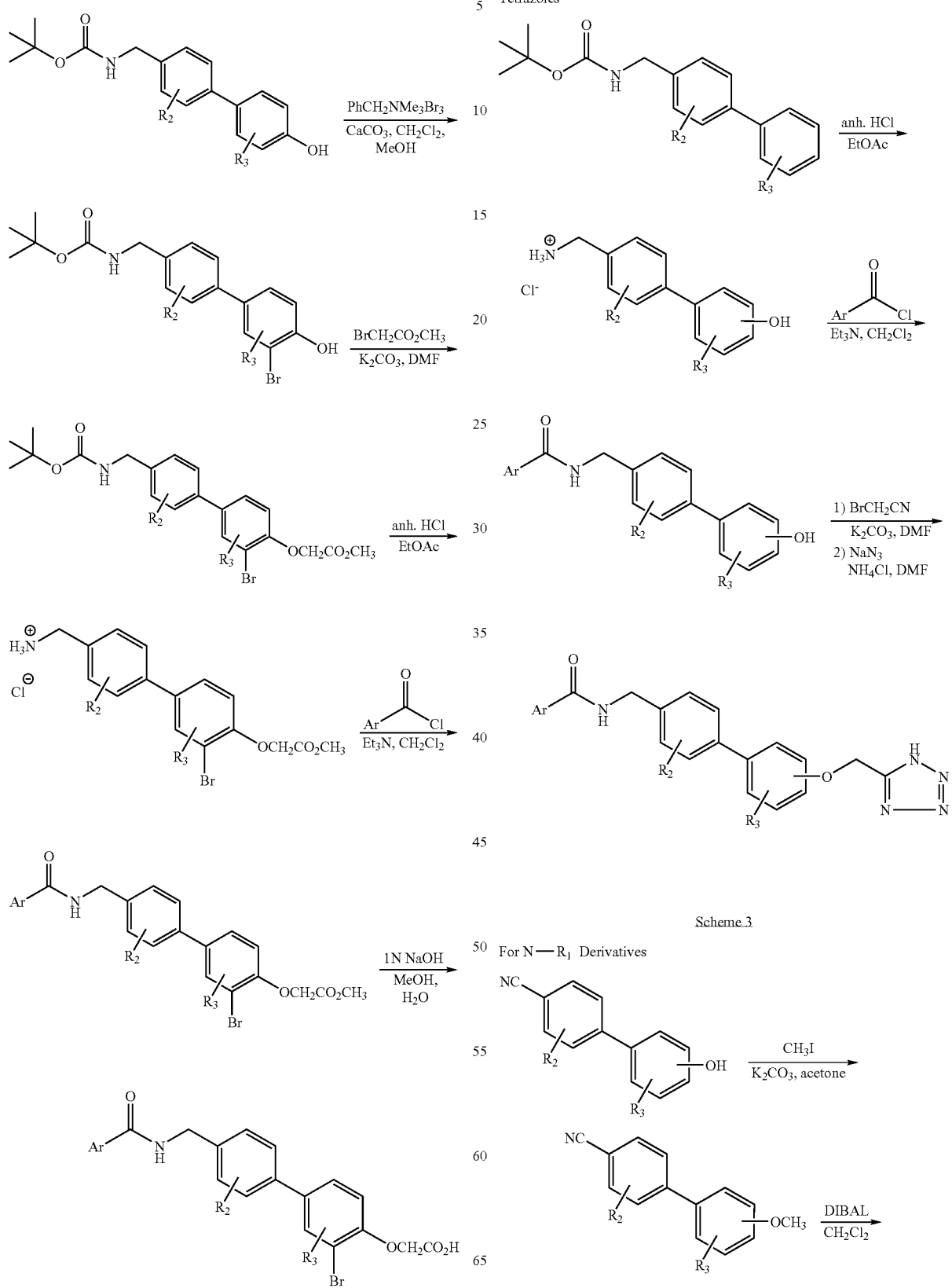

-continued

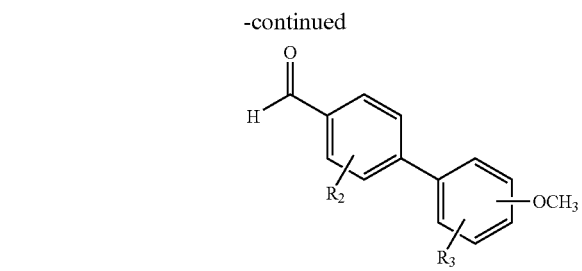

Bromine Derivatives

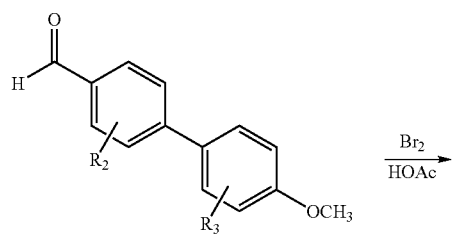

$$\xrightarrow{\text{Br}_2}{\text{HOAc}}$$

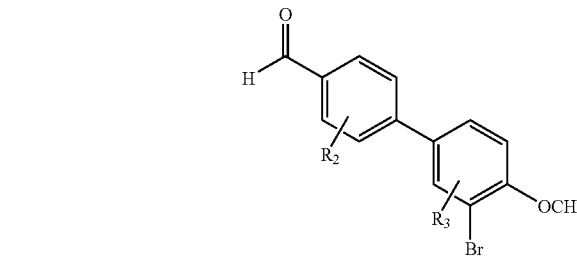

$$\xrightarrow[\text{2) NaBH}_4\text{, abs. EtOH}]{\text{1) R}_1\text{NH}_2\;\;\text{CH}_2\text{Cl}_2\text{, anh. MgSO}_4}$$

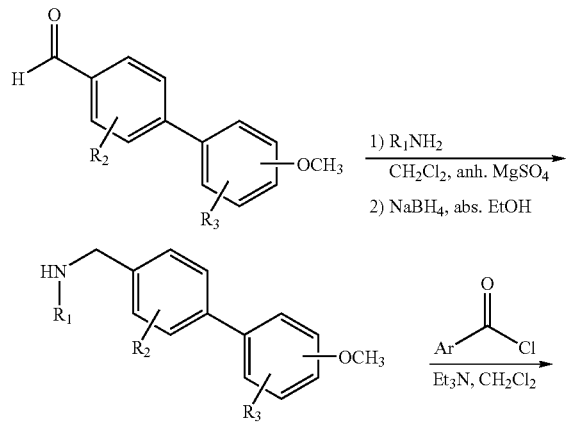

$$\xrightarrow[\text{Et}_3\text{N, CH}_2\text{Cl}_2]{\text{Ar}\;\overset{\text{O}}{\text{C}}\text{Cl}}$$

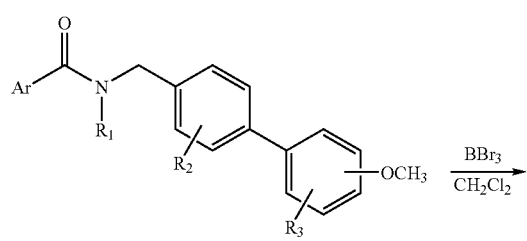

$$\xrightarrow{\text{BBr}_3}{\text{CH}_2\text{Cl}_2}$$

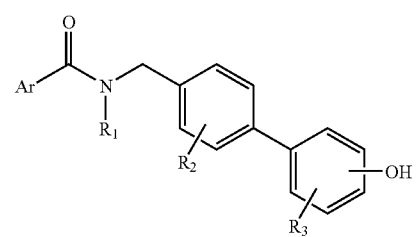

For Tetrazoles

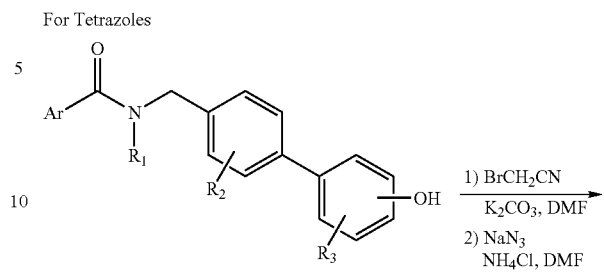

$$\xrightarrow[\text{2) NaN}_3\;\;\text{NH}_4\text{Cl, DMF}]{\text{1) BrCH}_2\text{CN}\;\;\text{K}_2\text{CO}_3\text{, DMF}}$$

For Acetates

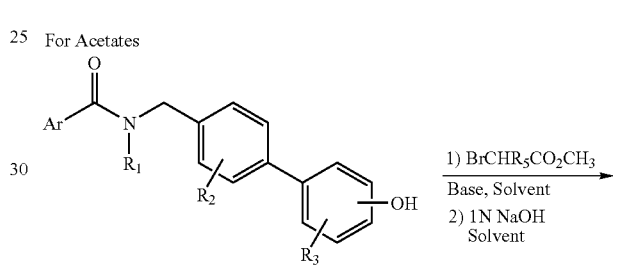

$$\xrightarrow[\text{2) 1N NaOH Solvent}]{\text{1) BrCHR}_5\text{CO}_2\text{CH}_3\;\;\text{Base, Solvent}}$$

Scheme 4

Acetates

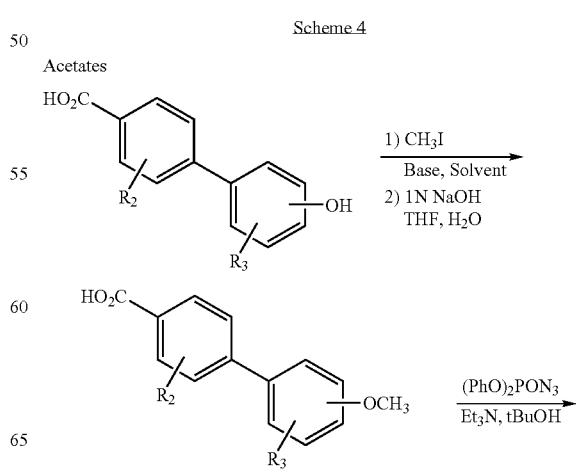

$$\xrightarrow[\text{2) 1N NaOH THF, H}_2\text{O}]{\text{1) CH}_3\text{I Base, Solvent}}$$

$$\xrightarrow{\text{(PhO)}_2\text{PON}_3}{\text{Et}_3\text{N, tBuOH}}$$

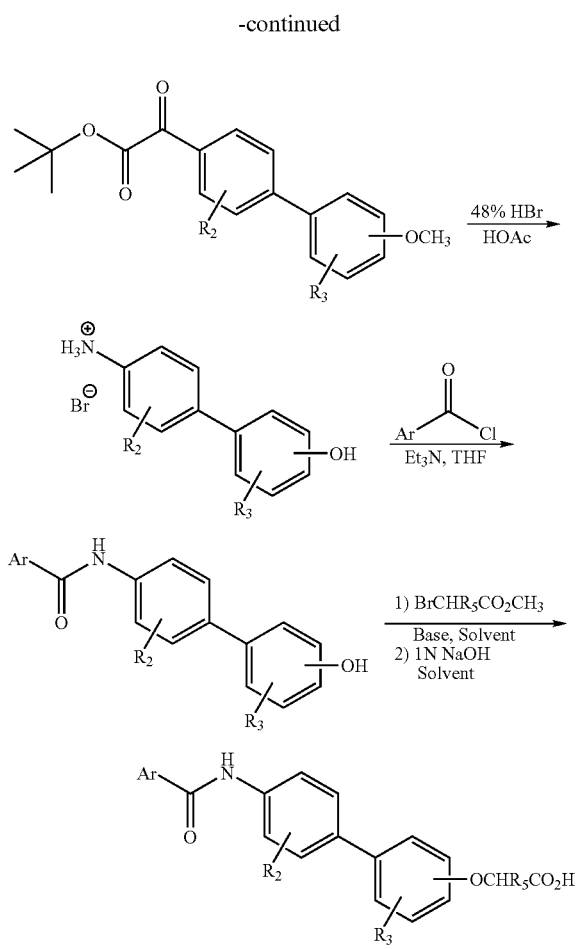
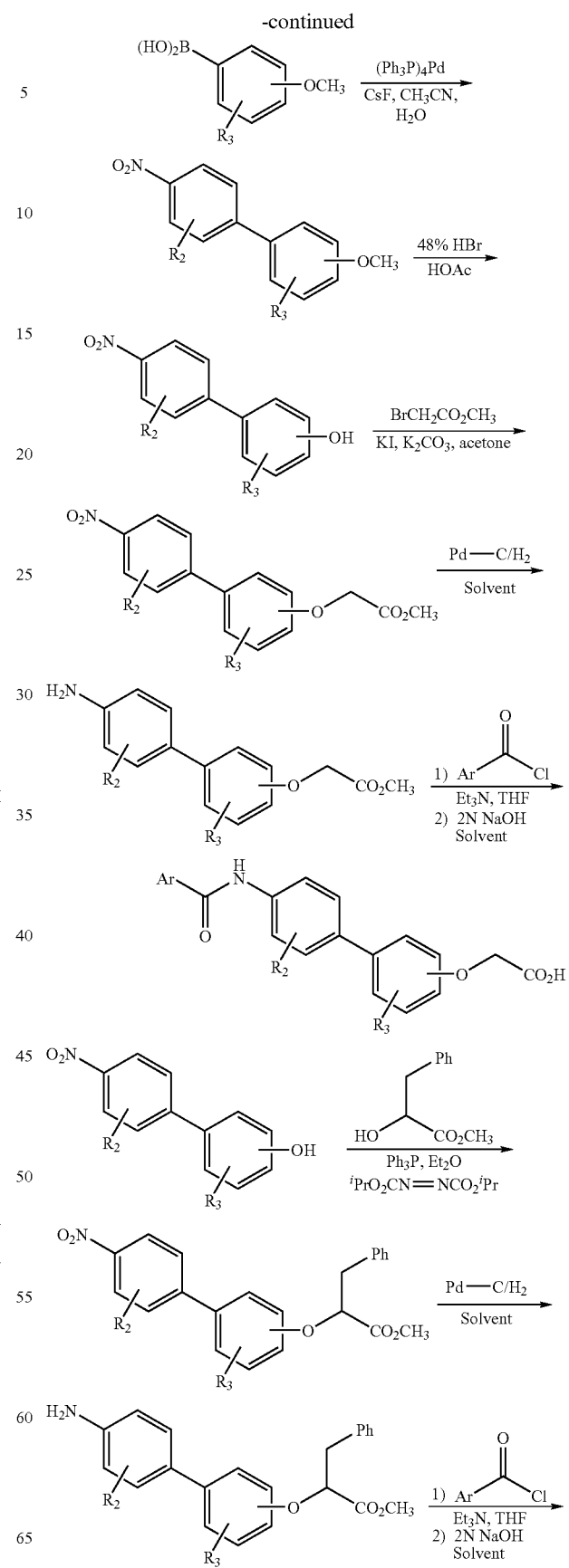
Scheme 5
Alternate Route to Aniline Derivatives
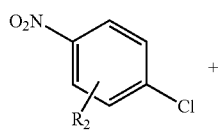

-continued

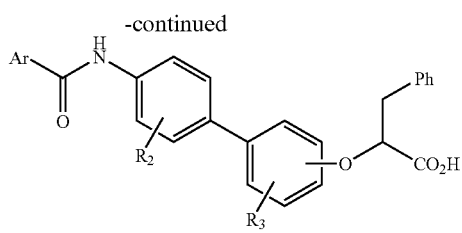

D. Substituted Biphenyloxy Acids as Pharmaceutical Compositions

The present invention provides substituted biphenyloxy acids as pharmaceuticals. In a preferred embodiment, the compounds of the present invention are formulated as pharmaceuticals to treat diseases associated with increased PAI-1 activity, e.g., by inhibiting PAI-1 activity in a subject.

In general, the compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection). Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: Remington's Pharmaceutical Sciences, 17th ed., Mack Publishing Company, Easton Pa., 1985. Suitable liquid carriers, especially for injectable solutions, include water, aqueous saline solution, aqueous dextrose solution, and glycols. In some embodiments of the present invention, substituted biphenyloxy acids suitable for use in the practice of this invention will be administered either singly or in combination with at least one other compound of this invention. Substituted biphenyloxy acids suitable for use in the practice of the present invention can also be administered with at least one other conventional therapeutic agent for the disease being treated.

Aqueous suspensions of the invention can contain substituted biphenyloxy acids in admixture with excipients suitable for the manufacture of aqueous suspensions. Such excipients can include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions can be formulated by suspending a substituted biphenyloxy acid in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of substituted biphenyloxy acids in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension.

This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol. The formulations of commends can be presented in unit-dose or multi-dose sealed containers, such as ampules and vials.

Injection solutions and suspensions can be prepared from sterile powders, granules, and tablets of the kind previously described.

Compounds suitable for use in the practice of this invention can be administered orally. The amount of a compound of the present invention in the composition can vary widely depending on the type of composition, size of a unit dosage, kind of excipients, and other factors well known to those of ordinary skill in the art. In general, the final composition can comprise from, for example, 0.000001 percent by weight (% w) to 10% w of the compound, preferably 0.00001% w to 1% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient. Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropyl-methyl-cellulose or sodium carboxymethylcellulose; and gums including arabic and tragacanth; as well as proteins such as gelatin and collagen. If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient which is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention, e.g., anti-atherosclerotic medicaments.

In another embodiment, the compounds of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compound into the target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

In other cases, the preferred preparation can be a lyophilized powder which may contain, for example, any or all of the following: 1 mM-50 mM histidine, 0.1%-2% sucrose, 2%-7% mannitol, at a pH range of 4.5 to 5.5, that is combined with buffer prior to use.

A pharmaceutical composition of the invention can optionally contain, in addition to a substituted biphenyloxy acid, at least one other therapeutic agent useful in the treatment of a disease or condition associated with increased PAI-1 activity.

The pharmaceutical compositions are generally formulated as sterile, substantially isotonic and in full compliance with all Good Manufacturing Practice (GMP) regulations of the U.S. Food and Drug Administration E. Determining Dosage Regimens for Substituted Biphenyloxy Acids The present invention provides methods of inhibiting PAI-1 activity in a subject for the treatment of diseases and conditions associated with increased PAI-1 activity using substituted biphenyloxy acids.

For treatment purposes, the compositions or compounds disclosed herein can be administered to the subject in a single bolus delivery, via continuous delivery (e.g., continuous transdermal, mucosal, or intravenous delivery) over an extended time period, or in a repeated administration protocol (e.g., by an hourly, daily or weekly, repeated administration protocol). The pharmaceutical formulations of the present invention can be administered, for example, one or more times daily, 3 times per week, or weekly. In an exemplary embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to alleviate one or more symptoms or detectable conditions associated with increased PAI-1 activity. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response). In alternative embodiments, an "effective amount" or "therapeutically effective dose" of the biologically active agent(s) will simply inhibit or enhance one or more selected biological activity(ies) correlated with a disease or condition, as set forth above, for either therapeutic or diagnostic purposes.

The actual dosage of biologically active agents will of course vary according to factors such as the extent of exposure and particular status of the subject (e.g., the subject's age, size, fitness, extent of symptoms, susceptibility factors, etc), time and route of administration, as well as other drugs or treatments being administered concurrently. Dosage regimens can be adjusted to provide an optimum prophylactic or therapeutic response. By "therapeutically effective dose" herein is meant a dose that produces effects for which it is administered. More specifically, a therapeutically effective dose of the compound(s) of the invention preferably alleviates symptoms, complications, or biochemical indicia of diseases associated with increased PAI-1 activity. The exact dose will depend on the purpose of the treatment, and will be ascertainable by one skilled in the art using known techniques (see, e.g., Lieberman, Pharmaceutical Dosage Forms (Vols. 1-3, 1992); Lloyd, 1999, The Art, Science, and Technology of Pharmaceutical Compounding; and Pickar, 1999, Dosage Calculations). A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds.

In an exemplary embodiment of the present invention, unit dosage forms of the compounds are prepared for standard administration regimens. In this way, the composition can be subdivided readily into smaller doses at the physicians direction. For example, unit dosages can be made up in packeted powders, vials or ampoules and preferably in capsule or tablet form. The active compound present in these unit dosage forms of the composition can be present in an amount of, for example, from about one gram to about fifteen grams or more, for single or multiple daily administration, according to the particular need of the patient. By initiating the treatment regimen with a minimal daily dose of about one gram, the blood levels of PAI-1 and the patients symptomatic relief analysis can be used to determine whether a larger or smaller dose is indicated. Effective administration of the compounds of this invention can be given at an oral dose of, for example, from about 0.1 mg/kg/day to about 1,000 mg/kg/day. Preferably, administration will be from about 10/mg/kg/day to about 600 mg/kg/day, more preferably from about 25 to about 200 mg/kg/day, and even more preferably from about 50 mg/kg/day to about 100 mg/kg/day.

In certain embodiments, the present invention is directed to prodrugs of compounds of formulas 1-7. The term "prodrug," as used herein, means a compound that is convertible in vivo by metabolic means (e.g. by hydrolysis) to a compound of formulas 1-7.1 Various forms of prodrugs are known in the art such as those discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991), Bundgaard, et al., *Journal of Drug Delivery Reviews,* 8:1-38(1992), Bundgaard, *J. of Pharmaceutical Sciences,* 77:285 et seq. (1988); and Higuchi and Stella (eds.) Prodrugs as Novel Drug Delivery Systems, American Chemical Society (1975).

F. Kits

After a pharmaceutical comprising a compound of the present invention has been formulated in a suitable carrier, it can be placed in an appropriate container and labeled for treatment of a PAI-1 related disorder, e.g., leukemia. Additionally, another pharmaceutical comprising at least one other therapeutic agent useful in the treatment of the PAI-1 related disorder can be placed in the container as well and labeled for treatment of the indicated disease. Alternatively, a single pharmaceutical comprising compound of the present invention and at least one other therapeutic agent useful in the treatment of a PAI-1 related disorder can be placed in an appropriate container and labeled for treatment. For administration of pharmaceuticals comprising substituted biphenyloxy acids and of pharmaceuticals comprising, in a single pharmaceutical, substituted biphenyloxy acids and at least one other therapeutic agent useful in the treatment of a PAI-1 related disorder, such labeling would include, for example, instructions concerning the amount, frequency and method of administration. Similarly, for administration of multiple pharmaceuticals provided in the container, such labeling would include, for example, instructions concerning the amount, frequency and method of administration of each pharmaceutical.

EXAMPLES

The syntheses of compounds 1-58 are described in examples 1-58 respectively.

Example 1

Synthesis of ({4'-[({[1-phenyl-5-(trifluoromethyl)-1H-pyrazol-4-yl]carbonyl}amino)methyl][1,1'-biphenyl]-4-yl}oxy)acetic acid Step 1: 4'-Aminomethyl-biphenyl-4-ol. 4'-Hydroxy-biphenyl-4-carbonitrile (10.00 g, 51.2 mmol) in 150 mL of anhydrous THF was added under nitrogen dropwise over 30 minutes to a suspension of LAH (2.91 g, 76.7 mmol) in 200 mL of anhydrous THF at room temperature. After the addition the reaction was refluxed for 20 h (overnight). In the following order 2.91 mL of water, 2.91 mL of 15% KOH and 8.73 mL of water were added dropwise. The reaction was stirred for 30 minutes at room temperature. The solid was removed by filtration and dried under reduced pressure to give a yellow solid which was used in the next step without additional purification.

Step 2: 4-{[(tert-butoxycarbonyl)amino]methyl}-4'-hydroxy-1,1'-biphenyl A suspension of 4'-aminomethyl-biphenyl-4-ol (51.2 mmol), prepared in the previous step, in 500 mL of anhydrous DMF was heated under nitrogen at 60° C. for 10 minutes and then cooled to room temperature. Triethylamine (7.14 mL, 51.2 mmol) was added. Di-tert-butyl dicarbonate (10.07 g, 46.1 mmol) in 100 mL of anhydrous DMF was added dropwise over 2 h. After the addition the reaction was stirred at room temperature for 17 h (overnight). The solid was removed by filtration and the filtrate partitioned between ethyl acetate and water. The organic layer was separated, washed multiple times with water, dried ($MgSO_4$) and the solvent removed under reduced pressure to give 10.23 g of a yellow oil. Purification of the oil on 1 Kg of silica gel (230-400 mesh) using methylene chloride to 15% ethyl acetate-methylene chloride as the eluents gave 4-{[(tert-butoxycarbonyl)amino]methyl}-4'-hydroxy-1,1'-biphenyl (3.40 g, 22%) as an off-white solid, mp 147-149° C. Elemental Analysis for $C_{18}H_{21}NO_3$. Calc'd: C, 72.22; H, 7.07; N, 4.68. Found: C, 70.91; H, 7.03; N, 4.56

Step 3: Methyl[(4'-{[(tert-butoxycarbonyl)amino]methyl}[1,1'-biphenyl]-4-yl)oxy]-acetate. A mixture of 4-{[(tert-butoxycarbonyl)amino]methyl}-4'-hydroxy-1,1'-biphenyl (2.05 g, 6.85 mmol), prepared in the previous step, methyl bromoacetate (648 µL, 6.85 mmol) and potassium carbonate (4.73 g, 34.2 mmol) in 50 mL of DMF was stirred under nitrogen at room temperature for 20 h (overnight). The reaction was partitioned between ethyl acetate and water. The organic layer was separated, extracted multiple times with water, dried ($MgSO_4$) and the solvent removed under reduced pressure to give methyl[(4'-{[(tert-butoxycarbonyl)amino]methyl}[1,1'-biphenyl]-4-yl)oxy]acetate (2.46 g, 97%) as an off-white solid, mp 111-113° C. Elemental Analysis for $C_{21}H_{25}NO_5$. Calc'd: C, 67.91; H, 6.78; N, 3.77 Found: C, 67.70; H, 6.74; N, 3.72

Step 4: 4'-Methoxycarbonylmethoxy-biphenyl-4-ylmethyl-ammonium; chloride A saturated solution of hydrogen chloride in ethyl acetate (100 mL) was added to a solution of methyl[(4'-{[(tert-butoxycarbonyl)amino]methyl}[1,1'-biphenyl]-4-yl)oxy]acetate (1.42 g, 3.81 mmol), prepared in the previous step, in 100 mL of ethyl acetate at room temperature. The reaction was stirred at room temperature for 22 h. The solid was collected by filtration and dried under reduced pressure to give 4'-methoxycarbonylmethoxy-biphenyl-4-ylmethyl-ammonium; chloride (1.11 g, 95%) as a white solid, MS (EI) m/z: 271 M$^+$. Elemental Analysis for $C_{16}H_{17}NO_3 \cdot HCl$. Calc'd: C, 62.44; H, 5.89; N, 4.55. Found: C, 62.07; H, 5.89; N, 4.46.

Step 5: Methyl({4'-[({[1-phenyl-5-(trifluoromethyl)-1H-pyrazol-4-yl]carbonyl}-amino)methyl][1,1'-biphenyl]-4-yl}oxy)acetate. Triethylamine (275 µL, 1.97 mmol) was added under nitrogen to a mixture of 1-phenyl-5-trifluoromethyl-1H-pyrazole-4-carbonyl chloride (272 mg, 0.992 mmol) and 4'-methoxycarbonylmethoxy-biphenyl-4-ylmethyl-ammonium; chloride (304 mg, 0.986 mmol), prepared in the previous step, in 20 mL of methylene chloride at room temperature. The reaction was stirred at room temperature for 6 h. The reaction was extracted with water, 5% $NaHCO_3$, dried ($MgSO_4$) and the solvent removed under reduced pressure to give methyl({4'-[({[1-phenyl-5-(trifluoromethyl)-1H-pyrazol-4-yl]carbonyl}amino)methyl][1,1'-biphenyl]-4-yl}oxy)acetate (508 mg, 100%) as a white solid, mp 174-176° C. Elemental Analysis for $C_{27}H_{22}F_3N_3O_4 + 0.07\ CH_2Cl_2$. Calc'd C, 63.08; H, 4.33; N, 8.15. Found: C, 63.01; H, 4.17; N, 8.16.

Step 6: ({4'-[({[1-phenyl-5-(trifluoromethyl)-1H-pyrazol-4-yl]carbonyl}amino)-methyl][1,1'-biphenyl]-4-yl}oxy)acetic acid. A mixture of methyl({4'-[({[1-phenyl-5-(trifluoromethyl)-1H-pyrazol-4-yl]carbonyl}amino)methyl][1,1'-biphenyl]-4-yl}oxy)acetate (284 mg, 0.557 mmol), prepared in the previous step, and 1 N NaOH (668 µL, 0.668 mmol) in 20 mL of THF and 10 mL of water was stirred at room temperature for 20 h (overnight). The reaction was acidified by the addition of 668 µL of 1 N HCl and then concentrated under reduced pressure to remove the THF. The solid that formed was collected by filtration and dried under reduced pressure to give the title compound (249 mg, 89%) as a white solid, MS (APCI) m/z 496 [M+H]$^+$. Elemental Analysis for $C_{26}H_{20}F_3N_3O_4 + 0.38\ H_2O$. Calc'd: C, 62.17; H, 4.17; N, 8.37 Found: C, 61.91; H, 4.08; N, 8.00

Example 2

Synthesis of ({4'-[({[1-phenyl-5-propyl-1H-pyrazol-4-yl]carbonyl}amino)methyl][1,1'-biphenyl]-4-yl}oxy)acetic acid Step 1: Methyl{[4'-({[(1-phenyl-5-propyl-1H-pyrazol-4-yl)carbonyl]amino}-methyl)-[1,1'-biphenyl]-4-yl]oxy}acetate. Triethylamine (274 µL, 1.97 mmol) was added under nitrogen to a mixture of 1-phenyl-5-propyl-1H-pyrazole-4-carbonyl chloride (249 mg, 1.00 mmol) and 4'-methoxycarbonylmethoxy-biphenyl-4-ylmethyl-ammonium; chloride (303 mg, 0.983 mmol), prepared in step 4 of Example 1, in 20 mL of methylene chloride at room temperature. The reaction was stirred at room temperature for 5 h. The reaction was extracted with water, 5% $NaHCO_3$, dried ($MgSO_4$) and the solvent removed under reduced pressure to give 500 mg of a white solid. Recrystallization of the solid from ethyl acetate gave methyl({4'-[({[1-phenyl-5-propyl-1H-pyrazol-4-yl]carbonyl}amino)methyl][1,1'-biphenyl]-4-yl}oxy)acetate (353 mg, 73%) as a white solid, mp 176-178° C. Elemental Analysis for $C_{29}H_{29}N_3O_4 + 0.13\ EtOAc$ Calc'd: C, 71.63; H, 6.12; N, 8.49. Found: C, 71.43; H, 6.15; N, 8.48

Step 2: ({4'-[({[1-phenyl-5-propyl-1H-pyrazol-4-yl]carbonyl}amino)methyl]-[1,1'-biphenyl]-4-yl}oxy)acetic acid. A mixture of methyl({4'-[({[1-phenyl-5-propyl-1H-pyrazol-4-yl]carbonyl}amino)methyl][1,1'-biphenyl]-4-yl}oxy)acetate (250 mg, 0.517 mmol), prepared in the previous step, and 1 N NaOH (620 µL, 0.620 mmol) in 40 mL of THF and 20 mL of water was stirred at room temperature for 19 h (overnight). The reaction was acidified by the addition of 620 µL of 1 N HCl and then concentrated under reduced pressure to remove the THF. The solid that formed was collected by filtration and dried under reduced pressure to give the title compound (214 mg, 87%) as a white solid, mp 190-192° C. Elemental Analysis for $C_{28}H_{27}N_3O_4 + 0.43\ H_2O$. Calc'd: C, 70.46; H, 5.88; N, 8.80. Found: C, 70.37; H, 5.98; N, 8.44

Example 3

Synthesis of {[3-bromo-4'-({[(1-phenyl-5-propyl-1H-pyrazol-4-yl)carbonyl]amino}methyl)[1,1'-biphenyl]-4-yl]oxy}acetic acid Step 1: tert-butyl (3'-bromo-4'-hydroxy[1,1'-biphenyl]-4-yl)methylcarbamate. Benzyltrimethylammonium tribromide (4.13 g, 10.6 mmol) in 100 mL of methylene chloride was added under nitrogen dropwise over 6.5 h to a mixture of 4-{[(tert-butoxycarbonyl)amino]methyl}-4'-hydroxy-1,1'-biphenyl (3.17 g, 10.6 mmol), prepared in step 2 of Example 1, and calcium carbonate (3.18 g, 31.8 mmol) in 300 mL of methylene chloride plus 120 mL of methanol at room temperature. After the addition the reaction was stirred overnight at room temperature. By TLC some starting material remained. Additional quantities of benzyltrimethylammonium tribromide were added until little or no starting material remained. The reaction was partitioned with water. The material, which was not soluble in either layer, was removed by filtration. The aqueous layer was separated and extracted three times with methylene chloride. The combined organic extracts were dried (MgSO$_4$) and the solvent removed under reduced pressure to give 4.22 g of a white solid foam. Purification of the material on 1 Kg of silica gel (230-400 mesh) using methylene chloride to 6% ethyl acetate-methylene chloride as the eluent gave tert-butyl (3'-bromo-4'-hydroxy[1,1'-biphenyl]-4-yl)methylcarbamate (2.36 g, 59%) as a light yellow solid, mp 113-117° C. Elemental Analysis for C$_{18}$H$_{20}$BrNO$_3$ Calc'd: C, 57.16; H, 5.33; N, 3.70. Found: C, 56.36; H, 5.07; N, 3.48

Step 2: Methyl[(3-bromo-4'-{[(tert-butoxycarbonyl)amino]methyl}[1,1'-biphenyl]-4-yl)oxy]acetate. A mixture of tert-butyl (3'-bromo-4'-hydroxy[1,1'-biphenyl]-4-yl)methylcarbamate (1.50 g, 3.97 mmol), prepared in the previous step, methyl bromoacetate (376 µL, 3.97 mmol) and potassium carbonate (2.74 g, 19.86 mmol) in 50 mL of DMF was stirred under nitrogen at room temperature for 19 h (overnight). The reaction was partitioned between methylene chloride and water. The organic layer was separated, extracted five times with water, dried (MgSO$_4$) and the solvent removed under reduced pressure to give methyl[(3-bromo-4'-{[(tert-butoxycarbonyl)amino]methyl}[1,1'-biphenyl]-4-yl)oxy]acetate (1.67 g, 93%) as a white solid, mp 96-98° C. Elemental Analysis for C$_{21}$H$_{24}$BrNO$_5$. Calc'd: C, 56.01; H, 5.37; N, 3.11. Found: C, 55.47; H, 5.40; N, 3.00

Step 3: 3'-Bromo-4'-methoxycarbonylmethoxy-biphenyl-4-ylmethyl-ammonium; chloride. A saturated solution of hydrogen chloride in ethyl acetate (80 mL) was added to a solution of methyl[(3-bromo-4'-{[(tert-butoxycarbonyl)amino]methyl}[1,1'-biphenyl]-4-yl)oxy]acetate (1.45 g, 3.22 mmol), prepared in the previous step, in 50 mL of ethyl acetate at room temperature. The reaction was stirred at room temperature for 20 h (overnight). The solid was collected by filtration and dried under reduced pressure to give 3'-bromo-4'-methoxycarbonylmethoxy-biphenyl-4-ylmethyl-ammonium; chloride (1.18 g, 94%) as a white solid, mp 228-229° C. Elemental Analysis for C$_{16}$H$_{16}$BrNO$_3$+HCl. Calc'd: C, 49.70; H, 4.43; N, 3.62. Found: C, 49.13; H, 4.27; N, 3.58.

Step 4: Methyl{[3-bromo-4'-({[(1-phenyl-5-propyl-1H-pyrazol-4-yl)carbonyl]-amino}-methyl)[1,1'-biphenyl]-4-yl]oxy}acetate. Triethylamine (217 µL, 1.56 mmol) was added under nitrogen to a mixture of 1-phenyl-5-propyl-1H-pyrazole-4-carbonyl chloride (214 mg, 0.86 mmol) and 3'-bromo-4'-methoxycarbonylmethoxy-biphenyl-4-ylmethyl-ammonium; chloride (300 mg, 0.78 mmol), prepared in the previous step, in 25 mL of methylene chloride at room temperature. The reaction was stirred at room temperature for 19 h (overnight). The reaction was extracted with water, 5% NaHCO$_3$, dried (MgSO$_4$) and the solvent removed under reduced pressure to give 435 mg of a white solid. Recrystallization of the solid from isopropyl alcohol gave methyl{[3-bromo-4'-({[(1-phenyl-5-propyl-1H-pyrazol-4-yl)carbonyl]amino}methyl)[1,1'-biphenyl]-4-yl]oxy}acetate (279 mg, 62%) as a white solid, mp 125-127° C. Elemental Analysis for C$_{29}$H$_{28}$BrN$_3$O$_4$. Calc'd: C, 61.93; H, 5.02; N, 7.47. Found: C, 61.56; H, 4.92; N, 7.42.

Step 5: {[3-bromo-4'-({[(1-phenyl-5-propyl-1H-pyrazol-4-yl)carbonyl]amino}-methyl)-[1,1'-biphenyl]-4-yl]oxy}acetic acid. Methyl{[3-bromo-4'-({[1-phenyl-5-propyl-1H-pyrazol-4-yl)carbonyl]amino}methyl)[1,1'-biphenyl]-4-yl]oxy}acetate (205 mg, 0.36 mmol), prepared in the previous step, in 40 mL of methanol and 10 mL of water was warmed to dissolve the solid. While still warm 1 N NaOH (437 µL, 0.44 mmol) was added and the mixture stirred, with no additional heat, for 4 h. The reaction was acidified by the addition of 437 µL of 1 N HCl and then concentrated under reduced pressure to remove the methanol. The solid that formed was collected by filtration and dried under reduced pressure to give the title compound as a white solid (186 mg, 93%), mp 204-206° C. Elemental Analysis for C$_{28}$H$_{26}$BrN$_3$O$_4$.0.11 H$_2$O. Calc'd: C, 61.10; H, 4.80; N, 7.63. Found: C, 60.49; H, 4.55; N, 7.60.

Example 4

Synthesis of {[3-bromo-4'-({[(2-butyl-1-benzofuran-3-yl)carbonyl]amino}methyl)[1,1'-biphenyl]-4-yl]oxy}acetic acid Step 1: 2-Butyl-benzofuran-3-carboxylic acid. Oxalyl chloride (9.9 mL, 113 mmol) in 50 mL of anhydrous carbon disulfide was added under nitrogen at room temperature to a suspension of aluminum chloride (18.2 g, 136 mmol) in 400 mL of anhydrous carbon disulfide. After the addition the reaction was stirred at room temperature for 15 minutes. 2-Butyl-benzofuran (20.0 mL, 113 mmol) in 50 mL of anhydrous carbon disulfide was then added dropwise over 30 minutes. After the addition the reaction was refluxed for 2 h. After cooling to room temperature 50 mL of 1 N HCl was added dropwise to the reaction (exotherm). The carbon disulfide was decanted from a purple sludge. The sludge was extracted with methylene chloride, combined with the carbon disulfide solution and the solvent removed under reduced pressure. The residue was partitioned between methylene chloride and water. The organic layer was separated and the aqueous layer extracted two times with methylene chloride. The combined extracts were dried (MgSO$_4$) and the solvent removed under reduced pressure. The residue was dissolved in 300 mL of THF plus 300 mL of 1 N NaOH and the mixture stirred at room temperature for 16 h (overnight). The THF was removed under reduced pressure and the residue partitioned between methylene chloride and water. The emulsion that formed was separated by the addition of saturated NaCl. After separating the organic layer the aqueous layer was extracted two times with methylene chloride. The aqueous layer was filtered to remove some suspended solid and then partitioned with 10% MeOH—CH$_2$Cl$_2$ and acidified with 1 N HCl. The organic layer was separated and the aqueous layer extracted two times with 10% MeOH—CH$_2$Cl$_2$. The combined extracts were dried (MgSO$_4$) and the solvent removed under reduced pressure to give 2-butyl-benzofuran-3-carboxylic acid (11.50 g, 47%) as a dark yellow solid, mp 106-110° C.

Elemental Analysis for $C_{13}H_{14}O_3$. Calc'd: C, 71.54; H, 6.47; N, 0.00. Found: C, 70.79; H, 6.45; N, 0.01

Step 2: 2-Butyl-benzofuran-3-carbonyl chloride. Oxalyl Chloride (460 μL, 5.27 mmol) was added under nitrogen at room temperature to a solution of 2-butyl-benzofuran-3-carboxylic acid (230 mg, 1.05 mmol), prepared in the previous step, in 10 mL of methylene chloride. After the addition a catalytic amount of DMF was added and the reaction stirred at room temperature for 1.5 h. The solvent was removed under reduced pressure to give a brown oil. The oil was dissolved in benzene and the solvent removed under reduced pressure to give 2-butyl-benzofuran-3-carbonyl chloride as a brown oil. The material was immediately used in the following reaction with out additional purification.

Step 3: Methyl{[3-bromo-4'-({[(2-butyl-1-benzofuran-3-yl)carbonyl]amino}methyl)-[1,1'-biphenyl]-4-yl]oxy}acetate. Triethyl amine (293 μL, 2.10 mmol) was added under nitrogen to a mixture of 2-butyl-benzofuran-3-carbonyl chloride (1.05 mmol), prepared in the previous step, and 3'-bromo-4'-methoxycarbonylmethoxy-biphenyl-4-ylmethyl-ammonium; chloride (405 mg, 1.05 mmol), prepared in step 3 of Example 3, in 35 mL of methylene chloride at room temperature. The reaction was stirred at room temperature for 19 h (overnight). The reaction was extracted with water, 5% $NaHCO_3$, dried ($MgSO_4$) and the solvent removed under reduced pressure to give 562 mg of a brown solid. Purification of the solid on a 90 g KP-SIL 60 Å Biotage column using 3:1 methylene chloride: hexane to methylene chloride as the eluents gave methyl{[3-bromo-4'-({[(2-butyl-1-benzofuran-3-yl)carbonyl]amino}methyl)[1,1'-biphenyl]-4-yl]oxy}acetate (404 mg, 70%) as a yellow solid, mp 131-134° C. Elemental Analysis for $C_{29}H_{28}BrNO_5$. Calc'd: C, 63.28; H, 5.13; N, 2.54. Found: C, 62.97; H, 5.02; N, 2.54

Step 4: {[3-bromo-4'-({[(2-butyl-1-benzofuran-3-yl)carbonyl]amino}methyl)-[1,1'-biphenyl]-4-yl]oxy}acetic acid. Methyl{[3-bromo-4'-({[(2-butyl-1-benzofuran-3-yl)carbonyl]amino}methyl)[1,1'-biphenyl]-4-yl]oxy}acetate (314 mg, 0.57 mmol), prepared in the previous step, in 100 mL of methanol and 10 mL of water was warmed to dissolve the solid. While still warm 1 N NaOH (684 μL, 0.68 mmol) was added and the mixture stirred, with no additional heat, until the reaction was complete by TLC. The reaction was acidified by the addition of 715 μL of 1 N HCl and then concentrated under reduced pressure to remove the methanol. The solid that formed was collected by filtration and dried under reduced pressure to give the title compound as a light tan solid (270 mg, 87%), mp 175-190° C. Elemental Analysis for $C_{28}H_{26}BrNO_5 \cdot 0.40 H_2O$. Calc'd: C, 61.87; H, 4.97; N, 2.58. Found: C, 61.35; H, 4.54; N, 2.51.

Example 5

Synthesis of N-{[3'-bromo-4'-(H-tetraazol-5-ylmethoxy)[1,1'-biphenyl]-4-yl]methyl}-1-phenyl-5-propyl-1H-pyrazole-4-carboxamide Step 1: 3'-Bromo-4'-hydroxy-biphenyl-4-ylmethyl-ammonium; chloride. A saturated solution of anhydrous hydrogen chloride in ethyl acetate (75 mL) was added to a solution of tert-butyl (3'-bromo-4'-hydroxy[1,1'-biphenyl]-4-yl)methylcarbamate (2.01 g, 5.32 mmol), prepared in step 1 of Example 3, in 75 mL of ethyl acetate at room temperature. The reaction was stirred at room temperature for 19 h (overnight). The solid was removed by filtration and dried under reduced pressure to give 3'-Bromo-4'-hydroxy-biphenyl-4-ylmethyl-ammonium; chloride (1.65 g, 99%) as a light yellow solid, mp 278-281° C. Elemental Analysis for $C_{13}H_{12}BrNO \cdot HCl$. Calc'd: C, 49.63; H, 4.17; N, 4.45. Found: C, 49.07; H, 3.99; N, 4.39.

Step 2: N-[(3'-bromo-4'-hydroxy[1,1'-biphenyl]-4-yl)methyl]-1-phenyl-5-propyl-1H-pyrazole-4-carboxamide. A solution of 1-phenyl-5-propyl-1H-pyrazole-4-carbonyl chloride (478 mg, 1.92 mmol) in 10 mL of methylene chloride was added under nitrogen dropwise over 1 h to a solution of 3'-bromo-4'-hydroxy-biphenyl-4-ylmethyl-ammonium; chloride (605 mg, 1.92 mmol), prepared in the previous step, in 40 mL of anhydrous pyridine at ice bath temperature. After the addition the reaction was stirred at ice bath temperature for 2.5 h. The ice bath was removed and the stirring continued for 17 h (overnight). The solid was removed by filtration and the filtrate concentrated under reduced pressure to remove most of the pyridine. The reaction was taken up in 10% methanol methylene chloride, extracted with 1 N HCl, 5% $NaHCO_3$, dried ($MgSO_4$) and the solvent removed under reduced pressure to give 702 mg of a yellow foam. Purification of the foam on 500 g of silica gel (230-400 mesh) using 1:1 hexane:ethyl acetate as the eluent gave 352 mg of a white solid. Recrystallization of the solid from isopropyl alcohol gave N-[(3'-bromo-4'-hydroxy[-1,1'-biphenyl]-4-yl)methyl]-1-phenyl-5-propyl-1H-pyrazole4-carboxamide (221 mg, 23%) as a light purple solid, mp 184-186° C. Elemental Analysis for $C_{26}H_{24}BrN_3O_2$. Calc'd: C, 63.68; H, 4.93; N, 8.57. Found: C, 63.29; H, 4.74; N, 8.53

Step 3: N-{[3'-bromo-4'-(cyanomethoxy)[1,1'-biphenyl]-4-yl]methyl}-1-phenyl-5-propyl-1H-pyrazole-4-carboxamide). A mixture of N-[(3'-bromo-4'-hydroxy[1,1'-biphenyl]-4-yl)methyl]-1-phenyl-5-propyl-1H-pyrazole-4-carboxamide (173 mg, 0.35 mmol), prepared in the previous step, bromoacetonitrile (30 μL, 0.43 mmol) and potassium carbonate (245 mg, 1.78 mmol) in 5 mL of DMF was stirred under nitrogen at room temperature for 16 h (overnight). The reaction was partitioned between ethyl acetate and water. The organic layer was separated, extracted multiple times with water, dried ($MgSO_4$) and the solvent removed under reduced pressure to give N-{[3'-bromo-4'-(cyanomethoxy)[1,1'-biphenyl]-4-yl]methyl}-1-phenyl-5-propyl-1H-pyrazole-4-carboxamide (186 mg, 100%) as a yellow solid, mp 102-109° C. Elemental Analysis for $C_{28}H_{25}BrN_4O_2$. Calc'd: C, 63.52; H, 4.76; N, 10.58 Found: C, 61.03; H, 4.76; N, 10.02.

Step 4: N-{[3'-bromo-4'-(H-tetraazol-5-ylmethoxy)[1,1'-biphenyl]-4-yl]methyl}-1-phenyl-5-propyl-1H-pyrazole-4-carboxamide. A mixture of N-{[3'-bromo-4'-(cyanomethoxy)[1,1'-biphenyl]-4-yl]methyl}-1-phenyl-5-propyl-1H-pyrazole-4-carboxamide (130 mg, 0.25 mmol), prepared in the previous step, sodium azide (48 mg, 0.74 mmol) and ammonium chloride (39 mg, 0.73 mmol) was stirred under nitrogen at 100° C. for 7.5 h. The reaction was diluted with water, made basic by the addition of a minimum amount of 1 N NaOH and extracted multiple times with ethyl acetate. The aqueous layer was acidified with 1 N HCl. The solid that formed was collected by filtration and dried under reduced pressure to give the title compound (100 mg, 71%) as a white solid, mp 159-163° C. Elemental Analysis for $C_{28}H_{26}BrN_7O_2 \cdot 0.22 H_2O$. Calc'd: C, 58.34; H, 4.62; N, 17.01. Found: C, 58.08; H, 4.33; N, 17.16

Example 6

Synthesis of N-{[3'-bromo-4'-(1H-tetraazol-5-yl-methoxy)-1,1'-biphenyl-4-yl]methyl}-2-butyl-N-methyl-1-benzofuran-3-carboxamide Step 1: 4'-Methoxy-1,1'-biphenyl-4-carbonitrile. A mixture of 4'-hydroxy-1,1'-biphenyl-4-carbonitrile (1.01 g, 5.18 mmol), iodomethane (484 μL, 7.77 mmol) and potassium carbonate (2.15 g, 15.53 mmol) in 25 mL of acetone was stirred under nitrogen at room temperature for 23 h. The acetone was removed under reduced pressure and the residue partitioned between methylene chloride and water. The organic layer was separated, dried ($MgSO_4$) and the solvent removed under reduced pressure to give 996 mg of a light tan solid. Recrystallization of the solid from isopropyl alcohol gave 4'-methoxy-1,1'-biphenyl-4-carbonitrile (735 mg, 68%) as a light tan solid, mp 99-102° C. Elemental Analysis for $C_{14}H_{11}NO$ Calc'd: C, 80.36; H, 5.30; N, 6.69. Found: C, 78.98; H, 5.10; N, 6.25.

Step 2: 4'-Methoxy-1,1'-biphenyl-4-carbaldehyde. Diisobutyl-aluminum hydride (86 mL of a 1 M solution in methylene chloride, 86 mmol) was added under nitrogen dropwise over 1 h to a solution of 4'-methoxy-1,1'-biphenyl-4-carbonitrile (15.0 g, 71.7 mmol), prepared in the previous step, in 500 mL of methylene chloride at ice bath temperature. After the addition the ice bath was removed and the reaction was stirred at room temperature for 1 h. By TLC starting material remained. The reaction was cooled to ice bath temperature and an additional 60 mL (60 mmol) of the diisobutylaluminum hydride was added dropwise over 1 h. After the addition the reaction was stirred at room temperature for 16 h. At room temperature 2 N HCl was added slowly until the reaction was acidic. Additional water and methylene chloride were added and the mixture filtered. The organic layer was then separated and the aqueous layer extracted multiple times with methylene chloride. The combined extracts were dried ($MgSO_4$) and the solvent removed under reduced pressure to give 4'-methoxy-1,1'-biphenyl-4-carbaldehyde (12.5 g, 82%) as a pale yellow solid, MS (EI) m/z 212. Elemental Analysis for $C_{14}H12O_2$. Calc'd: C, 79.23; H, 5.70; N, 0.00. Found: C, 77.92; H, 5.87; N, 0.00

Step 3: 3'-Bromo-4'-methoxy-1,1'-biphenyl-4-carbaldehyde. Bromine (8.2 mL, 0.160 mol) in 40 mL of glacial HOAc was added under nitrogen dropwise over 30 minutes to a solution of 4'-methoxy-1,1'-biphenyl-4-carbaldehyde (31.0g, 0.146 mol), prepared in the previous step, in 500 mL of glacial HOAc at room temperature. After the addition the reaction was stirred at room temperature for 16 h. During the reaction a solid precipitated. The solid can be collected by filtration. If by TLC starting material remains in either the solid or filtrate the solid can be redissolved and additional bromine added until the reaction is complete. When the reaction is complete by TLC, water is added and the solid present is collected by filtration to give 3'-bromo-4'-methoxy-1,1'-biphenyl-4-carbaldehyde (40.8 g, 96%) as a white solid, MS (ESI) m/z 290. Elemental Analysis for $C_{14}H_{11}BrO_2$. Calc'd: C, 57.76; H, 3.81; N, 0.00. Found: C, 57.30; H, 3.61; N, 0.00.

Step 4: N-[(E)-(3'-bromo-4'-methoxy-1,1'-biphenyl-4-yl)methylidene]-N-methyl-amine. A mixture of 3'-bromo-4'-methoxy-1,1'-biphenyl-4-carbaldehyde (7.56g, 26.0 mmol), prepared in the previous step, methylamine (16.2 mL of an 8.03 M solution in ethanol; 130 mmol) and 20.0 g of anhydrous $MgSO_4$ in 150 mL of methylene chloride was stirred under nitrogen at room temperature for 22 h. The reaction was filtered and the filtrate concentrated under reduced pressure to give N-[(E)-(3'-bromo-4'-methoxy-1,1'-biphenyl-4-yl)methylidene]-N-methylamine (7.77 g, 98%) as a brown solid, mp 115-117° C. Elemental Analysis for $C_{15}H_{14}BrNO$. Calc'd: C, 59.23; H; 4.64; N, 4.60. Found: C, 58.99; H, 4.38; N, 4.63

Step 5: N-[(3'-bromo-4'-methoxy-1,1'-biphenyl-4-yl)methyl]-N-methylamine. A suspension of N-[(E)-(3'-bromo-4'-methoxy-1,1'-biphenyl-4-yl)methylidene]-N-methylamine (7.57 g, 24.9 mmol), prepared in the previous step, in 300 mL of absolute ethanol under nitrogen was warmed to dissolve the solid. While still warm sodium borohydride (942 mg, 24,9 mmol) was added in portions over five minutes. After the addition the reaction was stirred at room temperature for 18 h (overnight). The reaction was acidified by the addition of 1 N HCl and then concentrated under reduced pressure to remove most of the ethanol. The residue was suspended between methylene chloride and 1 N NaOH. The solid that did not dissolve was collected by filtration and dried under reduced pressure to give the HCl salt of the desired product (3.10 g, 36%) as an off-white solid. The organic layer of the filtrate was separated and the aqueous layer extracted three times with methylene chloride. The combined extracts were dried ($MgSO_4$) and the solvent removed under reduced pressure to give N-[(3'-bromo-4'-methoxy-1,1'-biphenyl-4-yl)methyl]-N-methylamine (4.77 g, 63%) as a yellow solid, mp 65-68° C. Elemental Analysis for $C_{15}H_{16}BrNO$. Calc'd: C, 58.84; H, 5.27; N, 4.57. Found: C, 58.96; H, 5.20; N, 4.53.

Step 6: N-[(3'-bromo-4'-methoxy-1,1'-biphenyl-4-yl)methyl]-2-butyl-N-methyl-1-benzofuran-3-carboxamide. 2-Butyl-benzofuran-3-carbonyl chloride (14.7 mmol), prepared in step 2 of Example 4, in 50 mL of methylene chloride was added under nitrogen dropwise over 15 minutes to a solution of N-[(3'-bromo-4'-methoxy-1,1'-biphenyl-4-yl)methyl]-N-methylamine (4.49 g, 14.7 mmol), prepared in the previous step, and triethylamine (2.05 mL, 14.7 mmol) in 150 mL of methylene chloride at room temperature. After the addition the reaction was stirred at room temperature for 16 h (overnight). The reaction was extracted with 1 N HCl, 5% $NaHCO_3$, dried ($MgSO_4$) and the solvent removed under reduced pressure to give 7.30 g of a brown foam. Purification of the foam on 500 g of silica gel (230-400 mesh) using methylene chloride as the eluent gave N-[(3'-bromo-4'-methoxy-1,1'-biphenyl-4-yl)methyl]-2-butyl-N-methyl-1-benzofuran-3-carboxamide (5.53 g, 74%) as a yellow foam, MS (ESI) m/z 506 $[M+H]^+$. Elemental Analysis for $C_{28}H_{28}BrNO_3$. Calc'd: C, 66.41; H, 5.57; N, 2.77. Found: C, 66.03; H, 5.41; N, 2.59

Step 7: N-[(3'-bromo-4'-hydroxy-1,1'-biphenyl-4-yl)methyl]-2-butyl-N-methyl-1-benzofuran-3-carboxamide. Boron tribromide (31.8 mL of a 1 M solution in methylene chloride; 31.8 mmol) was added under nitrogen dropwise over 30 minutes to a solution of N-[(3'-bromo-4'-methoxy-1,1'-biphenyl-4-yl)methyl]-2-butyl-N-methyl-1-benzofuran-3-carboxamide (5.37 g, 10.6 mmol), prepared in the previous step, in 150 mL of methylene chloride at dry ice-acetone temperature. After the addition the dry ice-acetone bath was replaced with an ice bath and the stirring continued for 1.5 h. At ice bath temperature-water was added dropwise. The aqueous layer was separated and extracted two times with methylene chloride. The extracts were combined, dried ($MgSO_4$) and the solvent removed under reduced pressure to give N-[(3'-bromo-4'-hydroxy-1,1'-biphenyl-4-yl)methyl]-2-butyl-N-methyl-1-benzofuran-3-carboxamide (5.26 g, 100%) as a light brown foam, MS (ESI) m/z 492 $[M+H]^+$. Elemental Analysis for $C_{27}H_{26}BrNO_3$. Calc'd: C, 65.86; H, 5.32; N, 2.84. Found: C, 64.98; H, 5.15; N, 2.63.

Step 8: N-{[3'-bromo-4'-(cyanomethoxy)-1,1'-biphenyl-4-yl]methyl}-2-butyl-N-methyl-1-benzofuran-3-carboxamide. A mixture N-[(3'-bromo-4'-hydroxy-1,1'-biphenyl-4-yl)methyl]-2-butyl-N-methyl-1-benzofuran-3-carboxamide (1.60 g, 3.25 mmol), prepared in the previous step, bromoacetonitrile (272 µL, 3.90 mmol) and potassium carbonate (2.25 g, 16.3 mmol) in 25 mL of DMF was stirred under nitrogen at room temperature for 23 h. The reaction was partitioned between ethyl acetate and water. The organic layer was separated, extracted multiple times with water, dried (MgSO$_4$) and the solvent removed under reduced pressure to give N-{[3'-bromo-4'-(cyanomethoxy)-1,1'-biphenyl-4-yl]methyl}-2-butyl-N-methyl-1-benzofuran-3-carboxamide (1.65 g, 95%) as a brown foam, MS (ESI) m/z 531 [M+H]$^+$. Elemental Analysis for C$_{29}$H$_{27}$BrN$_2$O$_3$. Calc'd: C, 65.54; H, 5.12; N, 5.27. Found: C, 65.37; H, 5.14; N, 5.21.

Step 9: N-{[3'-bromo-4'-(H-tetraazol-5-ylmethoxy)-1,1'-biphenyl-4-yl]methyl}-2-butyl-N-methyl-1-benzofuran-3-carboxamide. A mixture of N-{[3'-bromo-4'-(cyanomethoxy)-1,1'-biphenyl-4-yl]methyl}-2-butyl-N-methyl-1-benzofuran-3-carboxamide (1.42 g, 2.68 mmol), prepared in the previous step, sodium azide (523 mg, 8.05 mmol) and ammonium chloride (433 mg, 8.09 mmol) in 30 mL of DMF was stirred under nitrogen at 100° C. for 5 h. The reaction was diluted with 50 mL of water, made basic by the addition of 10 mL of 1 N NaOH and partitioned with ethyl acetate. The organic layer was separated and the aqueous layer extracted multiple times with ethyl acetate. The aqueous layer was acidified with 20 mL of 1 N HCl. The yellow oil that precipitated was separated from the aqueous layer. By TLC the ethyl acetate layer contained a lot of product. The ethyl acetate layer was acidified with 1 N HCl and concentrated under reduced pressure to remove the ethyl acetate. The residue was diluted with water. The oil that precipitated was separated and combined with the previous isolated yellow oil. The combined oils were dissolved in methylene chloride, extracted multiple times with water, dried (MgSO$_4$) and the solvent removed under reduced pressure to give the title compound (1.33 g, 86%) as a light tan solid foam, MS (ESI) m/z 574 [M+H]$^+$. Elemental Analysis for C$_{29}$H$_{28}$BrN$_5$O$_3$.0.18 H$_2$O. Calc'd: C, 60.29; H, 4.95; N, 12.12. Found: C, 59.92; H, 5.10; N, 12.09

Example 7

Synthesis of [(3-bromo-4'-{[[(2-butyl-1-benzofuran-3-yl)carbonyl](methyl)amino]methyl}-1,1'-biphenyl-4-yl)oxy]acetic acid Step 1: methyl[(3-bromo-4'-{[[(2-butyl-1-benzofuran-3-yl)carbonyl](methyl)-amino]methyl}-1,1'-biphenyl-4-yl)oxy]acetate. A mixture of N-[(3'-bromo-4'-hydroxy-1,1'-biphenyl-4-yl)methyl]-2-butyl-N-methyl-1-benzofuran-3-carboxamide (1.01 g, 2.04 mmol), prepared in step 7 of Example 6, methyl bromoacetate (213 µL, 2.25 mmol) and potassium carbonate (1.41 g, 10.2 mmol) in 20 ml of DMF was stirred under nitrogen at room temperature for 23 h (overnight). The reaction was partitioned between ethyl acetate and water. The organic layer was separated, extracted multiple times with water, dried (MgSO$_4$) and the solvent removed under reduced pressure to give methyl[(3-bromo-4'-{[[(2-butyl-1-benzofuran-3-yl)carbonyl](methyl)amino]methyl}-1,1'-biphenyl-4-yl)oxy]acetate (1.07 g, 93%) as a yellow oil, MS (ESI) m/z 564 [M+H]$^+$. Elemental Analysis for C$_{30}$H$_{30}$BrNO$_5$. Calc'd: C, 63.83; H, 5.36; N, 2.48. Found: C, 63.42; H, 5.40; N, 2.39.

Step 2: [(3-bromo-4'-{[[(2-butyl-1-benzofuran-3-yl)carbonyl](methyl)amino]methyl}-1,1'-biphenyl-4-yl)oxy]acetic acid. 1 N NaOH (2.14 mL, 2.14 mmol) was added under nitrogen to a solution of methyl[(3-bromo-4'-{[[(2-butyl-1-benzofuran-3-yl)carbonyl](methyl)amino]methyl}-1,1'-biphenyl-4-yl)oxy]acetate (1.00 g, 1.78 mmol), prepared in the previous step, in 50 mL of methanol plus 5 mL of water at room temperature. After the addition the reaction was stirred at room temperature for 4 h. The reaction was acidified by the addition of 2.5 mL of 1 N HCl and then concentrated under reduced pressure to remove most of the methanol. The solid present was collected by filtration, rinsed with water and dried under reduced pressure to give the title compound (932 mg, 100%) as a light brown solid, mp 72-78° C. Elemental Analysis for C$_{29}$H$_{28}$BrNO$_5$.0.15 H$_2$O. Calc'd: C, 62.97; H, 5.16; N, 2.53. Found: C, 62.71; H, 5.19; N, 2.39

Example 8

Synthesis of 2-[(3-bromo-4'-{[[(2-butyl-1-benzofuran-3-yl)carbonyl](methyl)amino]methyl}-1,1'-biphenyl-4-yl)oxy]-3-phenylpropanoic acid Step 1: 2-Hydroxy-3-phenyl-propionic acid methyl ester. Hydrogen chloride was bubbled for 15 minutes into a solution of 2-hydroxy-3-phenyl-propionic acid (10.0 g, 60 mmol) in 100 mL of methanol at room temperature. The vessel was sealed and then stirred overnight at room temperature. The reaction was made basic by the addition of 5% NaHCO$_3$ and then concentrated under reduced pressure to remove the methanol. The residue was diluted with water and extracted with ethyl acetate. The organic layer was extracted with saturated NaCl, dried (MgSO$_4$) and the solvent removed under reduced pressure to give 2-hydroxy-3-phenyl-propionic acid methyl ester (9.7 g, 90%) as a yellow oil, MS m/z 180 [M]$^+$. Elemental Analysis for C$_{10}$H$_{12}$O$_3$. Calc'd: C, 66.65; H, 6.71; N, 0.00. Found: C, 66.52; H, 6.86; N, 0.29

Step 2: 3-Phenyl-2-trifluoromethanesulfonyloxy-propionic acid methyl ester. Triethylamine (931 µL, 6.68 mmol) was added under nitrogen to a solution of 2-hydroxy-3-phenyl-propionic acid methyl ester (1.00 g, 5.57 mmol), prepared in the previous step, in 20 mL of chloroform (99.9%; free of ethanol) at dry ice-acetone temperature. Trifluoromethanesulfonic anhydride (1.03 mL, 6.13 mmol) was then added dropwise over 15 minutes. The cooling bath was removed and the reaction was stirred overnight at room temperature. The reaction was extracted with 1 N HCl, 5% NaHCO$_3$, dried (MgSO$_4$) and the solvent removed under reduced pressure to give 1.53 g a brown oil. Purification of the oil on 100 g of silica gel (230-400 mesh) using 3:1 methylene chloride-hexane as the eluent gave 3-phenyl-2-trifluoromethanesulfonyloxy-propionic acid methyl ester (1.106 g, 64%) as clear oil. Elemental Analysis for C$_{11}$H$_{11}$F$_3$O$_5$SCalc'd: C, 42.31; H, 3.55; N, 0.00. Found: C, 42.15; H, 3.35; N, 0.14.

Step 3: methyl2-[(3-bromo-4'-{[[(2-butyl-1-benzofuran-3-yl)carbonyl](methyl)-amino]methyl}-1,1'-biphenyl-4-yl)oxy]-3-phenylpropanoate. A mixture of N-[(3'-bromo-4'-hydroxy-1,1'-biphenyl-4-yl)methyl]-2-butyl-N-methyl-1-benzofuran-3-carboxamide (1.21 g, 2.46 mmol), prepared in step 7 of Example 6, 3-phenyl-2-trifluoromethanesulfonyloxy-propionic acid methyl ester (1.15 g, 3.69 mmol), prepared in the previous step, and cesium carbonate (1.61 g, 4.94 mmol) in 50 mL of acetone was stirred under nitrogen at room temperature for 19 h. The reaction was concentrated under reduced pressure to remove the acetone. The residue was partitioned between ethyl acetate and water. The aqueous layer was separated and extracted two times with ethyl acetate. The combined extracts were dried (MgSO$_4$) and the solvent removed under reduced pressure to give 1.71 g of a yellow oil. Purification of the oil on 500 g of silica gel (230-400 mesh) using methylene chloride to 2% ethyl acetate-methylene chloride as the eluents gave methyl 2-[(3-bromo-4'-{[[(2-butyl-1-benzofuran-3-yl)carbonyl](methyl)amino]methyl}-1,1'-biphenyl-4-yl)oxy]-3-phenylpropanoate (1.31 g, 81% as a light yellow foam, MS (ESI) m/z 654 [M+H]$^+$. Elemental Analysis for $C_{37}H_{36}BrNO_5$. Calc'd: C, 67.89; H, 5.54; N, 2.14. Found: C, 67.19; H, 5.59; N, 2.01.

Step 4: 2-[(3-bromo-4'-{[[(2-butyl-1-benzofuran-3-yl)carbonyl](methyl)amino]-methyl}-1,1'-biphenyl-4-yl)oxy]-3-phenylpropanoic acid. 1 N NaOH (2.28 mL, 2.28 mmol) was added under nitrogen to a solution of methyl2-[(3-bromo-4'-{[[(2-butyl-1-benzofuran-3-yl)carbonyl](methyl)amino]methyl}-1,1'-biphenyl-4-yl)oxy]-3-phenylpropanoate (995 mg, 1.52 mmol), prepared in the previous step, in 100 mL of methanol plus 10 mL of water. After the addition the reaction was refluxed for 5 h. The reaction was filtered, acidified with 2.5 mL of 1 N HCl and concentrated under reduced pressure to remove the methanol. The solid that was present was collected by filtration and dried under reduced pressure to give the title compound (900 mg, 92%) as a white solid, mp 79-86° C. Elemental Analysis for $C_{36}H_{34}BrNO_5$Calc'd: C, 67.50; H, 5.35; N, 2.19. Found: C, 6 7.16; H, 5.42; N, 2.09

Example 9

Synthesis of N-{[3'-bromo-4'-(1H-tetraazol-5-ylmethoxy)-1,1'-biphenyl-4-yl]methyl}-N,1-dimethyl-1H-indole-3-carboxamide Step 1: 1-Methyl-1H-indole-3-carbonyl chloride. Oxalyl chloride (7.1 mL, 81.4 mmol) in 50 mL of methylene chloride was added under nitrogen dropwise to a solution of 1-methyl-1H-indole carboxylic acid (2.86 g, 16.3 mmol) in 100 mL of methylene chloride at room temperature. After the addition the reaction was stirred at room temperature until the reaction was determined by NMR analysis to be complete. The solvent and excess oxalyl chloride were removed under reduced pressure. The residue was taken up in benzene and then concentrated to dryness under reduced pressure to give 1-methyl-1H-indole-3-carbonyl chloride, which was used in the following reaction without purification.

Step 2: N-[(3'-bromo-4'-methoxy-1,1'-biphenyl-4-yl)methyl]-N,1-dimethyl-1H-indole-3-carboxamide. 1-methyl-1H-indole-3-carbonyl chloride (16.3 mmol), prepared in the previous step, in 50 mL of methylene chloride was added under nitrogen dropwise to a solution of N-[(3'-bromo-4'-methoxy-1,1'-biphenyl-4-yl)methyl]-N-methylamine (5.00 g, 16.3 mmol), prepared in step 5 of Example 6, and triethylamine (2.3 mL, 16.3 mmol) in 200 mL of methylene chloride at room temperature. After the addition the reaction was stirred at room temperature for 20 h. The reaction was extracted with 1 N HCl, dried (MgSO$_4$) and the solvent removed under reduced pressure to give N-[(3'-bromo-4'-methoxy-1,1'-biphenyl-4-yl)methyl]-N,1-dimethyl-1H-indole-3-carboxamide (7.4 g, 98%) as a white solid foam, MS (ESI) m/z 463 [M+H]$^+$. Elemental Analysis for $C_{25}H_{23}BrN_2O_2$. Calc'd: C, 64.80; H, 5.00; N, 6.05 Found: C, 62.88; H, 4.92; N, 5.61

Step 3: N-[(3'-bromo-4'-hydroxy-1,1'-biphenyl-4-yl)methyl]-N,1-dimethyl-1H-indole-3-carboxamide. Boron tribromide (44.8 mL of a 1 M solution in methylene chloride; 44 mmol) was added under nitrogen dropwise over 30 minutes to a solution of N-[(3'-bromo-4'-methoxy-1,1'-biphenyl-4-yl)methyl]-N,1-dimethyl-1H-indole-3-carboxamide (6.8 g, 14.7 mmol), prepared in the previous step, in 150 mL of methylene chloride at dry ice-acetone temperature. After the addition the dry ice-acetone bath was replaced with an ice bath and the stirring continued for 3 h. At ice bath temperature 60 mL of water was added dropwise. The reaction was then partitioned between additional amounts of methylene chloride and water. The aqueous layer was separated and extracted three times with methylene chloride. The combined extracts were dried (MgSO$_4$) and the solvent removed under reduced pressure to give N-[(3'-bromo-4'-hydroxy-1,1'-biphenyl-4-yl)methyl]-N,1-dimethyl-1H-indole-3-carboxamide (4.7 g, 71%) as a solid, mp 237-239° C. Elemental Analysis for $C_{24}H_{21}BrN_2O_2$. Calc'd: C, 64.15; H, 4.71; N, 6.23. Found: C, 62.15; H, 4.63; N, 5.97.

Step 4: N-{[3'-bromo-4'-(cyanomethoxy)-1,1'-biphenyl-4-yl]methyl}-N,1-dimethyl-1H-indole-3-carboxamide. A mixture of N-[(3'-bromo-4'-hydroxy-1,1'-biphenyl-4-yl)methyl]-N,1-dimethyl-1H-indole-3-carboxamide (4.6 g, 10.2 mmol), prepared in the previous step, bromoacetonitrile (856 µL, 12.3 mmol) and potassium carbonate (7.0 g, 50 mmol) in 75 mL of DMF was stirred under nitrogen at room temperature for 23 h (overnight). The reaction was partitioned between ethyl acetate and water. The organic layer was separated, extracted multiple times with water, dried (MgSO$_4$) and the solvent removed under reduced pressure to give N-{[3'-bromo-4'-(cyanomethoxy)-1,1'-biphenyl-4-yl]methyl}-N,1-dimethyl-1H-indole-3-carboxamide (3.4 g, 68%) as an off-white solid, mp 202-206° C. Elemental Analysis for $C_{26}H_{22}BrN_3O_2$. Calc'd: C, 63.94; H, 4.54; N, 8.60. Found: C, 50.59; H, 3.30; N, 8.00

Step 5: N-{[3'-bromo-4'-(1H-tetraazol-5-ylmethoxy)-1,1'-biphenyl-4-yl]methyl}-N,1-dimethyl-1H-indole-3-carboxamide. A mixture of N-{[3'-bromo-4'-(cyanomethoxy)-1,1'-biphenyl-4-yl]methyl}-N,1-dimethyl-1H-indole-3-carboxamide (2.0 g, 4.1 mmol), prepared in the previous step, sodium azide (0.80 g, 12.3 mmol) and ammonium chloride (0.66 g, 12.3 mmol) in 42 mL of DMF was stirred under nitrogen at 100° C. for 4 h. By TLC a small amount of starting material remained. An additional 0.80 g (12.3 mmol) of sodium azide and 0.66 g (12.3 mmol) of ammonium chloride were added and the reaction stirred at 100° C. for 3 h. After cooling to room temperature the reaction was diluted with 65 mL of water, made basic by the addition of 1 N NaOH and extracted three times with ethyl acetate. The aqueous layer was acidified with 1 N HCl. An oil separated which eventually solidified. The solid was collected by filtration, rinsed with water and dried under reduced pressure to give the title compound (1.6 g, 73%) as a tan solid, mp 239° C. Elemental Analysis for $C_{26}H_{23}BrN_6O_2$Calc'd: C, 58.77; H, 4.36; N, 15.81. Found: C, 57.73; H, 4.40; N, 15.52

Example 10

Synthesis of 1-Benzyl-N-{[3'-bromo-4'-(1H-tetraazol-5-ylmethoxy)-1,1'-biphenyl-4-yl]methyl}-N-methyl-1H-indole-3-carboxamide Step 1: 1-Benzyl-1H-indole-3-carbonyl chloride. Oxalyl chloride (7.1 mL, 81.4 mmol) was added under nitrogen dropwise over 10 minutes to a suspension of 1-benzyl-1H-indole-3-carboxylic acid (4.10 g, 16.3 mmol) in 200 mL of methylene chloride at room temperature. When the oxalyl chloride was added there was an immediate evolution of gas and within 30 minutes all of the solid had dissolved. After the addition of the oxalyl chloride the reaction was stirred at room temperature for 2 h. The solvent and excess oxalyl chloride were removed under reduced pressure. The residue was taken up in benzene and then concentrated to dryness under reduced pressure to give 1-benzyl-1H-indole-3-carbonyl chloride, which was used in the following reaction without purification.

Step 2: 1-benzyl-N-[(3'-bromo-4'-methoxy-1,1'-biphenyl-4-yl)methyl]-N-methyl-1H-indole-3-carboxamide. 1-Benzyl-1H-indole-3-carbonyl chloride (16.3 mmol), prepared in the previous step, in 50 mL of methylene chloride was added under nitrogen dropwise over 1 h to a solution of N-[(3'-bromo-4'-methoxy-1,1'-biphenyl-4-yl)methyl]-N-methylamine (5.00 g, 16.3 mmol), prepared in step 5 of Example 6, and triethylamine (2.28 mL, 16.3 mmol) in 200 mL of methylene chloride at room temperature. After the addition the reaction was stirred at room temperature for 16 h (overnight). The reaction was extracted with 1 N HCl, 5% NaHCO$_3$, dried (MgSO$_4$) and the solvent removed under reduced pressure to give 9.02 g of an off-white foam. Purification of the foam on 500 g of silica gel (230-400 mesh) using 1% to 8% ethyl acetate-methylene chloride as the eluents gave 1-benzyl-N-[(3'-bromo-4'-methoxy-1,1'-biphenyl-4-yl)methyl]-N-methyl-1H-indole-3-carboxamide (7.86 g, 89%) as a white foam, MS (ESI) m/z 539 [M+H]+. Elemental Analysis for C$_{31}$H$_{27}$BrN$_2$O$_2$. Calc'd: C, 69.02; H, 5.04; N, 5.19. Found: C, 68.34; H, 5.24; N, 4.86.

Step 3: 1-Benzyl-N-[(3'-bromo-4'-hydroxy-1,1'-biphenyl-4-yl)methyl]-N-methyl-1H-indole-3-carboxamide. Boron tribromide (41.4 mL of a 1 M solution in methylene chloride; 41.4 mmol) was added under nitrogen dropwise over 30 minutes to a solution of 1-benzyl-N-[(3'-bromo-4'-methoxy-1,1'-biphenyl-4-yl)methyl]-N-methyl-1H-indole-3-carboxamide (7.46 g, 13.8 mmol), prepared in the previous step, in 200 mL of methylene chloride at dry ice-acetone temperature. After the addition the dry ice-acetone bath was replaced with an ice bath and the stirring was continued for 3.5 h. At ice bath temperature 50 mL of water was added dropwise. The reaction was then partitioned between additional amounts of methylene chloride and water. The aqueous layer was separated and extracted three times with methylene chloride. The combined extracts were dried (MgSO$_4$) and the solvent removed under reduced pressure to give 1-benzyl-N-[(3'-bromo-4'-hydroxy-1,1'-biphenyl-4-yl)methyl]-N-methyl-1H-indole-3-carboxamide (7.13 g, 98%) as a light tan solid, mp 164-170° C. Elemental Analysis for C$_{30}$H$_{25}$BrN$_2$O$_2$ Calc'd: C, 68.58; H, 4.80; N, 5.33. Found: C, 67.27; H, 4.78; N, 5.19

Step 4: 1-Benzyl-N-{[3'-bromo-4'-(cyanomethoxy)-1,1'-biphenyl-4-yl]methyl}-N-methyl-1H-indole-3-carboxamide. A mixture of 1-benzyl-N-[(3'-bromo-4'-hydroxy-1,1'-biphenyl-4-yl)methyl]-N-methyl-1H-indole-3-carboxamide (1.60 g, 3.05 mmol), prepared in the previous step, bromoacetonitrile (255 µL, 3.66 mmol) and potassium carbonate (2.11 g, 15.30 mmol) in 25 mL of DMF was stirred under nitrogen at room temperature for 16 h (overnight). The reaction was partitioned between ethyl acetate and water. The organic layer was separated, extracted multiple times with water, dried (MgSO$_4$) and the solvent removed under reduced pressure to give 1-benzyl-N-{[3'-bromo-4'-(cyanomethoxy)-1,1'-biphenyl-4-yl]methyl}-N-methyl-1H-indole-3-carboxamide (1.69 g, 98%) as a yellow foam, MS (ESI) m/z 564 [M+H]+. Elemental Analysis for C$_{32}$H$_{26}$BrN$_3$O$_2$: Calc'd: C, 68.09; H, 4.64; N, 7.44; Found: C, 67.53; H, 4.57; N, 7.14

Step 5: 1-Benzyl-N-{[3'-bromo-4'-(1H-tetraazol-5-ylmethoxy)-1,1'-biphenyl-4-yl]methyl}-N-methyl-1H-indole-3-carboxamide. A mixture of 1-benzyl-N-{[3'-bromo-4'-(cyanomethoxy)-1,1'-biphenyl-4-yl]methyl}-N-methyl-1H-indole-3-carboxamide (1.56 g, 2.76 mmol), prepared in the previous step, sodium azide (542 mg, 8.34 mmol) and ammonium chloride (446 mg, 8.33 mmol) in 30 mL of DMF was stirred under nitrogen at 100° C. for 6 h. After cooling to room temperature the reaction was diluted with 50 mL of water, made basic by the addition of 10 mL of 1 N NaOH and extracted five times with ethyl acetate. The aqueous layer was filtered and then acidified with 20 mL of 1 N HCl. An oil precipitated. The aqueous layer was decanted and the oil partitioned between methylene chloride and water. The organic layer was separated, dried (MgSO$_4$) and the solvent removed under reduced pressure to give the title compound (1.22 g, 72%) as a light yellow foam, MS (ESI) m/z 607 [M+H]+. Elemental Analysis for C$_{32}$H$_{27}$BrN$_6$O$_2$.0.08 H$_2$O: Calc'd: C, 63.12; H, 4.50; N, 13.80; Found: C, 61.37; H, 4.65; N, 12.89.

Example 11

Synthesis of N-benzyl-N-{[3'-bromo-4'-(1H-tetraazol-5-ylmethoxy)-1,1'-biphenyl-4-yl]methyl}-2-butyl-1-benzofuran-3-carboxamide Step 1: N-benzyl-N-[(1Z)-(3'-bromo-4'-methoxy-1,1'-biphenyl-4-yl)methylidene]-amine. A mixture of 3'-bromo-4'-methoxy-1,1'-biphenyl-4-carbaldehyde (19.4 g, 69 mmol), prepared in step 3 of Example 6, benzylamine (38 mL, 345 mmol) and 60 g of anhydrous MgSO$_4$ in 400 mL of methylene chloride was stirred under nitrogen at room temperature for 18 h. The reaction was filtered and the filtrate concentrated under reduced pressure to give an off-white solid. The solid was triturated with hexane and dried under reduced pressure to give N-benzyl-N-[(1Z)-(3'-bromo-4'-methoxy-1,1'-biphenyl-4-yl)methylidene]amine (23.6 g, 88%) as an off-white solid, MS KESI) m/z 380 [M+H]+. Elemental analysis for C$_{21}$H$_{18}$BrNO: Calc'd: C, 66.33; H, 4.77; N, 3.68; Found: C, 63.22; H, 4.85; N, 4.17

Step 2: N-benzyl-N-[(3'-bromo-4'-methoxy-1,1'-biphenyl-4-yl)methyl]amine. A suspension of N-benzyl-N-[(1Z)-(3'-bromo-4'-methoxy-1,1'-biphenyl-4-yl)methylidene]amine (22.2 g, 53.4 mmol), prepared in the previous step, in 800 mL of absolute ethanol was warmed under nitrogen to dissolve the solid. While still warm sodium borohydride (2.11 g, 55.8 mmol) was added slowly in small portions. After the addition the reaction was stirred at room temperature for 38 h. The reaction was acidified by the addition of 90 mL of 2 N HCl and then concentrated under reduced pressure to remove the ethanol. The residue was suspended between water (400 mL) and ethyl acetate (300 mL) and then filtered to remove any solid that did not dissolve. The ethyl acetate layer was separated and the aqueous layer extracted two times with methylene chloride (2×300 mL). The extracts were combined, dried (MgSO$_4$) and the solvent removed under reduced pressure to give the HCl salt of N-benzyl-N-[(3'-bromo-4'-methoxy-1,1'-biphenyl-4-yl)methyl]amine (13.0 g, 54%), mp 244-248° C. Elemental Analysis for C$_{21}$H$_{20}$BrNO.HCl: Calc'd: C, 60.23; H, 5.05; N, 3.34; Found: C, 56.41; H, 4.63; N, 2.91

Step 3: N-benzyl-N-[(3'-bromo-4'-methoxy-1,1'-biphenyl-4-yl)methyl]-2-butyl-1-benzofuran-3-carboxamide. 2-Butyl-benzofuran-3-carbonyl chloride (16 mmol), prepared in step 2 of Example 4, in 20 mL of methylene chloride was added under nitrogen dropwise over 15 minutes to a solution of the HCl salt of N-benzyl-N-[(3'-bromo-4'-methoxy-1,1'-biphenyl-4-yl)methyl]amine (5.0 g, 11.9 mmol), prepared in the previous step, and triethylamine (4.6 mL, 33.0 mmol) in 100 mL of methylene chloride at room temperature. After the addition the reaction was stirred at room temperature for 20 h. The reaction was extracted with 1 N HCl, dried (MgSO$_4$) and the solvent removed under reduced pressure to give 5 g of a dark residue. Purification of the residue on silica gel (230-400 mesh) using methylene chloride as the eluent gave N-benzyl-N-[(3'-bromo-4'-methoxy-1,1'-biphenyl-4- yl)methyl]-2-butyl-1-benzofuran-3-carboxamide (4.2 g, 61%) as a tan solid, mp 145-148° C. Elemental Analysis for $C_{34}H_{32}BrNO_3$: Calc'd: C, 70.10; H, 5.54; N, 2.40; Found: C, 69.37; H, 5.39; N, 2.14.

Step 4: N-benzyl-N-[(3'-bromo-4'-hydroxy-1,1'-biphenyl-4-yl)methyl]-2-butyl-1-benzofuran-3-carboxamide. Boron tribromide (22.0 mL of a 1 M solution in methylene chloride; 22.0 mmol) was added under nitrogen dropwise over 30 minutes to a solution N-benzyl-N-[(3'-bromo-4'-methoxy-1,1'-biphenyl-4-yl)methyl]-2-butyl-1-benzofuran-3-carboxamide (4.2 g, 7.22 mmol), of prepared in the previous step, in 150 mL of methylene chloride at dry ice-acetone temperature. After the addition the dry ice-acetone bath was replaced with an ice bath and the stirring continued for 3 h. At ice bath temperature water (100 mL) was added dropwise. The aqueous layer was separated and extracted two times with methylene chloride. The extracts were combined, extracted with saturated NaCl, dried (MgSO$_4$) and the solvent removed under reduced pressure to give N-benzyl-N-[(3'-bromo-4'-hydroxy-1,1'-biphenyl-4-yl)methyl]-2-butyl-1-benzofuran-3-carboxamide (3.1 g, 72%) as an off-white solid, MS (ESI) m/z 568 [M+H]$^+$. Elemental Analysis for $C_{33}H_{30}BrNO_3$: Calc'd: C, 69.72; H, 5.32; N, 2.46; Found: C, 68.69; H, 5.42; N, 2.28.

Step 5: N-benzyl-N-{[3'-bromo-4'-(cyanomethoxy)-1,1'-biphenyl-4-yl]methyl}-2-butyl-1-benzofuran-3-carboxamide. A mixture of N-benzyl-N-[(3'-bromo-4'-hydroxy-1,1'-biphenyl-4-yl)methyl]-2-butyl-1-benzofuran-3-carboxamide (1.5 g, 2.64 mmol), prepared in the previous step, bromoacetonitrile (220 µL, 3.16 mmol) and potassium carbonate (1.862 g, 13.5 mmol) in 75 mL of DMF was stirred under nitrogen at room temperature for 23 h. The reaction was partitioned between methylene chloride and water. If an emulsion forms saturated NaCl can be added to separate it. The organic layer was separated, extracted multiple times with water, dried (MgSO$_4$), and the solvent removed under reduced pressure to give N-benzyl-N-{[3'-bromo-4'-(cyanomethoxy)-1,1'-biphenyl-4-yl]methyl}-2-butyl-1-benzofuran-3-carboxamide (1.1 g, 69%) as a yellow oily solid, MS (ESI) m/z 607 [M+H]$^+$. Elemental Analysis for $C_{35}H_{31}BrN_2O_3$: Calc'd: C, 69.19; H, 5.14; N, 4.61; Found: C, 67.76; H, 5.44; N, 4.29

Step 6: N-benzyl-N-{[3'-bromo-4'-(1H-tetraazol-5-yl-methoxy)-1,1'-biphenyl-4-yl]methyl}-2-butyl-1-benzofuran-3-carboxamide. A mixture of N-benzyl-N-{[3'-bromo-4'-(cyanomethoxy)-1,1'-biphenyl-4-yl]methyl}-2-butyl-1-benzofuran-3-carboxamide (800 mg, 1.3 mmol), prepared in the previous step, sodium azide (320 mg, 4.9 mmol) and ammonium chloride (264 mg, 4.9 mmol) in 40 mL of DMF was stirred under nitrogen at 100° C. for 3.5 h. By TLC some starting material remained. An additional 320 mg (4.9 mmol) of sodium azide and 264 mg (4.9 mmol) of ammonium chloride were added and the reaction was stirred at 100° C. for 4 h. The reaction was diluted with water, made basic by the addition of 1 N NaOH and partitioned with ethyl acetate. The organic layer was separated and the aqueous layer extracted multiple times with ethyl acetate. By TLC the product was in the ethyl acetate layer. The ethyl acetate solution was concentrated. The residue was dissolved in methylene chloride and acidified with 1 N HCl. The organic layer was separated, extracted three times with water, dried (MgSO$_4$) and the solvent removed under reduced pressure to give the title compound (370 mg, 43%) as a white solid, MS (ESI) m/z 650 [M+H]$^+$. Elemental Analysis for $C_{35}H_{32}BrN_5O_3$.0.34 H$_2$O: Calc'd: C, 64.01; H, 5.02; N, 10.66; Found: C, 62.18; H, 5.32; N:9.50

Example 12

Synthesis of N-benzyl-N-{[3'-bromo-4'-(1H-tetraazol-5-ylmethoxy)-1,1'-biphenyl-4-yl]methyl}-1-methyl-1H-indole-3-carboxamide Step 1: N-benzyl-N-[(3'-bromo-4'-methoxy-1,1'-biphenyl-4-yl)methyl]-1-methyl-1H-indole-3-carboxamide. 1-methyl-1H-indole-3-carbonyl chloride (16.3 mmol), prepared in step 1 of Example 9, in 60 mL of methylene chloride was added under nitrogen dropwise over 15 minutes to a solution of the HCl salt of N-benzyl-N-[(3'-bromo-4'-methoxy-1,1'-biphenyl-4-yl)methyl]amine (5.0 g, 11.9 mmol), prepared in step 2 of Example 11, and triethylamine (4.6 mL, 33 mmol) in 100 mL of methylene chloride at room temperature. After the addition the reaction was stirred at room temperature for 16 h. The reaction was extracted with 1 N HCl, dried (MgSO$_4$) and the solvent removed under reduced pressure to give N-benzyl-N-[(3'-bromo-4'-methoxy-1,1'-biphenyl-4-yl)methyl]-1-methyl-1H-indole-3-carboxamide (6.1 g, 95%) as a white solid, MS (ESI) m/z 539 [M+H]$^+$. Elemental Analysis for $C_{31}H_{27}BrN_2O_2$: Calc'd: C, 69.02; H, 5.04; N, 5.19; Found: C, 68.55; H, 5.32; N, 4.99.

Step 2: N-benzyl-N-[(3'-bromo-4'-hydroxy-1,1'-biphenyl-4-yl)methyl]-1-methyl-1H-indole-3-carboxamide. Boron tribromide (22.0 mL of a 1 M solution in methylene chloride; 22.0 mmol) was added under nitrogen dropwise over 30 minutes to a solution of N-benzyl-N-[(3'-bromo-4'-methoxy-1,1'-biphenyl-4-yl)methyl]-1-methyl-1H-indole-3-carboxamide (4.3 g, 7.97 mmol), prepared in the previous step, in 150 mL of methylene chloride at dry ice-acetone temperature. After the addition the dry ice-acetone bath was replaced with an ice bath and the stirring continued for 3 h. At ice bath temperature water (100 mL) was added dropwise. The aqueous layer was separated and extracted two times with methylene chloride. The extracts were combined, extracted with saturated NaCl, dried (MgSO$_4$) and the solvent removed under reduced pressure to give N-benzyl-N-[(3'-bromo-4'-hydroxy-1,1'-biphenyl-4-yl)methyl]-1-methyl-1H-indole-3-carboxamide (3.3 g, 76%) as a white solid, MS (ESI) m/z 525 [M+H]$^+$. Elemental Analysis for $C_{30}H_{25}BrN_2O_2$: Calc'd: C, 68.58; H, 4.80; N, 5.33; Found: C, 67.54; H, 4.92; N, 5.17.

Step 3: N-benzyl-N-{[3'-bromo-4'-(cyanomethoxy)-1,1'-biphenyl-4-yl]methyl}-1-methyl-1H-indole-3-carboxamide. A mixture of N-benzyl-N-[(3'-bromo-4'-hydroxy-1,1'-biphenyl-4-yl)methyl]-1-methyl-1H-indole-3-carboxamide (1.5 g, 2.85 mmol), prepared in the previous step, bromoacetonitrile (240 µL, 3.44 mmol) and potassium carbonate (1.95 g, 14.1 mmol) in 75 mL of DMF was stirred under nitrogen at room temperature for 23 h. The reaction was partitioned between methylene chloride and water. The organic layer was separated, extracted multiple times with water, dried (MgSO$_4$) and the solvent removed under reduced pressure to give N-benzyl-N-{[3'-bromo-4'-(cyanomethoxy)-1,1'-biphenyl-4-yl]methyl}-1-methyl-1H-indole-3-carboxamide (1.2 g, 75%) as a white solid, MS (ESI) m/z 564 [M+H]+. Elemental Analysis for $C_{32}H_{26}BrN_3O_2$: Calc'd: C, 68.09; H, 4.64; N, 7.44; Found: C, 66.78; H, 4.68; N, 7.19.

Step 4: N-benzyl-N-{[3'-bromo-4'-(1H-tetraazol-5-yl-methoxy)-1,1'-biphenyl-4-yl]methyl}-1-methyl-1H-indole-3-carboxamide. A mixture of N-benzyl-N-{[3'-bromo-4'-(cyanomethoxy)-1,1'-biphenyl-4-yl]methyl}-1-methyl-1H-indole-3-carboxamide (800 mg, 1.4 mmol), prepared in the previous step, sodium azide (320 mg, 4.92 mmol) and ammonium chloride (264 mg, 4.94 mmol) in 40 mL of DMF was stirred under nitrogen at 100° C. for 5 h. The reaction was diluted with approximately 250 mL of water. The solid that formed was collected by filtration, rinsed with water and dried to give 390 mg of a solid. The solid was taken up in 1 N NaOH and then acidified with 1 N HCl. The solid that formed was collected by filtration and dried under reduced pressure to give the title compound (260 mg, 30%) as a white solid, MS (ESI) m/z 607 [M+H]$^+$. Elemental Analysis for $C_{32}H_{27}BrN_6O_2 \cdot 0.93\ H_2O$: Calc'd: C, 61.57; H, 4.66; N, 13.46; Found: C, 60.54; H, 4.89; N, 12.22.

Example 13

Synthesis of [(4'-{[(2-butyl-1-benzofuran-3-yl)carbonyl]amino}[1,1'-biphenyl]-4-yl)oxy]acetic acid Step 1: 4'-Methoxy-biphenyl-4-carboxylic acid methyl ester. Triethylamine (9.76 mL, 70 mmol) was added under nitrogen to a solution of 4'-hydroxy-biphenyl-4-carboxylic acid (15.0 g, 70 mmol) in 200 mL of anhydrous DMF at room temperature. After stirring for 5 minutes potassium carbonate (58.0 g, 420 mmol) was added and the reaction stirred an additional 5 minutes. Iodomethane (26.0 mL, 420 mmol) was then added (exothermic reaction) and the reaction stirred overnight. The reaction was diluted with methylene chloride, extracted multiple times with water, dried (MgSO$_4$) and the solvent removed under reduced pressure to give 4'-methoxy-biphenyl-4-carboxylic acid methyl ester (16.26 g, 96%) as a tan solid, mp 170-173° C. Elemental Analysis for $C_{15}H_{14}O_3$: Calc'd: C, 74.36; H, 5.82; N, 0.00; Found: C, 73.97; H, 5.66; N, 0.03.

Step 2: 4'-Methoxy-biphenyl-4-carboxylic acid. 1 N NaOH (148.5 mL, 148.5 mmol) was added under nitrogen to a solution of 4'-methoxy-biphenyl-4-carboxylic acid methyl ester (12.0 g, 49.5 mmol), prepared in the previous step, in 1 L of THF plus 250 mL of water at room temperature. After the addition the reaction was refluxed for 16.5 h (overnight). After cooling to approximately room temperature the reaction was acidified by the addition of 1 N HCl and then concentrated under reduced pressure. The solid that formed was collected by filtration and dried under reduced pressure to give 4'-methoxy-biphenyl-4-carboxylic acid (11.11 g, 98%) as a white solid, mp 245-250° C.; MS (ESI) m/z 227 [M−H]$^-$. Elemental Analysis for $C_{14}H_{12}O_3$: Calc'd: C, 73.67; H, 5.30; N, 0.00; Found: C, 69.52; H, 5.01; N, 0.04.

Step 3: tert-Butyl 4'-methoxy-4-biphenylcarbamate. A mixture of 4'-methoxy-biphenyl-4-carboxylic acid (10.68 g, 46.8 mmol), prepared in the previous step, triethylamine (6.52 mL, 46.8 mmol) and diphenylphosphoryl azide (10.08 mL, 46.8 mmol) in 200 mL of tert-butyl alcohol was refluxed under nitrogen for 7 h and then stood overnight at room temperature. The tert-butyl alcohol was removed under reduced pressure. The residue was dissolved in methylene chloride, extracted with 1 N HCl, 1 N NaOH, dried (MgSO$_4$) and the solvent removed under reduced pressure to give tert-butyl 4'-methoxy-4-biphenylcarbamate (11.1 g, 79%) as a white solid, mp 142-147° C., MS (ESI) m/z 300 [M+H]$^+$. Elemental Analysis for $C_{18}H_{21}NO_3$: Calc'd: C, 72.22; H, 7.07; N, 4.68; Found: C, 71.25; H, 6.92; N, 4.74.

Step 4: 4'-Amino-biphenyl-4-ol. A mixture of tert-butyl 4'-methoxy-4-biphenylcarbamate (8.32 g, 27.8 mmol), prepared in the previous step, 300 mL of glacial HOAc and 200 mL of 48% HBr was refluxed for 5 h. After cooling to room temperature the solid that was present was collected by filtration. The filtrate was cooled in an ice bath to give additional solid. The solids were combined and dried to give the HBr salt of 4'-amino-biphenyl-4-ol (5.33 g, 74%) as an off-white solid, MS (EI) m/z 185 [M]$^+$. Elemental Analysis for $C_{12}H_{11}NO$+HBr: Calc'd: C, 54.16; H, 4.54; N, 5.26; Found: C, 54.10; H, 4.42; N, 5.11.

Step 5: 2-Butyl-N-(4'-hydroxy[1,1'-biphenyl]-4-yl)-1-benzofuran-3-carboxamide. 2-Butyl-benzofuran-3-carbonyl chloride (2.22 g, 9.36 mmol), prepared in step 2 of Example 4, in 40 mL of anhydrous THF was added under nitrogen dropwise over 20 minutes to a mixture of the HBr salt of 4'-amino-biphenyl-4-ol (3.26 g, 12.3 mmol), prepared in the previous step, and triethylamine (3.42 mL, 24.5 mmol) in 100 mL of anhydrous THF at ice bath temperature. After the addition the reaction was stirred at room temperature for 20 h. The reaction was filtered and the filtrate concentrated under reduced pressure to give a solid. Purification of the solid on 1 Kg of silica gel (230-400 mesh) using 30% ethyl acetate-hexane as the eluent gave 2-butyl-N-(4'-hydroxy[1,1'-biphenyl]-4-yl)-1-benzofuran-3-carboxamide (2.27 g, 48%) as an off-white solid, mp 181-183° C.; MS (APCI) m/z 386 [M+H]$^+$. Elemental Analysis for $C_{25}H_{23}NO_3$: Calc'd: C, 77.90; H, 6.01; N, 3.63; Found: C, 77.48; H, 5.86; N, 3.56.

Step 6: Methyl[(4'-{[(2-butyl-1-benzofuran-3-yl)carbonyl]amino}[1,1'-biphenyl]-4-yl)oxy]acetate. A mixture of 2-butyl-N-(4'-hydroxy[1,1'-biphenyl]-4-yl)-1-benzofuran-3-carboxamide (900 mg, 2.34 mmol), prepared in the previous step, methyl bromoacetate (221 μL, 2.34 mmol) and potassium carbonate (1.61 g, 11.7 mmol) in 25 mL of DMF was stirred under nitrogen at room temperature for 24 h. The reaction was partitioned between methylene chloride and water. The organic layer was separated, extracted multiple times with water, dried (MgSO$_4$) and the solvent removed under reduced pressure to give 1.01 g of an off-white solid. Recrystallization of the solid from isopropyl alcohol gave methyl[(4'-{[(2-butyl-1-benzofuran-3-yl)carbonyl]amino}[1,1'-biphenyl]-4-yl)oxy]acetate (2.27 g, 48%) as white solid, mp 134-135° C.; MS (APCI) m/z 458 [M+H]$^+$. Elemental Analysis for $C_{28}H_{27}NO_5$: Calc'd: C, 73.51; H, 5.95; N, 3.06; Found: C, 72.83; H, 5.90; N, 3.04

Step 7: [(4'-{[(2-butyl-1-benzofuran-3-yl)carbonyl]amino}[1,1'-biphenyl]-4-yl)oxy]-acetic acid. 1 N NaOH (721 μL, 0.721 mmol) was added under nitrogen to a solution of methyl[(4'-{[(2-butyl-1-benzofuran-3-yl)carbonyl]amino}[1,1'-biphenyl]-4-yl)oxy]acetate (300 mg, 0.656 mmol), prepared in the previous step, in 30 mL of THF plus 10 mL of water at room temperature. After the addition the reaction was stirred at room temperature for 18 h (overnight). The reaction was acidified by the addition of 5 mL of 1 N HCl and then concentrated under reduced pressure. The solid that formed was collected by filtration and dried under reduced pressure to give the title compound (188 mg, 65%) as a white solid, mp 225-227° C.; MS (APCI) m/z 444 [M+H]$^+$. Elemental Analysis for $C_{27}H_{25}NO_5 \cdot 0.07\ H_2O$: Calc'd: C, 72.92; H, 5.70; N, 3.15; Found: C, 72.45; H, 5.64; N, 3.06

Example 14

Synthesis of 2-Butyl-N-[4'-(1H-tetraazol-5-ylmethoxy)[1,1'-biphenyl]-4-yl]-1-benzofuran-3-carboxamide Step 1: 2-Butyl-N-(4'-cyanomethoxy[1,1'-biphenyl]-4-yl)-1-benzofuran-3-carbox-amide. A mixture of 2-butyl-N-(4'-hydroxy[1,1'-biphenyl]-4-yl)-1-benzofuran-3-carboxamide (1.21 g, 3.14 mmol), prepared in step 5 of Example 13, bromoacetonitrile (263 μL, 3.77 mmol) and potassium carbonate (2.17 g, 15.7 mmol) in 25 mL of DMF was stirred under nitrogen at room temperature for 25 h. By TLC Starting material remained. An additional 284 µL (4.08 mmol) of bromoacetonitrile was added and the reaction was stirred at room temperature overnight. The reaction was partitioned between ethyl acetate and water. The organic layer was separated, dried (MgSO$_4$) and the solvent removed under reduced pressure to give 1.46 g of a brown solid. Purification of the solid on a 90 g KP-SIL 60 Å Biotage Column using methylene chloride as the eluent gave 2-butyl-N-(4'-cyanomethoxy[1,1'-biphenyl]-4-yl)-1-benzofuran-3-carboxamide (1.04 g, 78%) as a white solid, mp 143-144° C.; MS (ESI) m/z 425 [M+H]$^+$. Elemental Analysis for C$_{27}$H$_{24}$N$_2$O$_3$+0.06 CH$_2$Cl$_2$: Calc'd: C, 75.66; H, 5.66; N, 6.52; Found: C, 75.32; H, 5.41; N, 6.52

2-Butyl-N-[4'-(1H-tetraazol-5-ylmethoxy)[1,1'-biphenyl]-4-yl]-1-benzofuran-3-carboxamide. A mixture of 2-butyl-N-(4'-cyanomethoxy[1,1'-biphenyl]-4-yl)-1-benzofuran-3-carboxamide (400 mg, 0.942 mmol), prepared in the previous step, sodium azide (184 mg, 2.83 mmol) and ammonium chloride (151 mg, 2.83 mmol) was stirred under nitrogen at 100+ C. for 5.5 h. The reaction was diluted with ethyl acetate and extracted with 1 N NaOH. The aqueous layer was separated, extracted one additional time with ethyl acetate and acidified by the addition of 1 N HCl. The solid that formed was collected by filtration and dried under reduced pressure to give the title compound (257 mg, 59%) as a white solid, mp 210-212° C.; MS (APCI) m/z 468 ([M+H]$^+$. Elemental Analysis for C$_{27}$H25N$_5$O$_3$+0.06 H$_2$O: Calc'd: C, 69.20; H, 5.40; N, 14.94; Found: C, 68.83; H, 5.29; N, 14.98

Example 15

Synthesis of 4'-(2-methoxy-2-oxoethoxy)-1,1'-biphenyl-4-aminium chloride

Step 1: (4'-Hydroxy-biphenyl-4-yl)-carbamic acid tert-butyl ester. Triethylamine (786 µL, 5.64 mmol) and di-tert-butyl dicarbonate were added to a solution of 4'-amino-biphenyl-4-ol (0.5 g, 1.88 mmol), prepared in step 4 of Example 13, in DMF. After the addition the reaction stirred at room temperature overnight. The solvent was removed under reduced pressure and the residue partitioned between water and ethyl acetate. The aqueous layer was separated and extracted multiple times with ethyl acetate. The combined extracts were washed with brine, dried (Na$_2$SO$_4$) and the solvent removed under reduced pressure to give (4'-hydroxy-biphenyl-4-yl)-carbamic acid tert-butyl ester. The material was used in subsequent reactions without purification.

Step 2: (4'-tert-Butoxycarbonylamino-biphenyl-4-yloxy)-acetic acid methyl ester. Methyl bromoacetate (128.5 mg, 0.84 mmol) potassium iodide (11.7 mg) and potassium carbonate (193.5 mg, 1.4 mmol) were added to a solution of (4'-hydroxy-biphenyl-4-yl)-carbamic acid tert-butyl ester (0.2 g, 0.70 mmol), prepared in the previous step, in 15 mL of THF and the reaction stirred at room temperature overnight. The solvent was removed under reduced pressure. The residue was partitioned between ethyl acetate and water. The aqueous layer was separated and extracted multiple times with ethyl acetate. The combined extracts were dried (Na$_2$SO$_4$) and the solvent removed under reduced pressure. Purification of the residue on silica gel using 20% ethyl acetate-hexane as the eluent gave (4'-tert-butoxycarbonylamino-biphenyl-4-yloxy)-acetic acid methyl ester (208 mg, 80%) as a white solid.

Step 3: 4'-(2-methoxy-2-oxoethoxy)-1,1'-biphenyl-4-aminium chloride. 4 N HCl in dioxane (6.2 mL, 10 equiv) was added to a solution of (4'-tert-butoxycarbonylamino-biphenyl-4-yloxy)-acetic acid methyl ester (220 mg, 0.62 mmol), prepared in the previous step, in dioxane and the reaction stirred at room temperature for 2 h. The solid that formed was collected by filtration, rinsed with ethyl acetate and dried under reduced pressure to give 4'-(2-methoxy-2-oxoethoxy)-1,1'-biphenyl-4-aminium chloride (135 mg, 85%) as a white solid.

Example 16

Synthesis of (4'-Amino-biphenyl-4-yloxy)-acetic acid methyl ester

Step 1: 4'-Methoxy-4-nitro-biphenyl. A mixture of 4-methoxyphenylboronic acid (3.70 g, 24.3 mmol), 1-chloro-4-nitrobenzene (3.84 g, 24.3 mmol) and cesium fluoride (7.40 g, 48.7 mmol) in 150 mL of 2:1 acetonitrile-water was degassed under vacuum for 20 minutes. Tetrakis(triphenylphosphine)palladium(0) (844.0 mg, 0.73 mmol) was added and the reaction refluxed for 3 h. The solvent was removed under reduced pressure and the residue partitioned between methylene chloride and water. The organic phase was separated, dried (Na$_2$SO$_4$) and the solvent removed under reduced pressure. Purification of the residue on silica gel using 5% ethyl acetate hexanes as the eluent gave 4'-methoxy-4-nitro-biphenyl (4.55 g, 81%).

Step 2: 4'-Hydroxy-4-nitro-biphenyl. 4'-Methoxy-4-nitro-biphenyl (4.55 g, 19.8 mmol), prepared in the previous step, in a mixture of glacial acetic acid plus 65 mL of 48% HBr was heated at approximately 120° C. until the reaction was complete by TLC. The reaction was concentrated under reduced pressure and the residue partitioned between diethyl ether and water. The organic layer was separated, dried (Na$_2$SO$_4$) and the solvent removed under reduced pressure to give 4'-hydroxy-4-nitro-biphenyl.

Step 3: (4'-Nitro-biphenyl-4-yloxy)-acetic acid methyl ester. A mixture of 4'-hydroxy-4-nitro-biphenyl (2.00 g, 7.51 mmol), prepared in the previous step, methyl bromoacetate (853 mL, 9.02 mmol) and potassium iodide (86 mg, 0.75 mmol) in 50 mL of acetone was stirred at room temperature until the mixture became cloudy. Potassium carbonate (2.26 g, 16.4 mmol) was added and the reaction refluxed overnight. The reaction was concentrated under reduced pressure and the residue partitioned between methylene chloride and water. The organic layer was separated, washed with water, dried (Na$_2$SO$_4$) and the solvent removed under reduced pressure to give (4'-nitro-biphenyl-4-yloxy)-acetic acid methyl ester.

Step 4: (4'-Amino-biphenyl-4-yloxy)-acetic acid methyl ester. A mixture of (4'-nitro-biphenyl-4-yloxy)-acetic acid methyl ester (2.26 g, 7.86 mmol), prepared in the previous step, and 10% palladium on carbon in methanol was hydrogenated under a hydrogen atmosphere at room temperature. The reaction was filtered and the filtrate concentrated under reduced pressure. Purification of the residue on silica gel using 20% ethyl acetate hexanes as the eluent gave (4'-amino-biphenyl-4-yloxy)-acetic acid methyl ester (700 mg. 31%).

Example 17

Synthesis of (4'-Amino-biphenyl-3-yloxy)-acetic acid methyl ester

Prepared in the same manner as described in Example 16.

Example 18

Synthesis of 2-(4'-Amino-biphenyl-4-yloxy)-3-phenyl-propionic acid methyl ester Step 1: 2-(4'-Nitro-biphenyl-4-yloxy)-3-phenyl-propionic acid methyl ester. A mixture of 4'-hydroxy-4-nitro-biphenyl (4.12 g, 19.1 mmol), prepared in step 2 of Example 16, 2-hydroxy-3-phenyl-propionic acid methyl ester (3.35 g, 18.5 mmol) and triphenylphosphine (4.12 g, 19.1 mmol) in diethyl ether was cooled under nitrogen to 0° C. Diisopropyl azodicarboxylate (6.09 mL, 30.96 mmol) was then added and the reaction allowed to come to room temperature and then stirred overnight at room temperature. The reaction was concentrated under reduced pressure. Purification of the residue on silica gel using 15% ethyl acetate hexanes as the eluent gave 2-(4'-nitro-biphenyl-4-yloxy)-3-phenyl-propionic acid methyl ester.

Step 2: 2-(4'-Amino-biphenyl-4-yloxy)-3-phenyl-propionic acid methyl ester. Prepared in the same manner as described in step 4 of Example 16 (1.38 g, 45%).

Example 19

Synthesis of 2-(4'-Amino-biphenyl-3-yloxy)-3-phenyl-propionic acid methyl ester Prepared in the same manner as described in Example 18.

Examples 20-58

Step 1: General Procedure for the Preparation of Acid Chlorides. A solution of acid and oxalyl chloride (1.5 equivalents) in methylene chloride containing a catalytic amount of DMF was stirred under nitrogen at room temperature overnight. The solvent was removed under reduced pressure and the crude acid chloride used in subsequent reactions without purification.

Step 2: General Procedure for the Acylation of the Amines Prepared in Examples 15 to 19. A solution of the acid chloride, prepared in the previous step, the appropriate amine (1 equivalent), prepared in Examples 15 to 19, and an excess of triethylamine in THF was stirred under nitrogen at room temperature overnight. The reaction was concentrated under reduced pressure and the residue partitioned between methylene chloride and water. The aqueous layer was extracted multiple times with methylene chloride. The combined organic extracts were dried ($Na_2SO_4$) and the solvent removed under reduced pressure to give the desired amides.

Step 3: General Procedure for the Hydrolysis of the Acetates Prepared in Step 2. 2 N NaOH was added to a solution of the acetates, prepared in the previous step, in methanol plus THF (1:1) and the reaction stirred at room temperature for 24 h. The reaction was acidified with 1 N HCl and then concentrated under reduced pressure. The residue was partitioned between methylene chloride and water. The aqueous layer was extracted multiple times with methylene chloride. The combined extracts were concentrated under reduced pressure to dryness to give the desired acid.

Example 20

3-phenyl-2-[(4'-{[(4'-propyl-1,1'-biphenyl-4-yl)carbonyl]amino}-1,1'-biphenyl-4-yl)oxy]propanoic acid HRMS Calc'd for $C_{37}H_{33}NO_4$ [M−H]: 554.23368. Found: 554.23369.

Example 21

2-[(4'-{[5-(4-chlorophenyl)-2-furoyl]amino}-1,1'-biphenyl-4-yl)oxy]-3-phenylpropanoic acid HRMS Calc'd for $C_{32}H_{24}ClNO_5$ [M−H]: 536.12702. Found: 536.12699.

Example 22

{[4'-({[1-(4-chlorophenyl)cyclopentyl]carbonyl}amino)-1,1'-biphenyl-4-yl]oxy}acetic acid HRMS Calc'd for $C_{26}H_{24}ClNO_4$ [M−H]: 448.13211. Found: 448.1319.

Example 23

{[4'-({[1-(3-fluorophenyl)cyclopentyl]carbonyl}amino)-1,1'-biphenyl-4-yl]oxy}acetic acid HRMS Calc'd for $C_{26}H_{24}FNO_4$ [M−H]: 432.16166. Found: 432.16148.

Example 24

2-({4'-[(9H-fluoren-4-ylcarbonyl)amino]-1,1'-biphenyl-3-yl}oxy)-3-phenylpropanoic acid HRMS Calc'd for $C_{35}H_{27}NO_4$ [M−H]: 524.18673. Found: 524.1866.

Example 25

3-phenyl-2-[(4'-{[(1-phenylcyclopentyl)carbonyl]amino}-1,1'-biphenyl-3-yl)oxy]propanoic acid HRMS Calc'd for $C_{33}H_{31}NO_4$ [M−H]: 504.21803. Found: 504.21781.

Example 26

2-{[4'-({[1-(4-chlorophenyl)cyclopentyl]carbonyl}amino)-1,1'-biphenyl-3-yl]oxy}-3-phenylpropanoic acid HRMS Calc'd for $C_{33}H_{30}ClNO_4$ [M−H]: 538.17906. Found: 538.17892.

Example 27

2-{[4'-({[1-(4-chlorophenyl)-5-propyl-1H-pyrazol-4-yl]carbonyl}amino)-1,1'-biphenyl-3-yl]oxy}-3-phenylpropanoic acid HRMS Calc'd for $C_{34}H_{30}ClN_3O_4$ [M−H]: 578.1852. Found: 578.18504.

Example 28

2-{[4'-({[5-(benzyloxy)-1H-indol-2-yl]carbonyl}amino)-1,1'-biphenyl-3-yl]oxy}-3-phenylpropanoic acid HRMS Calc'd for $C_{37}H_{30}N_2O_5$ [M−H]: 581.20819. Found: 581.20808.

Example 29

2-{4'-({[1-(4-chlorophenyl)cyclopropyl]carbonyl}amino)-1,1'-biphenyl-3-yl]oxy}-3-phenyl-propanoic acid HRMS Calc'd for $C_{31}H_{26}ClNO_4$ [M–H]: ND

Example 30

2-{4'-({[1-(3-fluorophenyl)cyclopentyl]carbonyl}amino)-1,1'-biphenyl-3-yl]oxy}-3-phenyl-propanoic acid HRMS Calc'd for $C_{33}H_{30}FNO_4$ [M–H]: 522.20861. Found: 522.20844.

Example 31

3-phenyl-2-[(4'-{[(1-phenylcyclopentyl)carbonyl]amino}-1,1'-biphenyl-4-yl)oxy]Propanoic acid HRMS Calc'd for $C_{33}H_{31}NO_4$ [M–H]: 504.21803. Found: 504.21786.

Example 32

3-phenyl-2-[(4'-{[(1-phenylcyclopropyl)carbonyl]amino}-1,1'-biphenyl-4-yl)oxy]Propanoic acid HRMS Calc'd for $C_{31}H_{27}NO_4$ [M–H]: 476.18673. Found: 476.18653.

Example 33

2-{4'-({[1-(4-chlorophenyl)cyclopropyl]carbonyl}amino)-1,1'-biphenyl-4-yl]oxy}-3-phenyl-propanoic acid HRMS Calc'd for $C_{31}H_{26}ClNO_4$ [M–H]: 510.14776. Found: 510.14763.

Example 34

2-{4'-({[1-(3-fluorophenyl)cyclopentyl]carbonyl}amino)-1,1'-biphenyl-4-yl]oxy}-3-phenyl-propanoic acid HRMS Calc'd for $C_{33}H_{30}FNO_4$ [M–H]: 522.20861. Found: 522.20844.

Example 35

{[4'-({[1-(4-chlorophenyl)cyclobutyl]carbonyl}amino)-1,1'-biphenyl-4-yl]oxy}acetic acid HRMS Calc'd for $C_{25}H_{22}ClNO_4$ [M–H]: 434.11646. Found: 434.11631.

Example 36

[(4'-{[5-(1,1'-biphenyl-4-yl)-2-(trifluoromethyl)-3-furoyl]amino}-1,1'-biphenyl-4-yl)oxy]acetic acid HRMS Calc'd for $C_{32}H_{22}F_3NO_5$ [M–H]: 556.13773. Found: 556.13764.

Example 37

2-({4'-[(4-phenoxybenzoyl)amino]-1,1'-biphenyl-3-yl}oxy)-3-phenylpropanoic acid

HRMS Calc'd for $C_{34}H_{27}NO_5$ [M–H]: 528.18164. Found: 528.18149.

Example 38

2-{4'-({[5-(4-chlorophenyl)thien-2-yl]carbonyl}amino)-1,1'-biphenyl-3-yl]oxy}-3-phenyl-propanoic acid HRMS Calc'd for $C_{32}H_{24}ClNO_4S$ [M–H]: 552.10418. Found: 552.10405.

Example 39

2-{4'-({[1-(4-chlorophenyl)cyclobutyl]carbonyl}amino)-1,1'-biphenyl-3-yl]oxy}-3-phenyl-propanoic acid HRMS Calc'd for $C_{32}H_{28}ClNO_4$ [M–H]: 524.16341. Found: 524.16329.

Example 40

2-[(4'-{[5-(2-chlorophenyl)-2-(trifluoromethyl)-3-furoyl]amino}-1,1'-biphenyl-3-yl)oxy]-3-phenylpropanoic acid HRMS Calc'd for $C_{33}H_{23}ClF_3NO_5$ [M–H]: 604.11441. Found: 604.11429.

Example 41

2-[(4'-{[(2-butyl-1-benzofuran-3-yl)carbonyl]amino}-1,1'-biphenyl-3-yl)oxy]-3-phenylpropanoic acid HRMS Calc'd for $C_{34}H_{31}NO_5$ [M–H]: 532.21294. Found: 532.21281.

Example 42

2-[(4'-{[5-(1,1'-biphenyl-4-yl)-2-(trifluoromethyl)-3-furoyl]amino}-1,1'-biphenyl-3-yl)oxy]-3-phenylpropanoic acid HRMS Calc'd for $C_{39}H_{28}F_3NO_5$ [M–H]: 646.18468. Found: 646.18464.

Example 43

3-phenyl-2-{[4'-({2-(trifluoromethyl)-5-[4-(trifluoromethyl)phenyl]-3-furoyl}amino)-1,1'-biphenyl-3-yl]oxy}propanoic acid HRMS Calc'd for $C_{34}H_{23}F_6NO_5$ [M–H]: 638.14076. Found: 638.14071.

Example 44

2-{[4'-({5-[(4-bromo-3,5-dimethyl-1H-pyrazol-1-yl)methyl]-2-furoyl}amino)-1,1'-biphenyl-3-yl]oxy}-3-phenylpropanoic acid HRMS Calc'd for $C_{32}H_{28}BrN_3O_5$ [M−H]: 612.11395. Found: 612.11387.

Example 45

2-({4'-[(4-phenoxybenzoyl)amino]-1,1'-biphenyl-4-yl}oxy)-3-phenylpropanoic acid

HRMS Calc'd for $C_{34}H_{27}NO_5$ [M−H]: 528.18164. Found: 528.18151.

Example 46

2-{[4'-({[5-(4-chlorophenyl)thien-2-yl]carbonyl}amino)-1,1'-biphenyl-4-yl]oxy}-3-phenylpropanoic acid HRMS Calc'd for $C_{32}H_{24}ClNO_4S$ [M−H]: 552.10418. Found: 552.10409.

Example 47

2-{[4'-({[1-(4-chlorophenyl)cyclobutyl]carbonyl}amino)-1,1'-biphenyl-4-yl]oxy}-3-phenylpropanoic acid HRMS Calc'd for $C_{32}H_{28}ClNO_4$ [M−H]: ND

Example 48

2-[(4'-{[5-(2-chlorophenyl)-2-(trifluoromethyl)-3-furoyl]amino}-1,1'-biphenyl-4-yl)oxy]-3-phenylpropanoic acid HRMS Calc'd for $C_{33}H_{23}ClF_3NO_5$ [M−H]: 604.11441. Found: 604.11436.

Example 49

2-[(4'-{[(2-butyl-1-benzofuran-3-yl)carbonyl]amino}-1,1'-biphenyl-4-yl)oxy]-3-phenylpropanoic acid HRMS Calc'd for $C_{34}H_{31}NO_5$ [M−H]: 532.21294. Found: 532.21283.

Example 50

3-phenyl-2-{[4'-({2-(trifluoromethyl)-5-[4-(trifluoromethyl)phenyl]-3-furoyl}amino)-1,1'-biphenyl-4-yl]oxy}propanoic acid HRMS Calc'd for $C_{34}H_{23}F_6NO_5$ [M−H]: 638.14076. Found: 638.14098.

Example 51

2-{[4'-({[1-(4-chlorophenyl)cyclohexyl]carbonyl}amino)-1,1'-biphenyl-3-yl]oxy}-3-phenylpropanoic acid HRMS Calc'd for $C_{34}H_{32}ClNO_4$ [M−H]: 552.19471. Found: 552.19443.

Example 52

2-{[4'-({[1-(4-chlorophenyl)cyclopentyl]carbonyl}amino)-1,1'-biphenyl-4-yl]oxy}-3-phenylpropanoic acid HRMS Calc'd for $C_{33}H_{30}ClNO_4$ [M−H]: 538.17906. Found: 538.17886.

Example 53

3-phenyl-2-[(4'-{[(1-phenylcyclopropyl)carbonyl]amino}-1,1'-biphenyl-3-yl)oxy]propanoic acid HRMS Calc'd for $C_{31}H_{27}NO_4$ [M−H]: 476.18673. Found: 476.18644.

Example 54

3-phenyl-2-[(4'-{[(2,2,5,7-tetramethyl-1-oxo-2,3-dihydro-1H-inden-4-yl)carbonyl]amino}-1,1'-biphenyl-3-yl)oxy]propanoic acid HRMS Calc'd for $C_{35}H_{33}NO_5$ [M−H]: 546.22859. Found: 546.22845.

Example 55

2-{[4'-(2-naphthoylamino)-1,1'-biphenyl-4-yl]oxy}-3-phenylpropanoic acid

HRMS Calc'd for $C_{32}H_{25}NO_4$ [M−H]: 486.17108. Found: 486.17081.

Example 56

2-({4'-[(6-butoxy-2-naphthoyl)amino]-1,1'-biphenyl-4-yl}oxy)-3-phenylpropanoic acid HRMS Calc'd for $C_{36}H_{33}NO_5$ [M−H]: 558.22859. Found: 558.22844.

Example 57

2-[(4'-{[(3-chloro-1-benzothien-2-yl)carbonyl]amino}-1,1'-biphenyl-4-yl)oxy]-3-phenylpropanoic acid HRMS Calc'd for $C_{30}H_{22}ClNO_4S$ [M−H]: 526.08853. Found: 526.08845.

Example 58

Primary Screen for the PAI-1 Inhibition

Test compounds are dissolved in DMSO at a final concentration of 10 mM, then diluted 101× in physiologic buffer. The inhibitory assay is initiated by the addition of the test compound (1-100 μM final concentration, maximum DMSO concentration of 0.2%) in a pH 6.6 buffer containing 140 nM recombinant human plasminogen activator inhibitor-1 (PAI-1; *Molecular Innovations*, Royal Oak, Mich.). Following a 1 hour incubation at room temperature, 70 nM of recombinant human tissue plasminogen activator (tPA) is added, and the combination of the test compound, PAI-1 and tPA is incubated for an additional 30 minutes. Following the second incubation, Spectrozyme-tPA (*American Diagnostica*, Greenwich, Conn.), a chromogenic substrate for tPA, is added and absorbance read at 405 nm at 0 and 60 minutes. Relative PAI-1 inhibition is equal to the residual tPA activity in the presence of the test compound and PAI-1. Control treatments include the complete inhibition of tPA by PAI-1 at the molar ratio employed (2:1), and the absence of any effect of the test compound on tPA alone.

Example 59

Assay for Determining $IC_{50}$ of Inhibition of PAI-1

This assay is based upon the non-SDS dissociable interaction between tPA and active PAI-1. Assay plates are initially coated with human tPA (10 μg/ml). Test compounds of the present invention are dissolved in DMSO at 10 mM, then diluted with physiologic buffer (pH 7.5) to a final concentration of 1-50 μM. Test compounds are incubated with human PAI-1 (50 ng/ml) for 15 minutes at room temperature. The tPA-coated plate is washed with a solution of 0.05% Tween 20 and 0.1% BSA, then the plate is blocked with a solution of 3% BSA. An aliquot of the substituted biphenyloxy acid/PAI-1 solution is then added to the tPA-coated plate, incubated at room temperature for 1 hour, and washed. Active PAI-1 bound to the plate is assessed by adding an aliquot of a 1:1000 dilution of the 33B8 monoclonal antibody against human PAI-1, and incubating the plate at room temperature for 1 hour (*Molecular Innovations*, Royal Oak, Mich.). The plate is again washed, and a solution of goat anti-mouse IgG-alkaline phosphatase conjugate is added at a 1:50,000 dilution in goat serum. The plate is incubated 30 minutes at room temperature, washed, and a solution of alkaline phosphatase substrate is added. The plate is incubated 45 minutes at room temperature, and color development is determined at $OD_{405nm}$. The quantitation of active PAI-1 bound to tPA at varying concentrations of the test compound is used to determine the $IC_{50}$. Results are analyzed using a logarithmic best-fit equation. The assay sensitivity is 5 ng/ml of human PAI-1 as determined from a standard curve ranging from 0-100 ng/ml.

The compounds of the present invention inhibited Plasminogen Activator Inhibitor-1 as summarized in Table 1.

TABLE 1

| Compound | $IC_{50}$ (Antibody)[a] μM | $IC_{50}$ (Kinetic)[b] μM | % Inhibition 100 μM | % Inhibition 25 μM |
|---|---|---|---|---|
| 1 |  |  | 60 | 1 |
| 2 |  |  | 66 | 2 |
| 3 | 37.45 |  | 88 | 47 |
| 4 |  |  | 82 | 44 |
| 5 |  |  | 73 | 23 |
| 6 | 10.84 |  | 94 | 42 |
| 7 | 18.74 |  | 100 | 64 |
| 8 | 20.05 |  | 96 | 55 |
| 9 | 46.31 |  | 81 | 41 |
| 10 | 29.99 |  | 76 | 45 |
| 11 |  |  |  | 53 |
| 12 |  |  |  | 55 |
| 13 |  |  | 85 | 25 |
| 14 |  |  | 62 | 29 |

TABLE 1-continued

| Compound | $IC_{50}$ (Antibody)[a] μM | $IC_{50}$ (Kinetic)[b] μM | % Inhibition 100 μM | % Inhibition 25 μM |
|---|---|---|---|---|
| 20 |  |  | 66 | 40 |
| 21 |  |  | 52 | 28 |
| 22 |  |  | 89 | 30 |
| 23 |  |  | 77 | 3 |
| 24 |  | 12.1 | 51 | 36 |
| 25 |  | 40.8 | 74 | 26 |
| 26 |  | 16.4 | 69 | 58 |
| 27 |  | 7.8 | 63 | 20 |
| 28 |  | 7.41 | 70 | 27 |
| 29 |  | 31.2 | 83 | 31 |
| 30 |  | 17.45 | 73 | 23 |
| 31 |  | 31.1 | 51 | 24 |
| 32 |  | 4.04 | 78 | 15 |
| 33 |  | 13.9 | 79 | 22 |
| 34 |  | 38.6 | 70 | 33 |
| 35 |  | 39.3 | 80 | 15 |
| 36 |  | 18.33 | 75 | 29 |
| 37 |  | 18.13 | 65 | 13 |
| 38 |  | 38.7 | 52 | 5 |
| 39 |  | 12 | 81 | 40 |
| 40 |  | 10.22 | 90 | 31 |
| 41 |  | 9.1 | 95 | 30 |
| 42 |  | 18.6 | 57 | 35 |
| 43 |  | 12 | 88 | 26 |
| 44 |  | 11.8 | 52 | 17 |
| 45 |  | 11.5 | 61 | 34 |
| 46 |  | 5.4 | 84 | 36 |
| 47 |  | 18.1 | 83 | 14 |
| 48 |  | 23.2 | 78 | 7 |
| 49 |  | 8.71 | 90 | 25 |
| 50 |  | 18.7 | 95 | 27 |
| 51 |  |  | 60 | 46 |
| 52 |  |  | 53 | 55 |
| 53 |  |  | 52 | 19 |
| 54 |  |  | 85 | 29 |
| 55 |  |  | 53 | 26 |
| 56 |  |  | 53 |  |
| 57 |  |  | 58 | 34 |

[a]The $IC_{50}$ was determined by the Antibody Assay as described above.
[b]The $IC_{50}$ was determined by a modification of the Primary Screen for the PAI-1 Inhibition.

Although the foregoing invention has been described in detail by way of example for purposes of clarity of understanding, it will be apparent to the artisan that certain changes and modifications are comprehended by the disclosure and can be practiced without undue experimentation within the scope of the appended claims, which are presented by way of illustration not limitation.

All publications and patent documents cited above are hereby incorporated by reference in their entirety for all purposes to the same extent as if each were so individually denoted.

What is claimed is:

1. A compound of the formula:

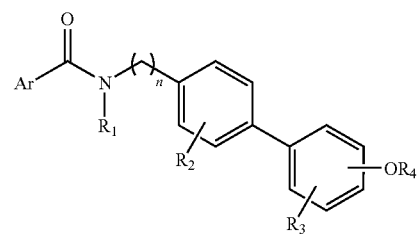

Formula 1 or a pharmaceutically acceptable salt or ester form thereof; wherein:

Ar is furanyl, thiophenyl, benzofuranyl, benzothiophenyl, indolyl, pyrazolyl or oxazolyl;

$R_1$ is hydrogen, $C_1$-$C_6$ alkyl or —$(CH_2)_r$-phenyl;

$R_2$ and $R_3$ are independently hydrogen, $C_1$-$C_6$ alkyl, —$(CH_2)_p$-phenyl, halogen or $C_1$-$C_3$ perfluoroalkyl;

$R_4$ is —$CH(R_5)(CO_2H)$, tetrazole, —$CH_2$-tetrazole, tetronic acid or a group of the formula:

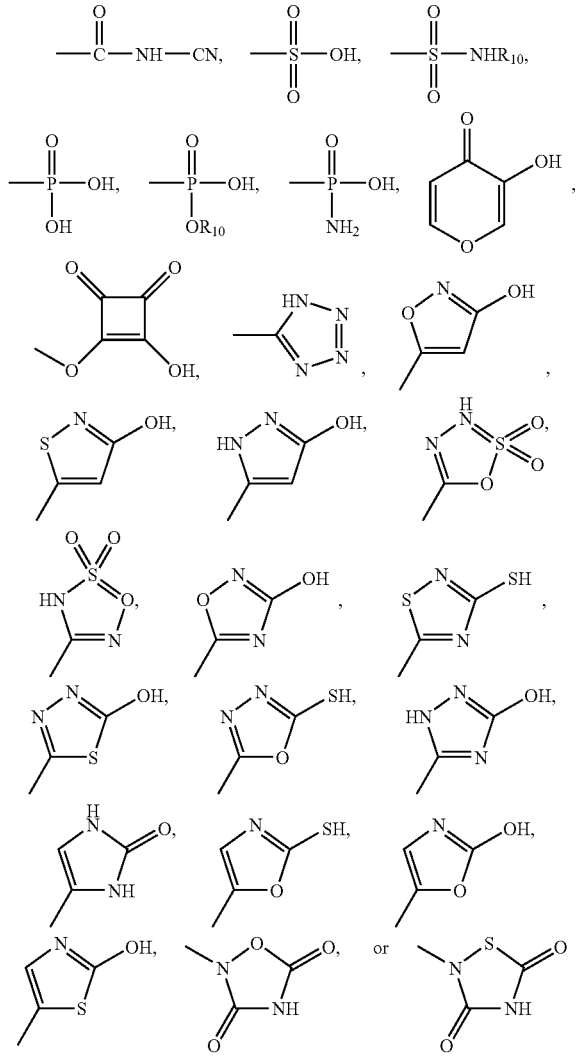

$R_{18}$ is $C_1$-$C_6$ alkyl, $C_2$-$C_6$ alkenyl, $C_3$-$C_6$ cycloalkyl, —$CH_2$—($C_3$-$C_6$ cycloalkyl), —$C_3$-$C_6$ cycloalkenyl, —$CH_2$—($C_3$-$C_6$ cycloalkenyl), optionally substituted aryl, optionally substituted heteroaryl, optionally substituted —$C_1$-$C_6$ alkyl-aryl, or optionally substituted —$C_1$-$C_6$ alkyl-heteroaryl;

$R_5$ is hydrogen or benzyl;

n is 0 or 1;

r is from 0 to 6;

p is from 0 to 3 wherein Ar, alkyl, phenyl and benzyl groups are optionally substituted.

2. The compound of claim 1 wherein

Ar is furanyl, thiophenyl, benzofuranyl, benzothiophenyl, indolyl, pyrazolyl or oxazolyl; each substituted with from 1 to 3 groups selected from $C_1$-$C_6$ alkyl, $C_1$-$C_6$ alkoxy, hydroxy, $C_3$-$C_6$ cycloalkyl, —$(CH_2)$—$C_3$-$C_6$ cycloalkyl, halogen, $C_1$-3 perfluoroalkyl, $C_1$-$C_3$ perfluoroalkoxy, —$(CH_2)_q$-phenyl, and —$O(CH_2)_q$-phenyl;

and wherein the phenyl group of —$(CH2)_q$-phenyl and —$O(CH_2)_q$-phenyl is optionally substituted with from 1 to 3 groups selected from $C_1$-$C_6$ alkyl, $C_1$-$C_6$ alkoxy, phenyl, halogen, trifluoromethyl or trifluoromethoxy; and q is from 0 to 6; or a pharmaceutically acceptable salt or ester form thereof.

3. The compound of claim 1 of the formula:

Formula 2

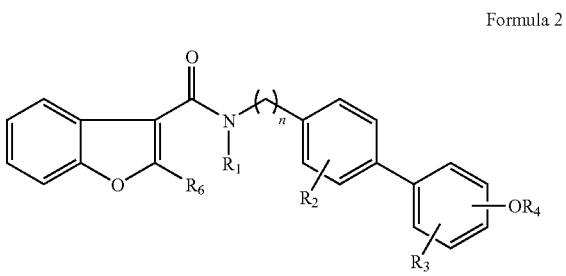

or a pharmaceutically acceptable salt or ester form thereof, wherein:

$R_6$ is hydrogen, $C_1$-$C_6$ alkyl, $C_1$-$C_6$ alkoxy, hydroxy, —$(CH_2)_q$-phenyl, —$O(CH_2)_q$-phenyl, $C_3$-$C_6$ cycloalkyl, halogen, $C_1$-$C_3$ perfluoroalkyl or $C_1$-$C_3$ perfluoroalkoxy and q is from 0 to 6.

4. The compound of claim 3 wherein $R_6$ is hydrogen or $C_1$-$C_6$ alkyl; or a pharmaceutically acceptable salt or ester form thereof.

5. A compound of claim 1 of the formula:

Formula 4

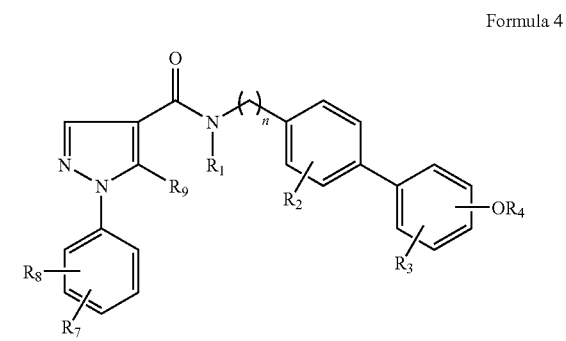

or a pharmaceutically acceptable salt or ester form thereof, wherein $R_7$, $R_8$ and $R_9$ are, independently, hydrogen, $C_1$-$C_6$ alkyl, $C_1$-$C_6$ alkoxy, hydroxy, —$(CH_2)_q$-phenyl, —$O(CH_2)_q$-phenyl, $C_3$-$C_6$ cycloalkyl, halogen, $C_1$-$C_3$ perfluoroalkyl or $C_1$-$C_3$ perfluoroalkoxy and q is from 0 to 6.

6. A compound of claim 1 of the formula:

Formula 5

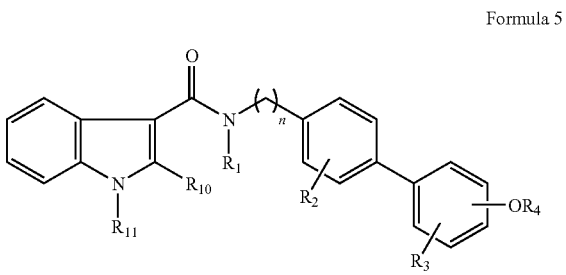

or a pharmaceutically acceptable salt or ester form thereof, wherein $R_{10}$ is hydrogen, $C_1$-$C_6$ alkyl, $C_1$-$C_6$ alkoxy, hydroxy, —(CH₂)_q-phenyl, —O(CH₂)_q-phenyl, C₃-C₆ cycloalkyl, halogen, C₁-C₃ perfluoroalkyl or C₁-C₃ perfluoroalkoxy; R₁₁ is hydrogen, C₁-C₆ alkyl, —(CH₂)_q-phenyl, or (CH₂)_q—C₃-C₆ cycloalkyl; and q is from 0 to 6.

7. A compound of claim 1 of the formula:

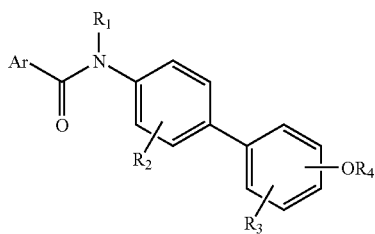

Formula 6 or a pharmaceutically acceptable salt or ester form thereof; wherein:

Ar₁ is formula A or formula B

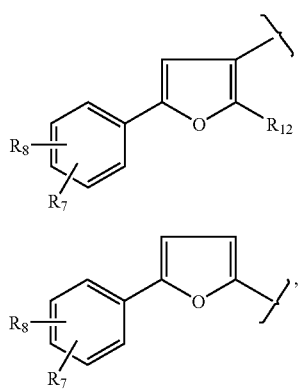

Formula A

Formula B wherein R₇, R₈ and R₁₂ are, independently, hydrogen, C₁-C₆ alkyl, C₁-C₆ alkoxy, hydroxy, —(CH₂)_q-phenyl, —O(CH₂)_q-phenyl, C₃-C₆ cycloalkyl, halogen, C₁-C₃ perfluoroalkyl or C₁-C₃ perfluoroalkoxy; and q is from 0 to 6.

8. A compound according to claim 1 wherein R₁ is hydrogen, C₁-C₆ alkyl or —(CH₂)_r-phenyl wherein the phenyl ring is optionally substituted with CH₁₋₆ alkyl, C₁₋₆ alkoxy, halogen, trifluoromethyl, or trifluoromethoxy; or a pharmaceutically acceptable salt or ester form thereof.

9. A compound according to claim 1 wherein R₁ is methyl, benzyl, or hydrogen; or a pharmaceutically acceptable salt or ester form thereof.

10. A compound according to claim 1 wherein R₄ is —CH(R₅)(CO₂H); or a pharmaceutically acceptable salt or ester form thereof.

11. A compound according to claim 10 wherein R₅ is hydrogen or benzyl wherein the benzyl ring is optionally substituted with from 1 to 3 groups selected from the group consisting of C₁-C₆ alkyl, C₁-C₆ alkoxy, hydroxy, C₃-C₆ cycloalkyl, —(CH₂)—C₃-C₆ cycloalkyl, halogen, C₁-C₃ perfluoroalkyl, C₁-C₃ perfluoroalkoxy, —(CH₂)_q-phenyl, and —O(CH₂)CH_q-phenyl and wherein the phenyl group of —(CH₂)_q-phenyl and —O(CH₂)_q-phenyl is optionally substituted with from 1 to 3 groups selected from the group consisting of C₁-C₆ alkyl, C₁-C₆alkoxy, phenyl, halogen, trifluoromethyl or trifluoromethoxy; and q is from 0 to 6; or a pharmaceutically acceptable salt or ester form thereof.

12. A compound according to claim 1 wherein R₄ is —CH₂-tetrazole.

13. A compound according to claim 1 wherein R₂ and R₃ are independently hydrogen, C₁-C₆ alkyl, —(CH₂)_q-phenyl, halogen or C₁-C₃ perfluoroalkyl wherein the phenyl ring is optionally substituted with C₁₋₆ alkyl, C₁₋₆ alkoxy, halogen, trifluoromethyl, or trifluoromethoxy; or a pharmaceutically acceptable salt or ester form thereof.

14. A compound according to claim 1 wherein R₂ is hydrogen and R₃ is hydrogen, C₁₋₆ alkyl, or halogen; or a pharmaceutically acceptable salt or ester form thereof.

15. A compound of claim 1 that is 2-({[4'-({[5-(4-chlorophenyl)thien -2-yl]carbonyl}amino)-1,1'-biphenyl-3-yl]oxy}-3-phenyl propanoic acid or a pharmaceutically acceptable salt or ester form thereof; 2-{[4'-({5-[(4-bromo-3,5-dimethyl-1H-pyrazol-1-yl)methyl]-2-furoyl}amino)-1,1'-biphenyl-3-yl]oxy}-3-phenylpropanoic acid or a pharmaceutically acceptable salt or ester form thereof; or 2-{[4'-({[5-(4-chlorophenyl)thien-2-yl]carbonyl}amino)-1,1'-biphenyl-4-yl]oxy}-3-phenyl propanoic acid or a pharmaceutically acceptable salt or ester form thereof.

16. A compound of claim 1 that is 2-[(4'-{[(3-chloro-1-benzothien-2-yl) carbonyl]amino}-1,1'-bipphenyl-4-yl)oxy]-3-phenylpropanoic acid or a pharmaceutically acceptable salt or ester form thereof; 2-{[4'-({[5-(benzyloxy)-1H-indol-2-yl]carbonyl}amino)-1,1'-biphenyl-3-yl]oxy}-3-phenyl propanoic acid or a pharmaceutically acceptable salt or ester form thereof; {[3-bromo-4'-({[(2-butyl-1-benzofuran-3-yl)carbonyl]amino}methyl )[1,1'-biphenyl]-4-yl]oxy}acetic acid or a pharmaceutically acceptable salt or ester form thereof or [(3-bromo-4'-{[[(2-butyl-1-benzofuran-3-yl)carbonyl](methyl)amino]methyl}-1,1'-biphenyl-4-yl)oxy]acetic acid or a pharmaceutically acceptable salt or ester form thereof.

17. A compound of claim 1 that is 2-[(3-bromo-4'-{[[(2-butyl-1-benzofuran-3-yl)carbonyl](methyl)amino]methyl}-1,1'-biphenyl-4-yl)oxy]-3-phenylpropanoic acid; [(4'-{[(2-butyl-1-benzofuran-3-yl)carbonyl]amino}]1,1'-biphenyl]-4-yl)oxy]acetic acid; 2-[(4'-{[(2-butyl-1-benzofuran-3-yl)carbonyl]amino}-1,1'-biphenyl-3-yl)oxy]-3-phenylpropanoic acid; 2-[(4'-{[(2-butyl-1-benzo furan-3-yl)carbonyl]amino}-1,1'-biphenyl-4-yl)oxy]-3-phenylpropanoic; N-{[3'-bromo-4'-(1H-tetraazol-5-ylmethoxy)-1,1'-biphenyl-4-yl]methyl}-2-butyl-N -methyl-1-benzofuran-3-carboxamide; or N-benzyl-N-{[3'-bromo-4'-(1H-tetraazol -5-ylmethoxy)-1,1'-biphenyl-4-yl]methyl}-2-butyl-1-benzofuran-3-carboxamide; or a pharmaceutically acceptable salt or ester form thereof.

18. A compound of claim 1 that is 2-butyl-N-[4'-(1H-tetraazol-5-ylmethoxy)[1,1'-biphenyl]-4-yl]-1-benzofuran-3-carboxamide; —or—a pharmaceutically acceptable salt or ester form thereof.

19. A compound of claim 1 that is ({4'-[({[1-phenyl-5-(trifluoromethyl)-1H-pyrazol-4-yl]carbonyl}amino)methyl][1,1'-biphenyl]-4-yl}oxy)acetic acid or a pharmaceutically acceptable salt or ester form thereof; ({4'-[({[1-phenyl-5-propyl-1H-pyrazol-4-yl]carbonyl}amino)methyl][1,1'-biphenyl]-4-yl}oxy)acetic acid or a pharmaceutically acceptable salt or ester form thereof; {[3-bromo-4'-({[(1-phenyl-5-propyl-1H-pyrazol-4-yl)carbonyl]amino}methyl)][1,1'-biphenyl]-4-yl]oxy}acetic acid or a pharmaceutically acceptable salt or ester form thereof; or 2-{[4'-({[1-(4-chlorophenyl)-5-propyl-1H-pyrazol-4-yl]carbonyl}amino)-1,1'-biphenyl-3-yl]oxy}-3-phenylpropanoic acid or a pharmaceutically acceptable salt or ester form thereof.

20. A compound of claim 1 that is N-{[3'-bromo-4'-(1H-tetraazol-5-ylmethoxy)[1,1'-biphenyl]-4-yl]methyl}-1-phenyl-5-propyl-1H-pyrazole-4-carboxamide; N-{[3'-bromo-4'-(1H-tetraazol-5-ylmethoxy)-1,1-biphenyl-4-yl]methyl}-N,1-dimethyl-1H-indole-3-carboxamide; 1-Benzyl-N-{[3'-bromo-4'-(1H-tetraazol-5-ylmethoxy)-1,1'-biphenyl-4-yl [methyl]-N-methyl-1H-indole-3-carboxamide; —N-benzyl-N-{[3'-bromo-4'-(1H-tetraazol-5-ylmethoxy)-1,1'-biphenyl-4-yl]methyl}-1-methyl-1H-indole-3-carboxamide; 2-[(4'-{[5-(4-chloro phenyl)-2-furoyl]amino}-1,1'-biphenyl-4-yl)oxy]-3-phenylpropanoic acid; or [(4'-{[5-(1,1'-biphenyl-4-yl)-2-(trifluoromethyl)-3-furoyl}amino}-1,1'-biphenyl-4-yl)oxy]acetic acid; or a pharmaceutically acceptable salt or ester form thereof.

21. A compound of claim 1 that is 2-[(4'-{[5-(2-chlorophenyl)-2-(trifluoromethyl)-3-furoyl[amino}-1,1'-biphenyl-3-yl)oxy]-3-phenylpropanoic acid or a pharmaceutically acceptable salt or ester form thereof; 2-[(4'-{[5-(1,1'-biphenyl-4-yl)-2-(trifluoromethyl)-3-furoyl]amino}-1,1'-biphenyl-3-yl)-oxy]-3-phenylpropanoic acid or a pharmaceutically acceptable salt or ester form thereof; 3-phenyl-2-{[4'-({2-(trifluoromethyl)-5-[4-(trifluoromethyl)phenyl]-3-furoyl}amino)-1,1'-biphenyl-3-yl]oxy}propanoic acid or a pharmaceutically acceptable salt or ester form thereof; 2-[(4'-{[5-(2-chlorophenyl)-2-(trifluoromethyl)-3-furoyl]amino}-1,1'-biphenyl-4-yl)oxy]-3-phenylpropanoic acid or a pharmaceutically acceptable salt or ester form thereof; or 3-phenyl-2-{[4'-({2-(trifluoromethyl)-5-[4-(trifluoromethyl)phenyl]-3-furoyl}amino)-1,1'-biphenyl-4-yl]oxy}propanoic acid or a pharmaceutically acceptable salt or ester form thereof.

22. A method of inhibiting PAI-1 activity comprising administering to a subject in need thereof a therapeutically effective amount of a compound according to claim 1, or a pharmaceutically acceptable salt or ester form thereof.

23. A pharmaceutical composition comprising the compound according to claim 1, or a pharmaceutically acceptable salt or ester form thereof, and a pharmaceutically acceptable excipient or carrier.

* * * * *